United States Patent
Kim et al.

(10) Patent No.: US 8,911,885 B2
(45) Date of Patent: *Dec. 16, 2014

(54) HETEROARYLAMINE COMPOUND AND ORGANIC LUMINESCENCE DEVICE USING THE SAME

(75) Inventors: Young-Kook Kim, Yongin (KR); Seok-Hwan Hwang, Yongin (KR); Yoon-Hyun Kwak, Yongin (KR); Hye-Jin Jung, Yongin (KR); Jong-Hyuk Lee, Yongin (KR); Jin-O Lim, Yongin (KR); Chang-Ho Lee, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 173 days.

This patent is subject to a terminal disclaimer.

(21) Appl. No.: 12/857,540

(22) Filed: Aug. 16, 2010

(65) Prior Publication Data

US 2011/0049487 A1  Mar. 3, 2011

(30) Foreign Application Priority Data

Aug. 28, 2009  (KR) .................. 10-2009-0080702

(51) Int. Cl.
*H01L 51/54* (2006.01)
*C07D 209/58* (2006.01)
(Continued)

(52) U.S. Cl.
CPC ............ *C07D 405/04* (2013.01); *C07D 209/60* (2013.01); *C07D 209/86* (2013.01);
(Continued)

(58) Field of Classification Search
USPC .............................. 428/690, 917, 411.1, 336;
313/502–509; 257/40, 88, 104, E51;
548/427, 442, 304.4, 305.1; 540/1;
532/1; 438/361.1; 585/27
See application file for complete search history.

(56) References Cited

U.S. PATENT DOCUMENTS 6,280,859 B1   8/2001 Onikubo et al.
6,465,115 B2  10/2002 Shi et al.
(Continued)

FOREIGN PATENT DOCUMENTS

JP    10251633        9/1998
JP    10310574 A     11/1998
(Continued)

OTHER PUBLICATIONS

Machine English translation of JP 2008-133225 A. Jun. 4, 2012.*

(Continued)

*Primary Examiner* — J. L. Yang
(74) *Attorney, Agent, or Firm* — Christie, Parker & Hale, LLP

(57) ABSTRACT

Embodiments of the present invention are directed to heteroarylamine compounds and organic luminescence devices including the heteroarylamine compounds. The organic luminescence devices using the heteroarylamine compounds have high-efficiency, low driving voltages, high luminance and long lifetimes. The heteroarylamine compounds are represented by the following formula:

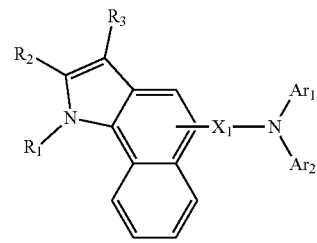

17 Claims, 1 Drawing Sheet

(51) Int. Cl.
| | |
|---|---|
| *C07D 403/14* | (2006.01) |
| *C07D 403/12* | (2006.01) |
| *C07D 405/04* | (2006.01) |
| *C07D 209/60* | (2006.01) |
| *C07D 209/86* | (2006.01) |
| *C07D 209/88* | (2006.01) |
| *C07D 405/14* | (2006.01) |
| *C07D 409/04* | (2006.01) |
| *C07D 409/14* | (2006.01) |

(52) U.S. Cl.
CPC ........... *C07D 209/88* (2013.01); *C07D 405/14* (2013.01); *C07D 409/04* (2013.01); *C07D 409/14* (2013.01)
USPC .............. 428/690; 548/427; 548/442; 585/27

(56) References Cited

U.S. PATENT DOCUMENTS

| | | |
|---|---|---|
| 6,596,415 B2 | 7/2003 | Shi et al. |
| 8,399,880 B2 * | 3/2013 | Kim et al. ........................ 257/40 |
| 2007/0278938 A1 | 12/2007 | Yabunouchi et al. |
| 2008/0124572 A1 | 5/2008 | Mizuki et al. |
| 2010/0045170 A1 | 2/2010 | Lee et al. |

FOREIGN PATENT DOCUMENTS

| | | | |
|---|---|---|---|
| JP | 2002148835 A | | 5/2002 |
| JP | 2005093159 A | | 4/2005 |
| JP | 2008133225 A | | 6/2008 |
| JP | 2008133225 A | * | 6/2008 |
| KR | 1020080112325 A | | 12/2008 |
| KR | 10-2009-0024431 | | 3/2009 |
| KR | 10-0910150 B1 | | 8/2009 |
| WO | WO 2009/031807 A2 | | 3/2009 |
| WO | WO 2009/061156 A1 | | 5/2009 |

OTHER PUBLICATIONS

KIPO Registration Determination Certificate dated Mar. 2, 2012, for Korean priority Patent application 10-2009-0080702, (5 pages).
SIPO Office action dated May 30, 2013, issued in corresponding CN Application No. 201010268636.6 (6 pages).
SIPO Office action issued May 20, 2013 in corresponding CN Application No. 201010268636.6, with English translation (12 pages).

* cited by examiner

HETEROARYLAMINE COMPOUND AND ORGANIC LUMINESCENCE DEVICE USING THE SAME

CROSS-REFERENCE TO RELATED PATENT APPLICATION

This application claims priority to and the benefit of Korean Patent Application No. 10-2009-0080702, filed on Aug. 28, 2009 in the Korean Intellectual Property Office, the entire content of which is incorporated herein by reference.

BACKGROUND OF THE INVENTION

1. Field of the Invention

The present invention relates to heteroarylamine compounds and to organic luminescence devices including the heteroarylamine compounds.

2. Description of the Related Art

Electroluminescent (EL) devices are self-emission type display devices having wide viewing angles, high contrast ratios, and short response times. Due to these characteristics, EL devices are drawing more attention. Such EL devices can be roughly classified into inorganic EL devices (which include emission layers containing inorganic compounds), and organic EL devices (which include emission layers containing organic compounds). Specifically, organic EL devices have higher brightness, lower driving voltages, and shorter response times than inorganic EL devices, and can produce multi-colored displays. Thus, much research into organic EL devices has been conducted.

In general, an organic EL device has an anode/organic emitting layer/cathode structure, but can include at least one additional layer selected from hole injection layers and hole transport layers formed between the anode and the emitting layer, and electron injection layers formed between the emitting layer and the cathode. For example, an organic EL device can have an anode/hole transport layer/organic emitting layer/cathode structure or an anode/hole transport layer/organic emitting layer/electron transport layer/cathode structure.

Organic EL devices including hole injection layers and/or hole transport layers using known materials have unsatisfactory lifetime, efficiency, and power consumption. Thus, there is a need to improve these characteristics.

SUMMARY OF THE INVENTION

According to embodiments of the present invention, an organic layer material has improved electrical stability and charge transporting capability, high glass transition temperature, and improved ability to prevent crystallization. The organic layer material is suitable for fluorescent or phosphorescent organic EL devices (OLEDs), including full-color OLEDs (which can generate all colors, including red, green, blue, and white). Other embodiments of the present invention are directed to methods of preparing the organic layer material.

In some embodiments of the present invention, an OLED includes an organic layer formed of the above-described material. The OLED has good durability during storage and driving, high efficiency, low driving voltage, and improved luminance. In other embodiments, a flat panel display device includes the OLED.

According to an embodiments of the present invention, a heteroarylamine compound is represented by Formula 1:

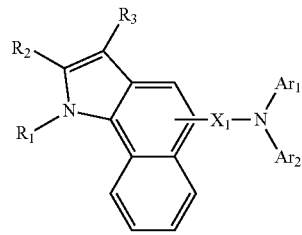

Formula 1

In Formula 1, each of $Ar_1$ and $Ar_2$ is independently selected from substituted and unsubstituted C6-C60 aryl groups, substituted and unsubstituted C4-C60 heteroaryl groups, and substituted and unsubstituted C6-C60 condensed polycyclic groups. $X_1$ is selected from substituted and unsubstituted C6-C30 arylene groups, substituted and unsubstituted C4-C30 heteroarylene groups, and substituted and unsubstituted C6-C30 condensed polycyclic groups. Each of $R_1$, $R_2$, and $R_3$ is independently selected from hydrogen atoms, heavy hydrogen atoms, substituted and unsubstituted C1-C50 alkyl groups, substituted and unsubstituted C1-C50 alkoxy groups, substituted and unsubstituted C6-C60 aryl groups, substituted and unsubstituted C3-C50 carbocyclic groups, substituted and unsubstituted C4-C60 hetero aryl groups, substituted and unsubstituted C4-C60 heterocyclic groups, substituted and unsubstituted C6-C60 condensed polycyclic groups, halogen atoms, cyano groups, hydroxyl groups, and carboxyl groups.

According to other embodiments of the present invention, an organic luminescence device includes a first electrode, a second electrode, and an organic layer between the first electrode and the second electrode, wherein the organic layer includes at least one layer including the heteroarylamine compound. The organic layer may include a hole injection layer or a hole transport layer.

According to some embodiments of the present invention, a flat panel display device includes the organic luminescence device, wherein the first electrode of the organic light-emitting device is electrically connected to a source electrode or a drain electrode of a thin-film transistor.

According to still other embodiments of the present invention, an organic luminescence display device includes the organic luminescence device, wherein at least one layer of the organic luminescence device includes the heteroarylamine compound and the at least one layer is formed using a wet process.

BRIEF DESCRIPTION OF THE DRAWINGS

The above and other features and advantages of the present invention will become more apparent by reference to the following detailed description when considered in conjunction with the attached drawing in which.

DETAILED DESCRIPTION OF THE INVENTION

Figure 1:
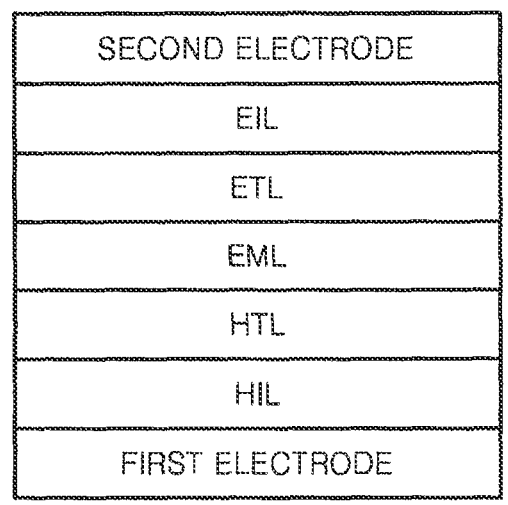
FIG. 1 is a schematic view of an organic light-emitting device according to an embodiment of the present invention.

According to embodiments of the present invention, a heteroarylamine compound is represented by Formula 1 below.

In some embodiments, the heteroarylamine compound may be used to form an organic layer of an organic electroluminescence device (OLED).

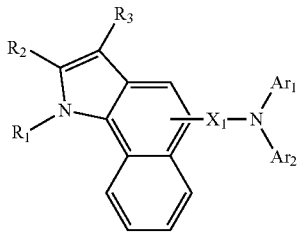

Formula 1

In Formula 1, each of $Ar_1$ and $Ar_2$ is independently selected from substituted and unsubstituted C6-C60 aryl groups, substituted and unsubstituted C4-C60 heteroaryl groups, and substituted and unsubstituted C6-C60 condensed polycyclic groups. $X_1$ is selected from substituted and unsubstituted C6-C30 arylene groups, substituted and unsubstituted C4-C30 heteroarylene groups, and substituted and unsubstituted C6-C30 condensed polycyclic groups. Each of $R_1$, $R_2$, and $R_3$ is independently selected from hydrogen atoms, heavy hydrogen atoms, substituted and unsubstituted C1-C50 alkyl groups, substituted and unsubstituted C1-C50 alkoxy groups, substituted and unsubstituted C6-C60 aryl groups, substituted and unsubstituted C3-C50 carbocyclic groups, substituted and unsubstituted C4-C60 hetero aryl groups, substituted and unsubstituted C4-C60 heterocyclic groups, substituted and unsubstituted C6-C60 condensed polycyclic groups, halogen atoms, cyano groups, hydroxyl groups, and carboxyl groups.

In Formula 1, $X_1$ is a linker, nonlimiting examples of which include bivalent organic groups represented by the following formulae.

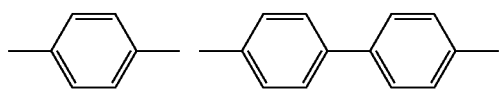

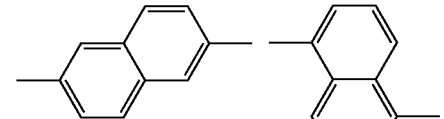

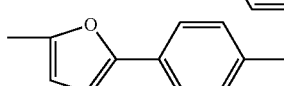

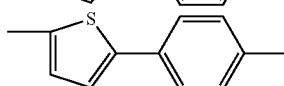

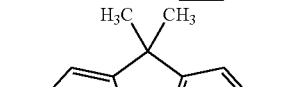

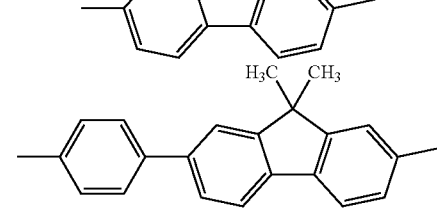

The amine compound of Formula 1 may be used in various applications and includes a linker ($X_1$) bonded to a phenyl group of an indole group.

The amine compound of Formula 1 has high durability during storage and driving. In addition, due to the introduction of a substituent such as a fluorene group, the state of the organic layer formed using the amine compound of Formula 1 is improved. Thus, the characteristics of the organic luminescence device including such an organic layer are improved.

According to an embodiment of the present invention, the amine compound of Formula 1 may be selected from compounds represented by Formulae 2 through 6:

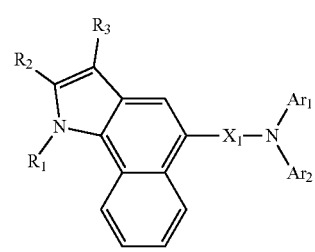

Formula 2

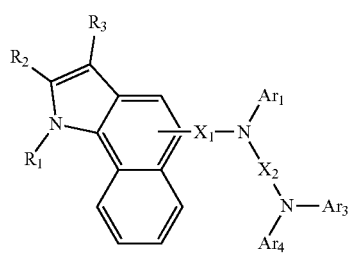

Formula 3

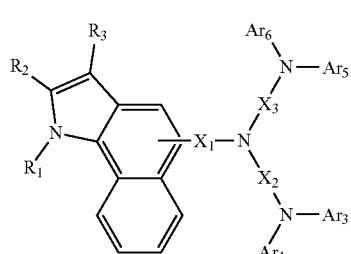

Formula 4

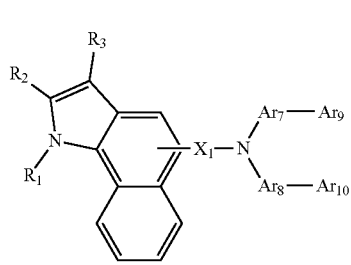

Formula 5

Formula 6

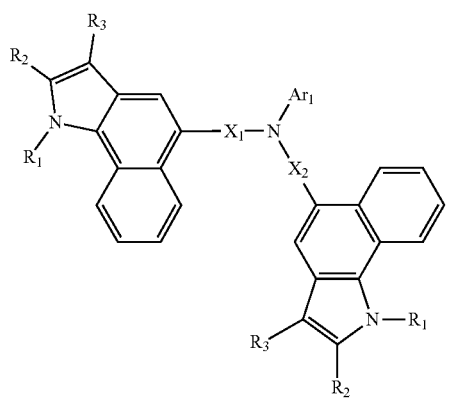

In Formulae 2 through 6, each of $Ar_1$ through $Ar_6$, $Ar_9$ and $Ar_{10}$ is independently selected from substituted and unsubstituted C6-C60 aryl groups, substituted and unsubstituted C4-C60 heteroaryl groups, and substituted and unsubstituted C6-C60 condensed polycyclic groups. Each of $X_1$, $X_2$, $X_3$, $Ar_7$ and $Ar_8$ is independently selected from substituted and unsubstituted C6-C30 arylene groups, substituted and unsubstituted C4-C30 heteroarylene groups, and substituted and unsubstituted C6-C30 condensed polycyclic groups. Each of $R_1$, $R_2$, and $R_3$ is independently selected from hydrogen atoms, heavy hydrogen atoms, substituted and unsubstituted C1-C50 alkyl groups, substituted and unsubstituted C1-C50 alkoxy groups, substituted and unsubstituted C6-C60 aryl groups, substituted and unsubstituted C3-C50 carbocyclic groups, substituted and unsubstituted C4-C60 hetero aryl groups, substituted and unsubstituted C4-C60 heterocyclic groups, substituted and unsubstituted C6-C60 condensed polycyclic groups, halogen atoms, cyano groups, hydroxyl groups, and carboxyl groups.

In some embodiments, in Formulae 1 through 6, and Formulae 2 through 6 in particular, each of $R_1$, $R_2$, and $R_3$ is independently selected from aryl groups, nonlimiting examples of which include phenyl groups, 4-fluorophenyl groups, naphthalene groups, and biphenyl groups.

In some embodiments, in Formulae 1 through 6, and Formulae 2 through 6 in particular, each of $X_1$, $X_2$, and $X_3$ may be selected from bivalent organic groups, nonlimiting examples of which include those represented by the following formulae.

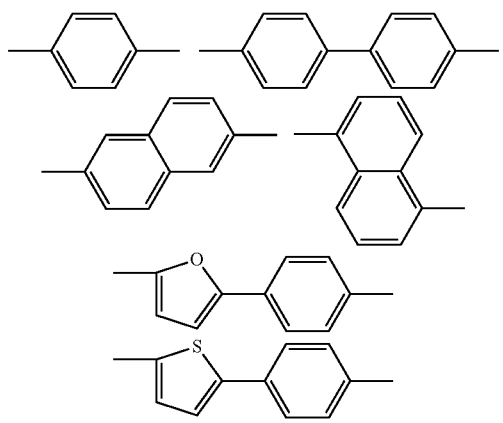

In some embodiments, in Formulae 1 through 6, and Formulae 2 through 6 in particular, each of $Ar_1$ through $Ar_6$, $Ar_9$ and $Ar_{10}$ may be independently selected from monovalent groups, nonlimiting examples of which include those represented by the following formulae.

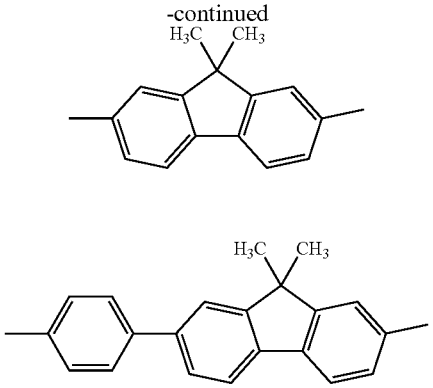

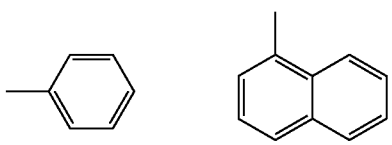

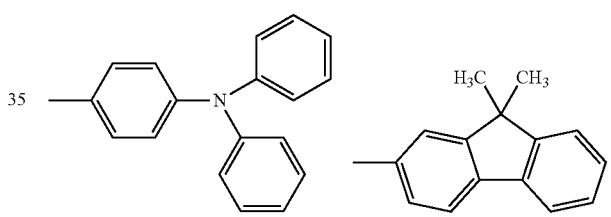

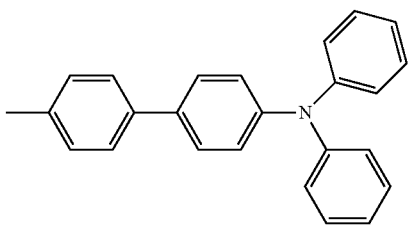

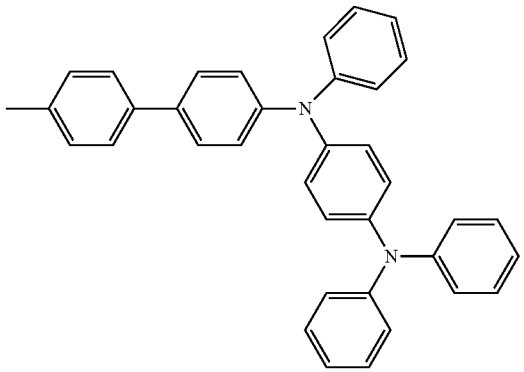

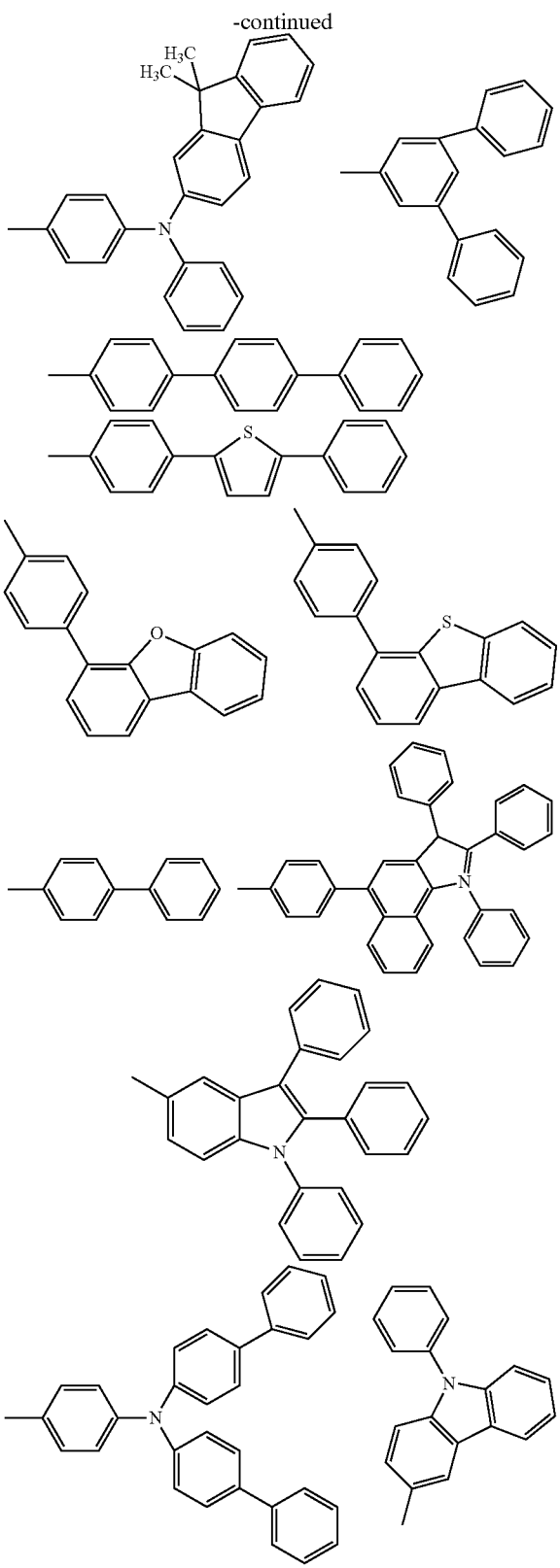

Hereinafter, the functional groups used in the formulas described above will be described.

The unsubstituted $C_1$-$C_{50}$ alkyl group may be linear or branched. Nonlimiting examples of the alkyl group include methyl groups, ethyl groups, propyl groups, isobutyl groups, sec-butyl groups, pentyl groups, isoamyl groups, hexyl groups, heptyl groups, octyl groups, nonanyl groups, and dodecyl groups. At least one hydrogen atom of the alkyl group may be substituted with a substituent selected from heavy hydrogen atoms, halogen atoms, hydroxyl groups, nitro groups, cyano groups, amino groups, amidino groups, hydrazines, hydrazones, carboxyl groups and salts thereof, sulfonic acid groups and salts thereof, phosphoric acid groups and salts thereof, $C_1$-$C_{10}$ alkyl groups, $C_1$-$C_{10}$ alkoxy groups, $C_2$-$C_{10}$ alkenyl groups, $C_2$-$C_{10}$ alkynyl groups, $C_6$-$C_{16}$ aryl groups, and $C_4$-$C_{16}$ heteroaryl groups.

The unsubstituted $C_3$-$C_{50}$ carbocyclic group refers to a $C_3$-$C_{50}$ cycloalkyl group where at least one hydrogen atom in the carbon ring may be substituted with the substituents described above in connection with the $C_1$-$C_{50}$ alkyl group.

The unsubstituted $C_4$-$C_{60}$ heterocyclic group refers to a $C_4$-$C_{60}$ cycloalkyl group including one, two or three hetero atoms selected from N, O, P and S, where at least one hydrogen atom in the heterocyclic group may be substituted with the substituents described above in connection with the $C_1$-$C_{50}$ alkyl group.

The unsubstituted $C_1$-$C_{50}$ alkoxy group is a group having a —OA structure where A is an unsubstituted $C_1$-$C_{50}$ alkyl group as described above. Nonlimiting examples of the alkoxy group include methoxy groups, ethoxy groups, propoxy groups, isopropyloxy groups, butoxy groups, and pentoxy groups. At least one hydrogen atom of the alkoxy group may be substituted with the substituents described above in connection with the $C_1$-$C_{50}$ alkyl group.

The unsubstituted $C_6$-$C_{60}$ aryl group refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with the substituents described above in connection with the $C_1$-$C_{50}$ alkyl group.

Nonlimiting examples of the substituted or unsubstituted $C_6$-$C_{60}$ aryl group include phenyl groups, $C_1$-$C_{10}$ alkylphenyl groups (for example, ethylphenyl groups), halophenyl groups (for example, o-, m-, and p-fluorophenyl groups, dichlorophenyl groups), cyanophenyl groups, dicyanophenyl groups, trifluoromethoxyphenyl groups, biphenyl groups, halobiphenyl groups, cyanobiphenyl groups, $C_1$-$C_{10}$ alkyl biphenyl groups, $C_1$-$C_{10}$ alkoxybiphenyl groups, o-, m-, and p-toryl groups, o-, m-, and p-cumenyl groups, mesityl groups, phenoxyphenyl groups, (α,α-dimethylbenzene)phenyl groups, (N,N'-dimethyl)aminophenyl groups, (N,N'-diphenyl)aminophenyl groups, pentalenyl groups, indenyl groups, naphthyl groups, halonaphthyl groups (for example, fluoronaphthyl groups), $C_1$-$C_{10}$ alkylnaphthyl groups (for example, methylnaphthyl groups), $C_1$-$C_{10}$ alkoxynaphthyl groups (for example, methoxynaphthyl groups), cyanonaphthyl groups, anthracenyl groups, azulenyl groups, heptalenyl groups, acenaphthylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

The unsubstituted $C_4$-$C_{60}$ heteroaryl group includes one, two or three hetero atoms selected from N, O, P and S. At least two rings may be fused to each other or linked to each other by a single bond. Nonlimiting examples of the unsubstituted $C_4$-$C_{60}$ heteroaryl group include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. At least one hydrogen atom in the heteroaryl group may be substituted with the substituents described above in connection with the $C_1$-$C_{50}$ alkyl group.

The unsubstituted $C_6$-$C_{60}$ condensed polycyclic group refers to a substituent including at least two rings where at least one aromatic ring and/or at least one non-aromatic ring are fused to each other. The unsubstituted $C_6$-$C_{60}$ polycyclic condensed group may include some of the substituents described in connection with the aryl group or the heteroaryl group.

The amine compound of Formula 1 may be used as an organic layer material. For example, the amine compound may be used as at least one of a hole injection material, a hole transport material, and an emitting material.

The amine compound of Formula 1 has an indole group, and therefore has a high glass transition temperature (Tg) and a high melting point due to introduction of the indole group. Thus, during electroluminescence, the amine compound of Formula 1 has high resistance to Joule heat (which is generated in an organic layer, between organic layers or between an organic layer and a metallic electrode), and high durability under high-temperature environments. Thus, organic electroluminescent (EL) devices manufactured using the amine compound of Formula 1 have high durability during storage and driving.

Nonlimiting examples of amine compounds of Formula 1 include Compounds 1-111.

1

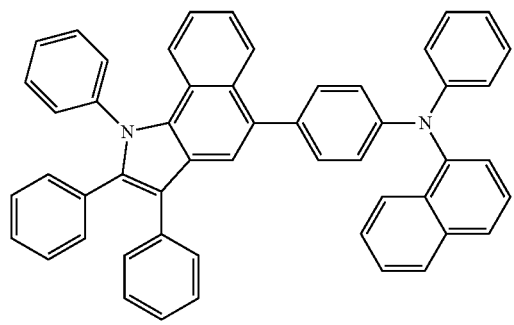

2

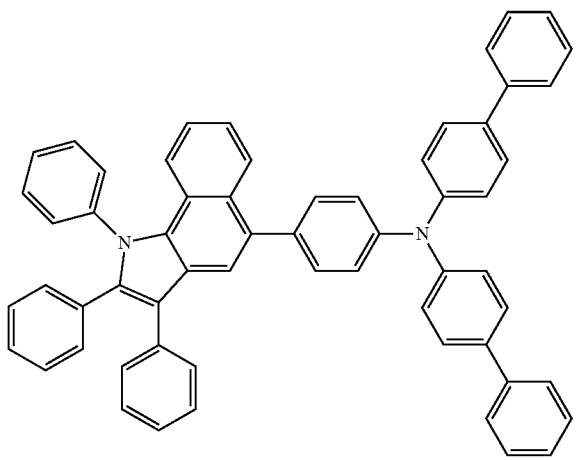

3

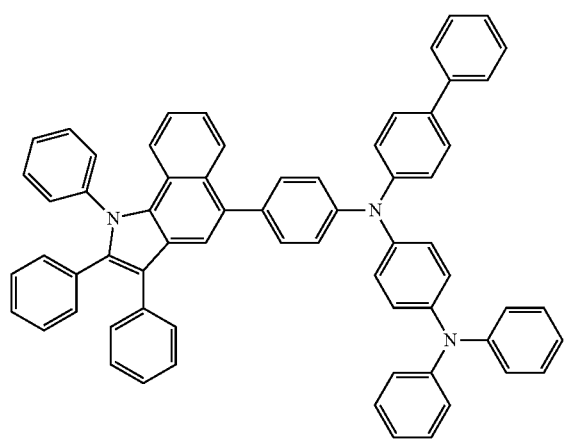

4

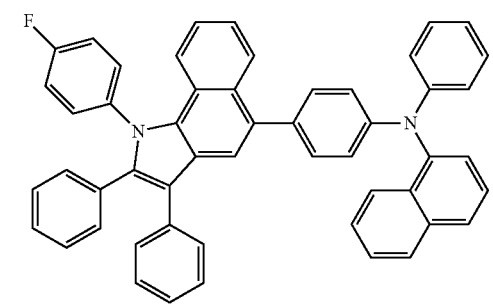

5

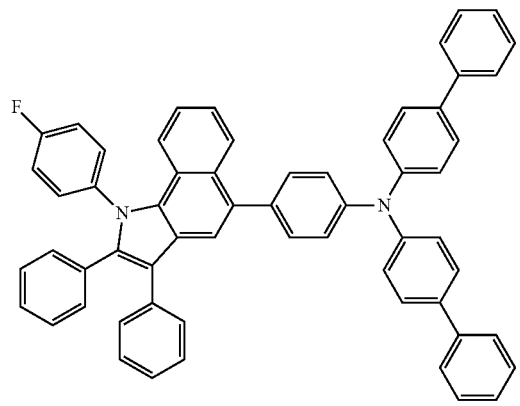

6

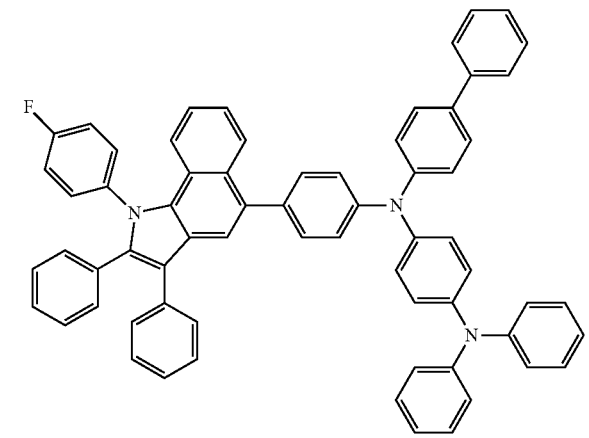

-continued
7
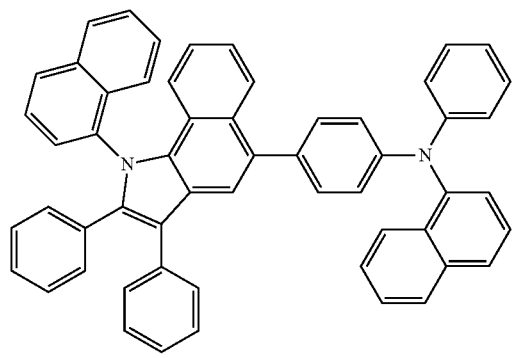
8
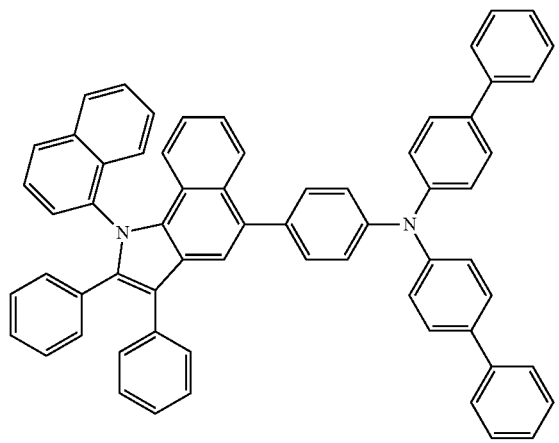
9
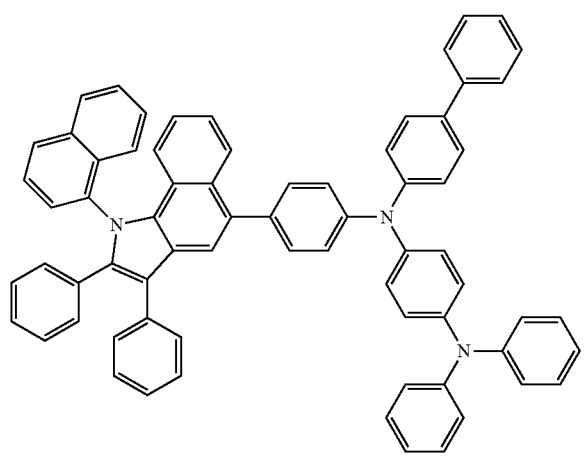
10
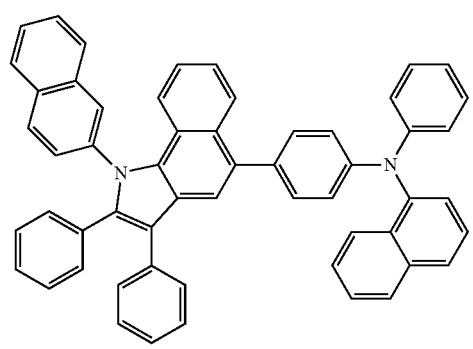
11
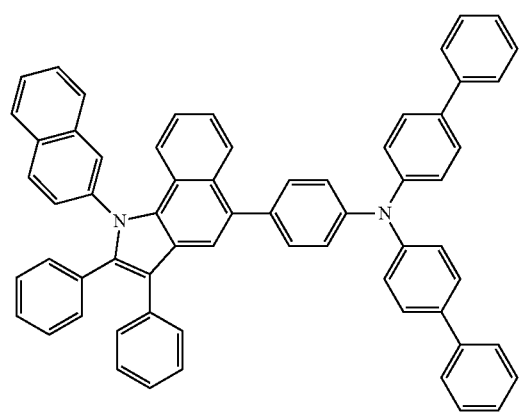
12
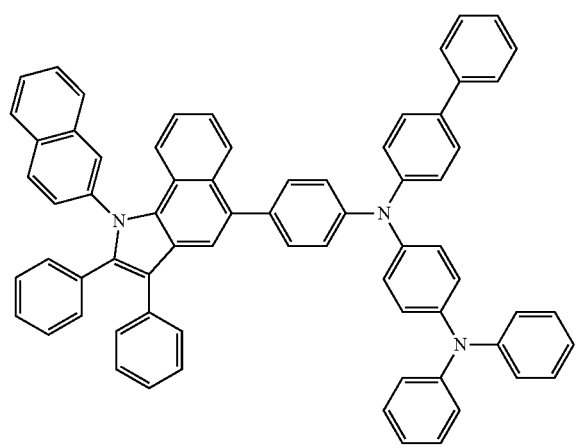

13
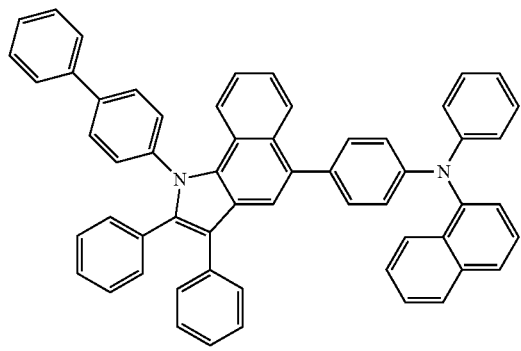
14
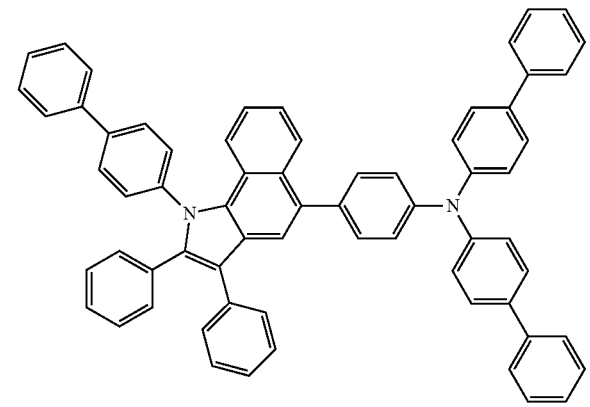
15
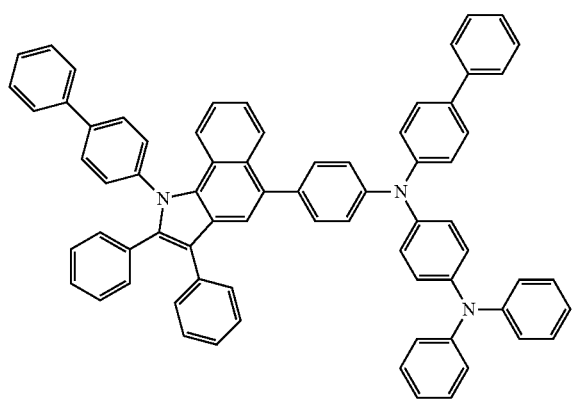
16
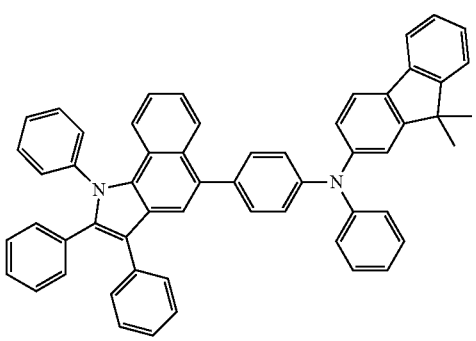
17
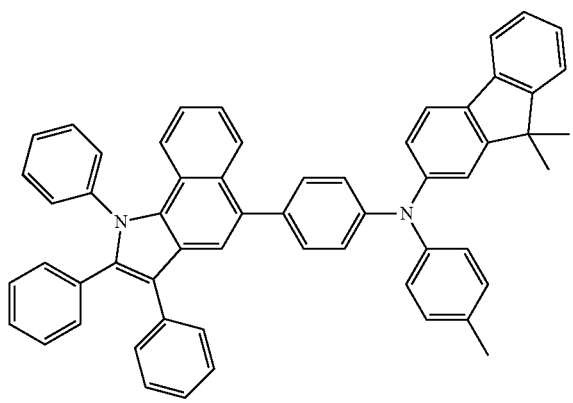
18
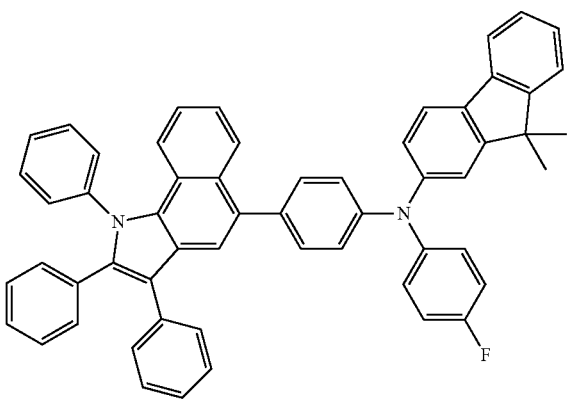

-continued
19
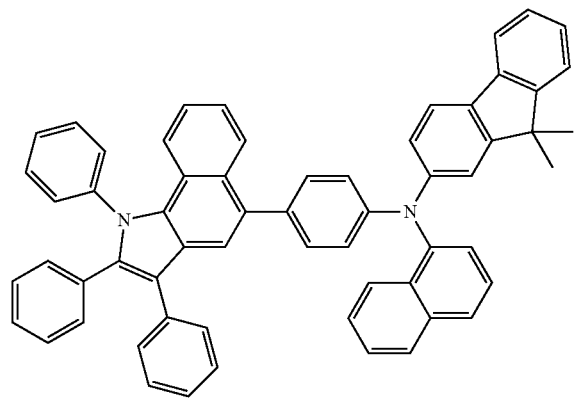
20
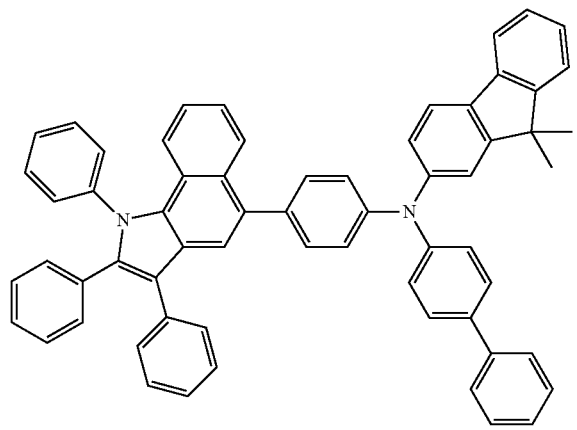
21
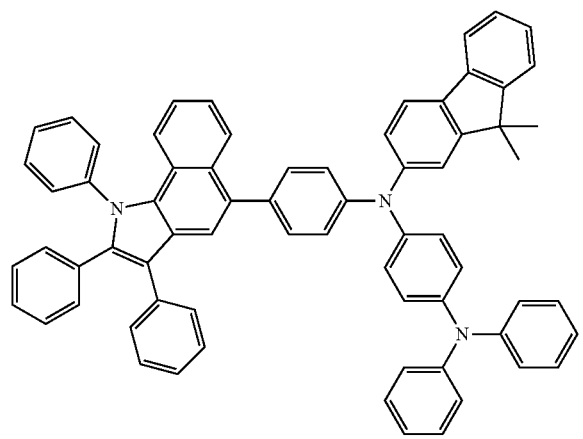
22
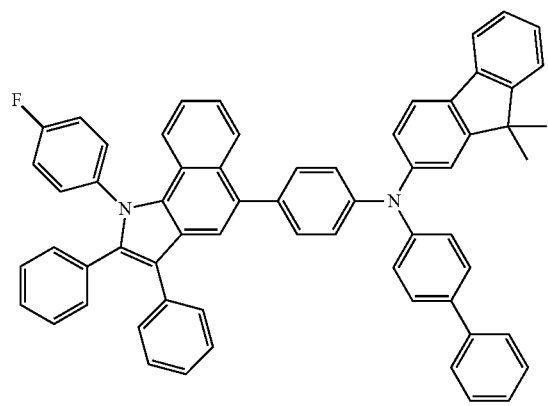
23
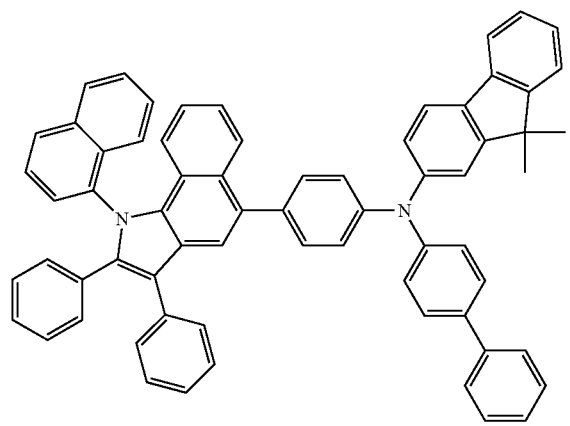
24
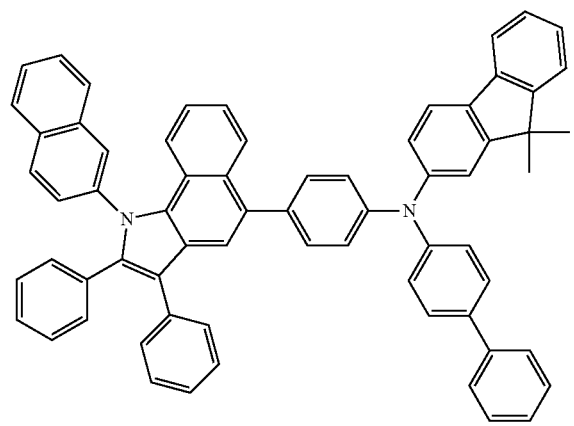

-continued
25
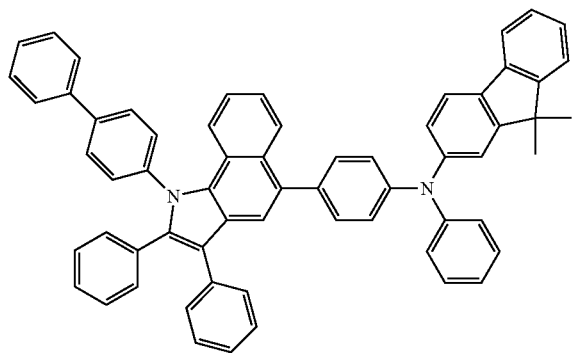
26
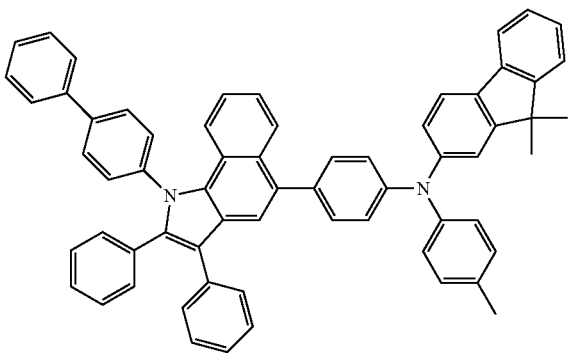
27
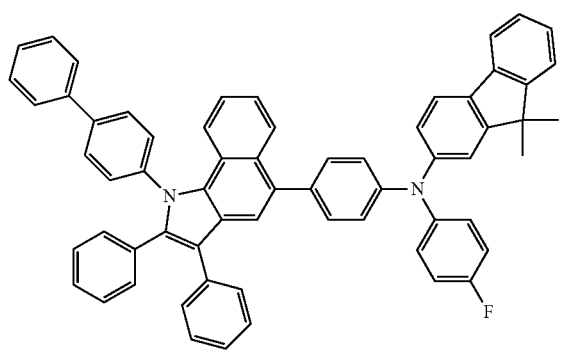
28
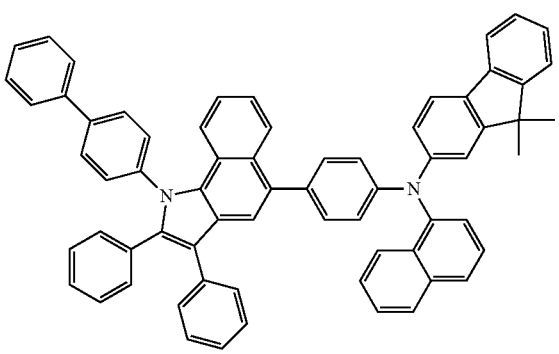
29
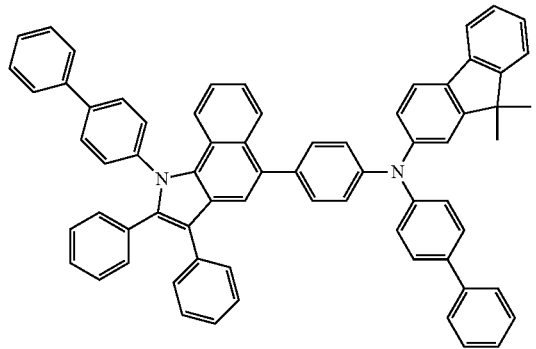
30
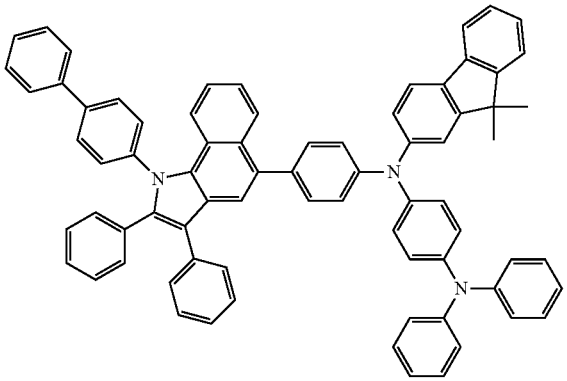
31
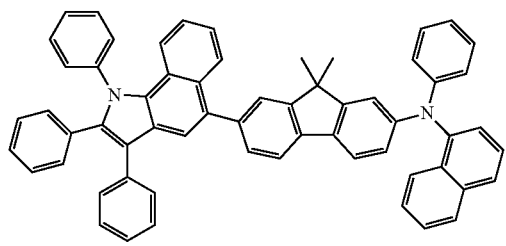
32
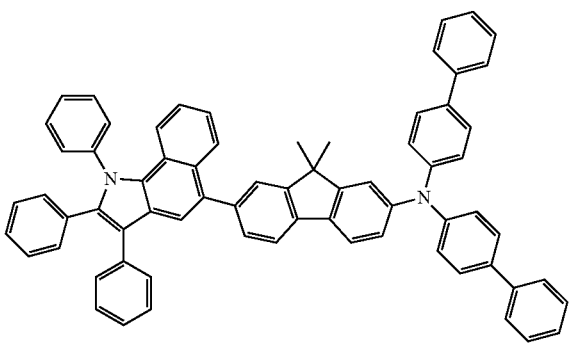

-continued
33
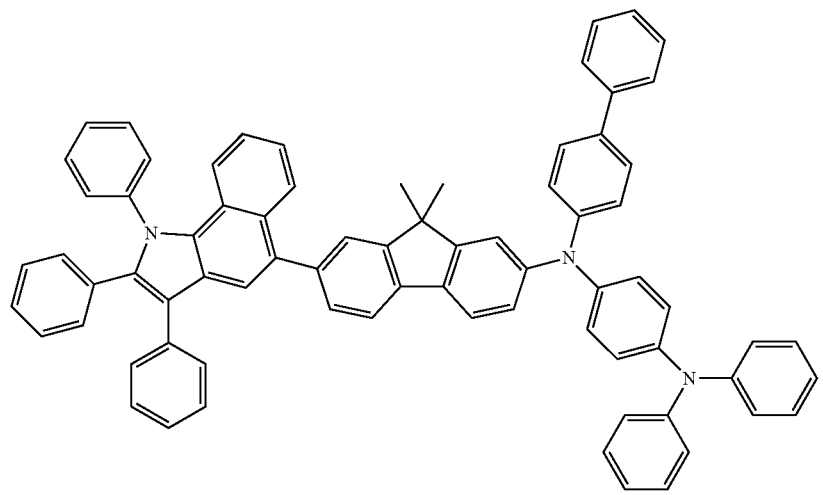
34
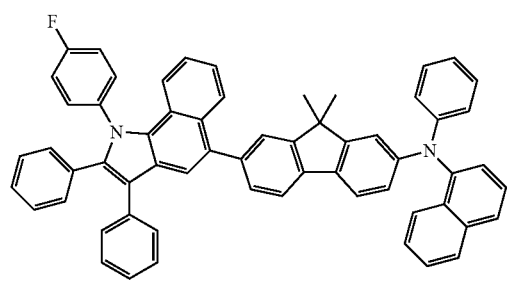
35
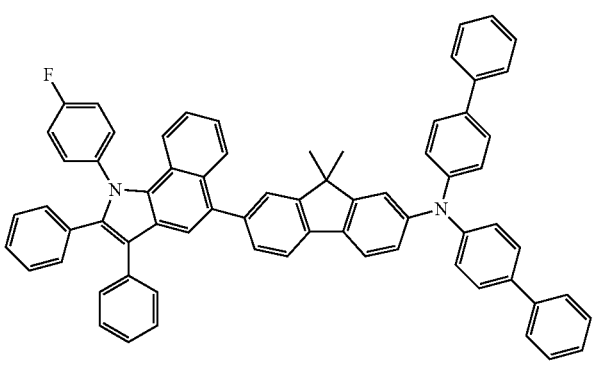
36
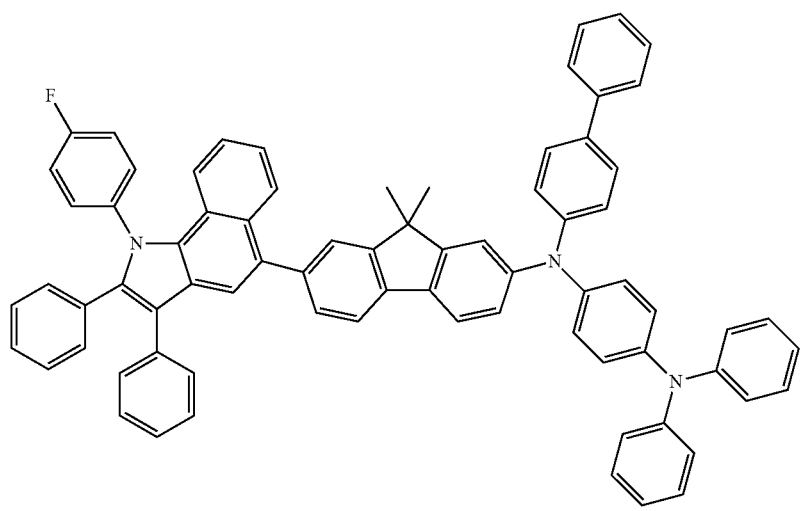

37
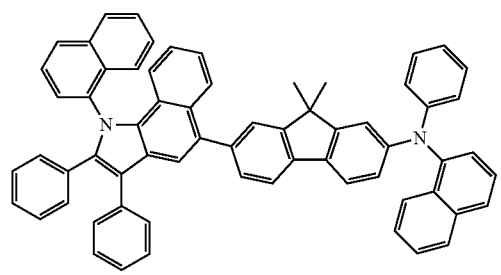
38
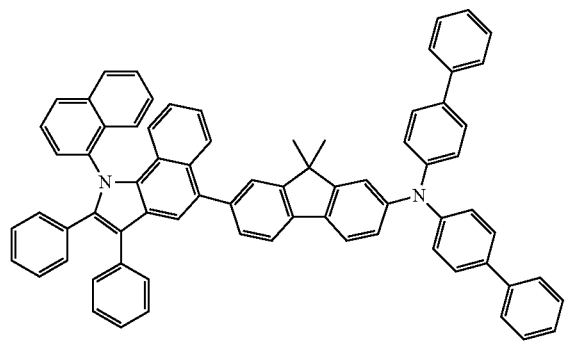
39
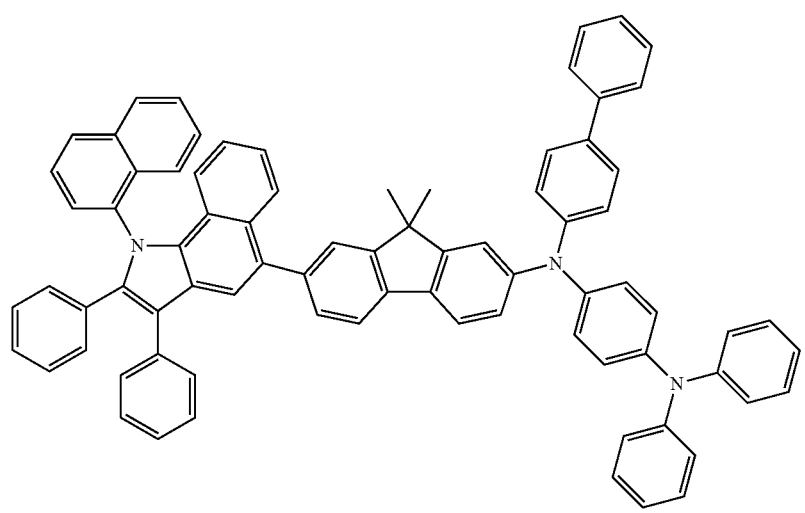
40
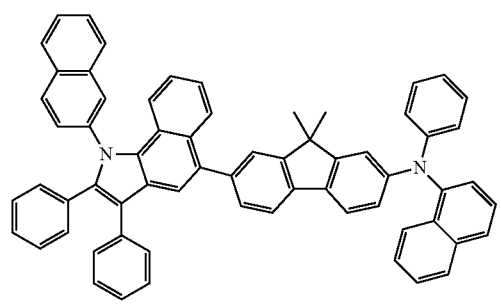
41
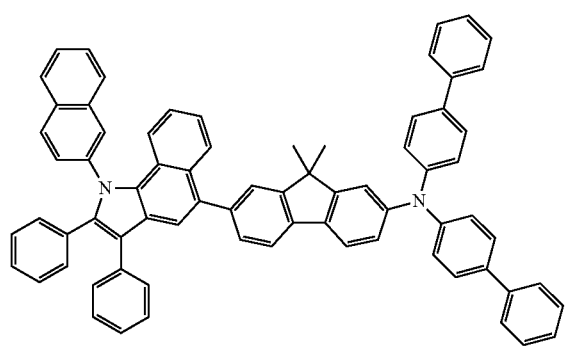

42
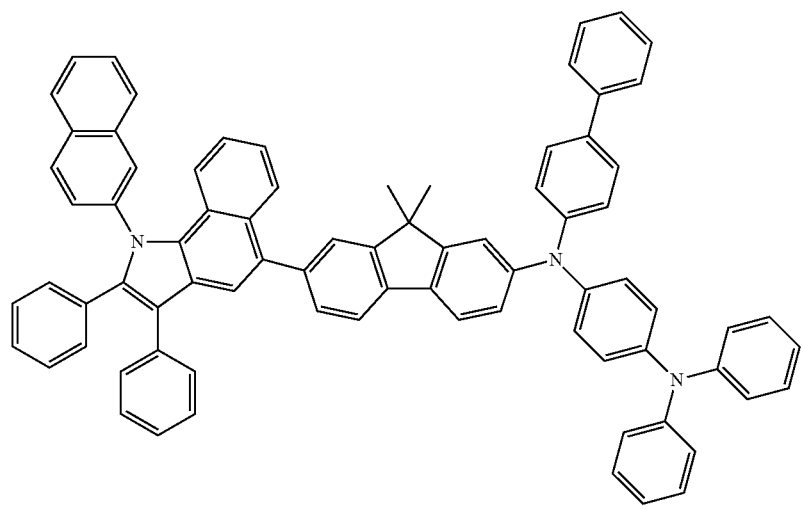
43
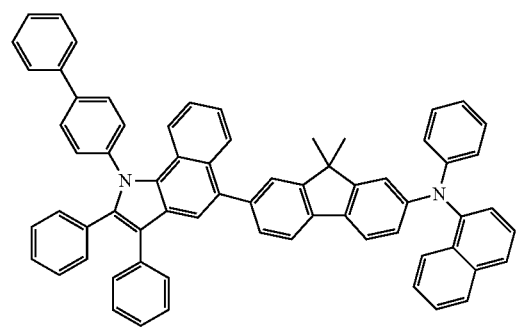
44
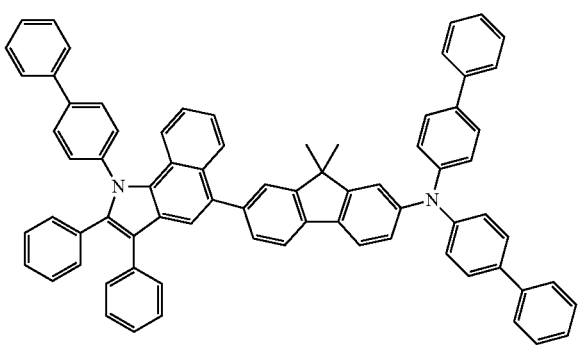
45
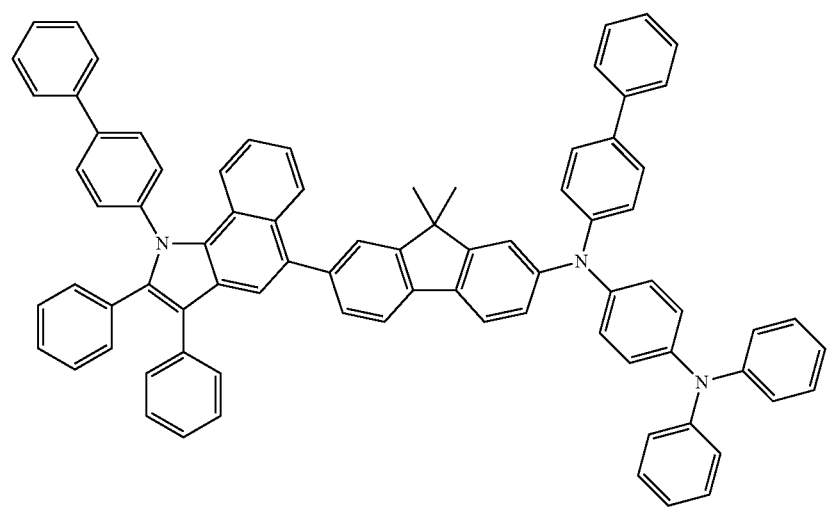

-continued
46
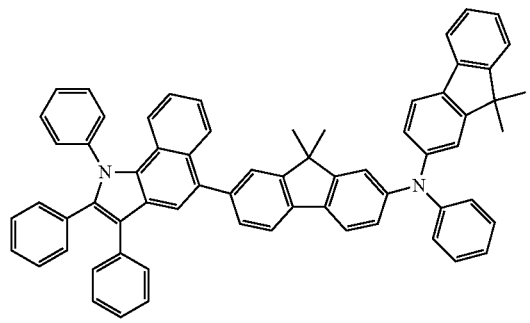
47
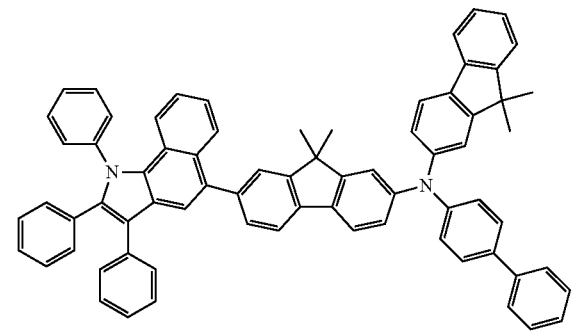
48
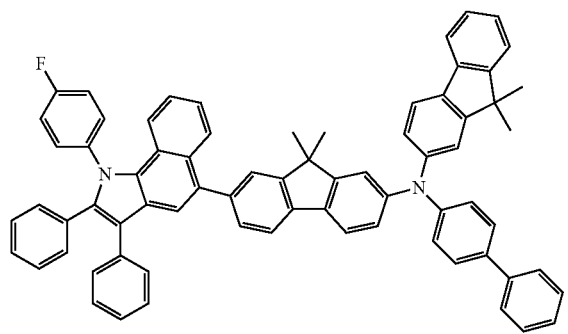
49
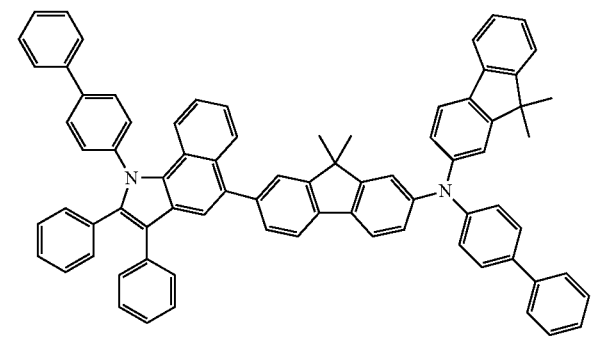
50
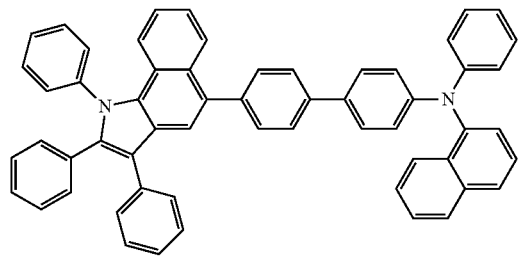
51
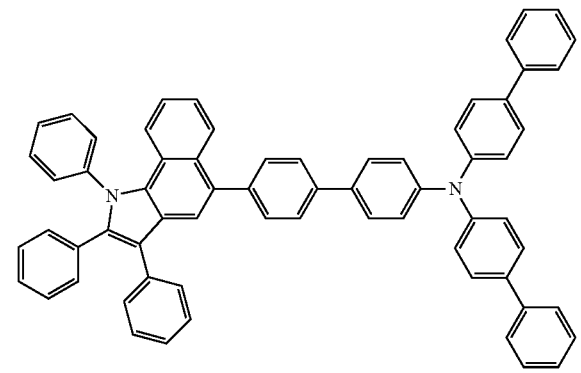
52
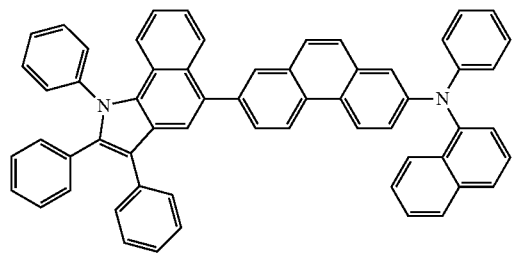
53
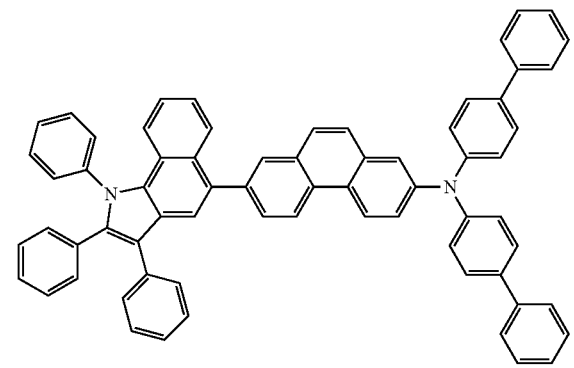

54
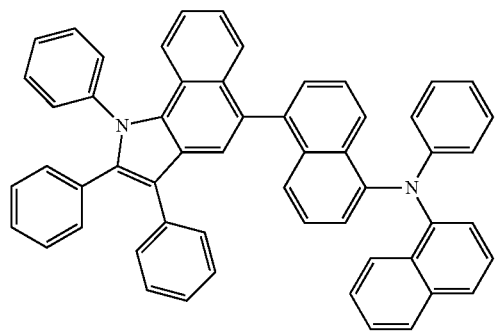
55
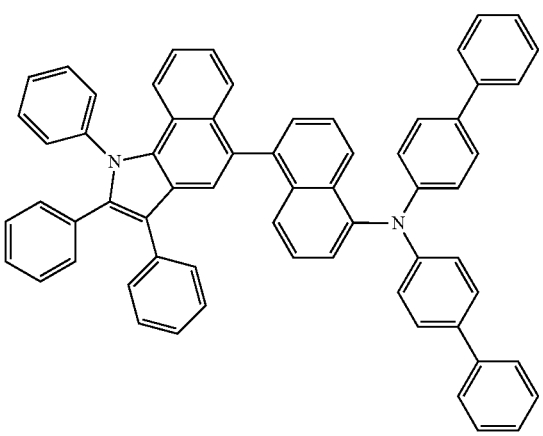
56
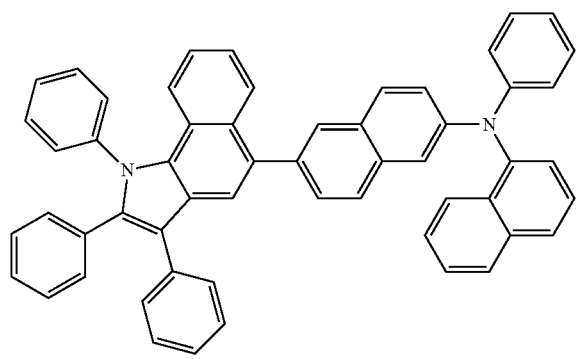
57
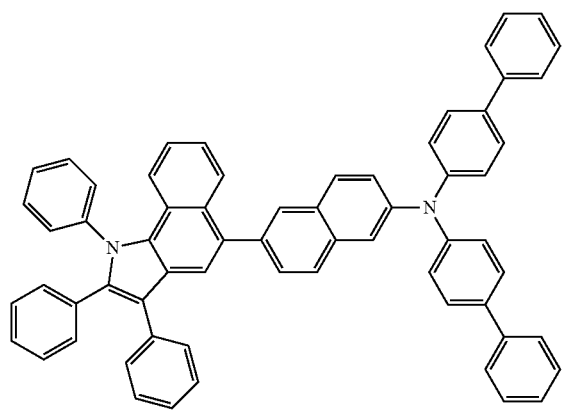
58
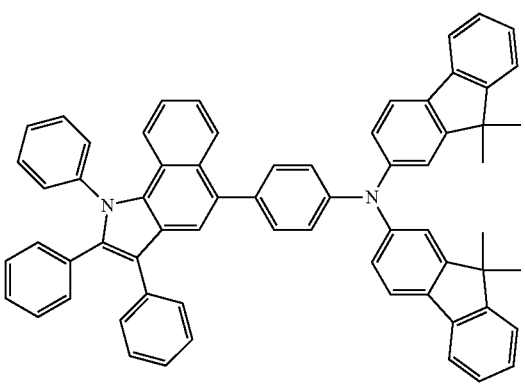

-continued
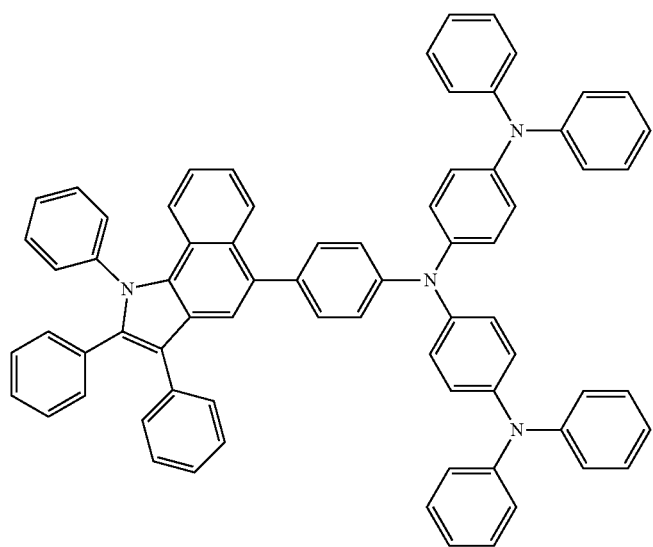
59
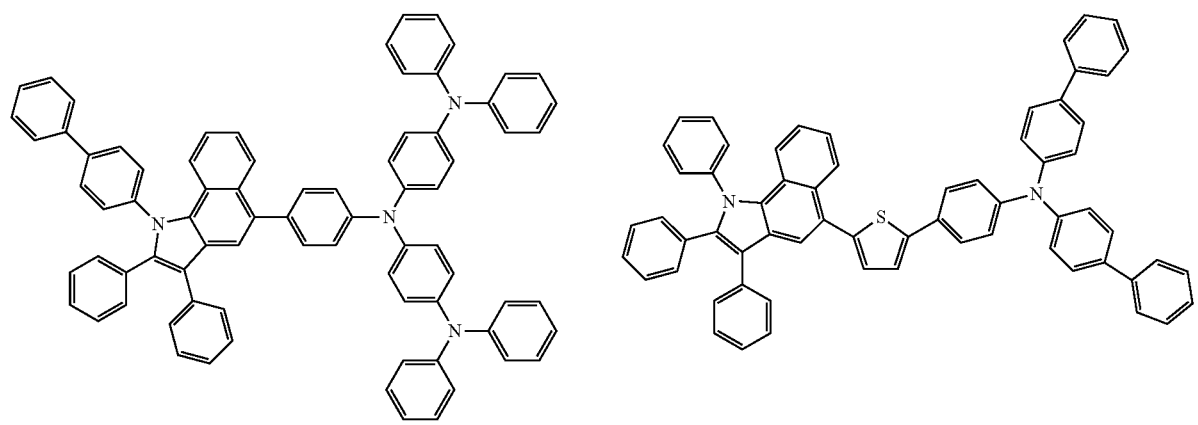
60
61
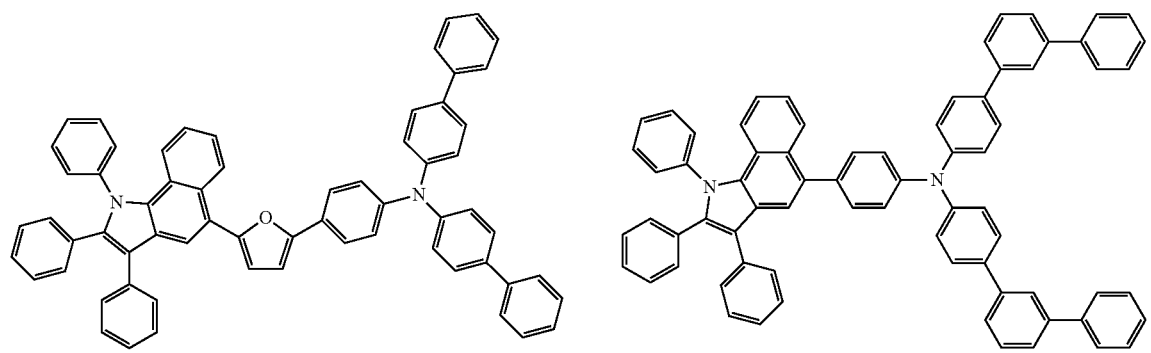
62
63

-continued
64
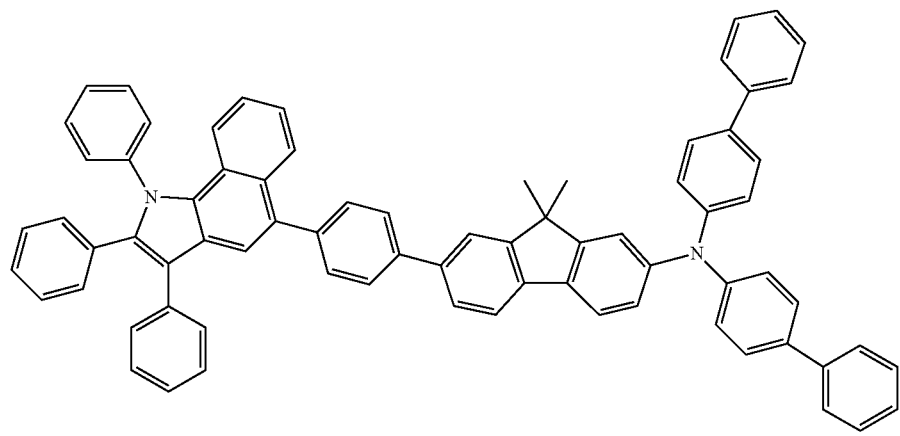
65
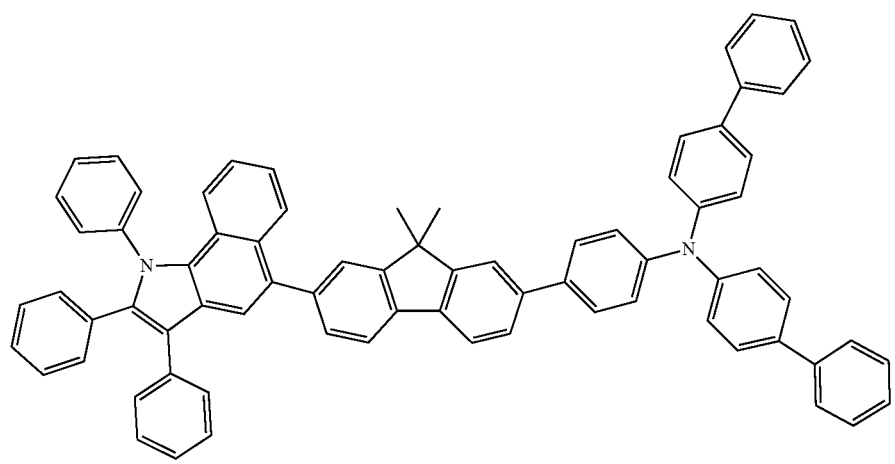
66 67
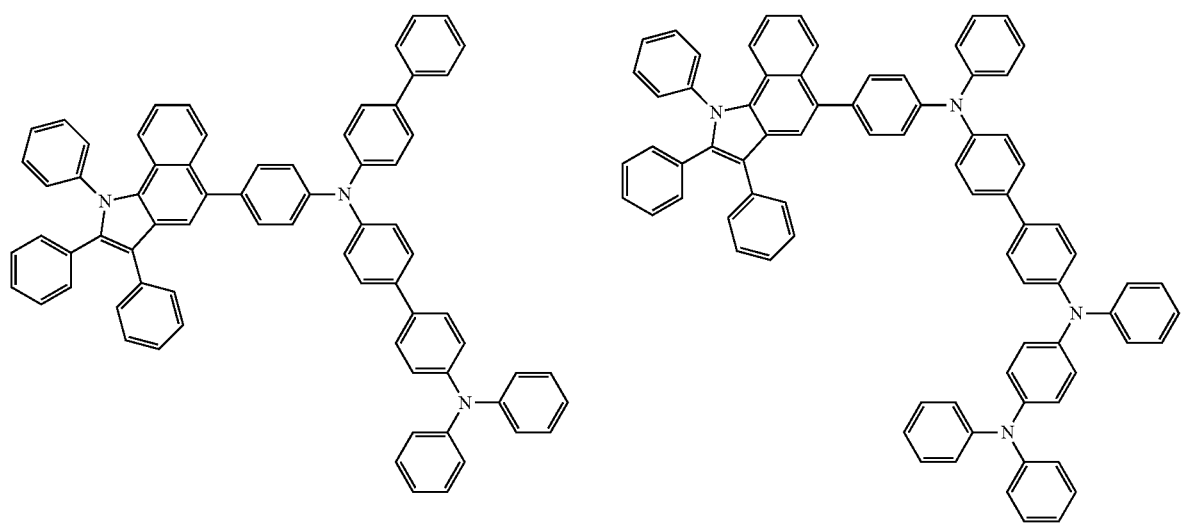

-continued
68
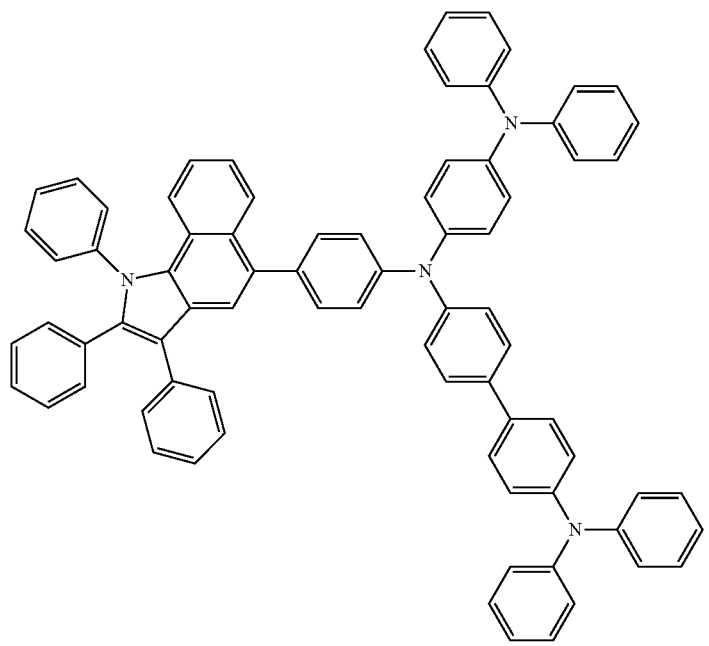
69
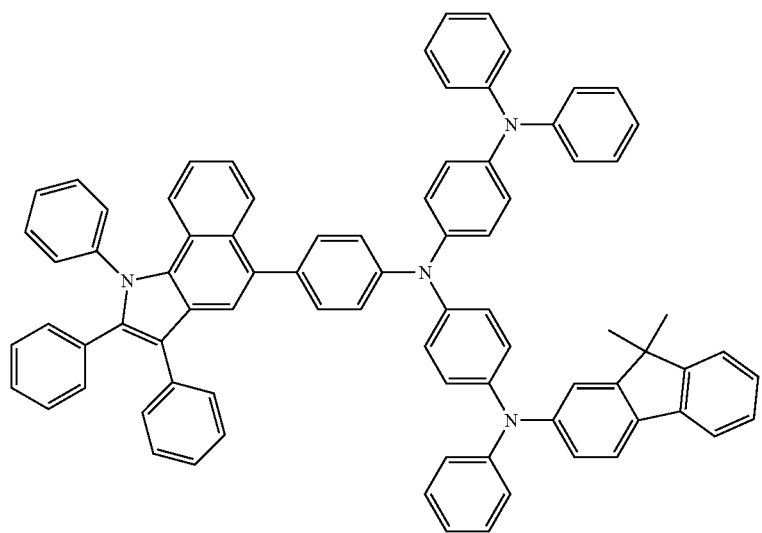
70
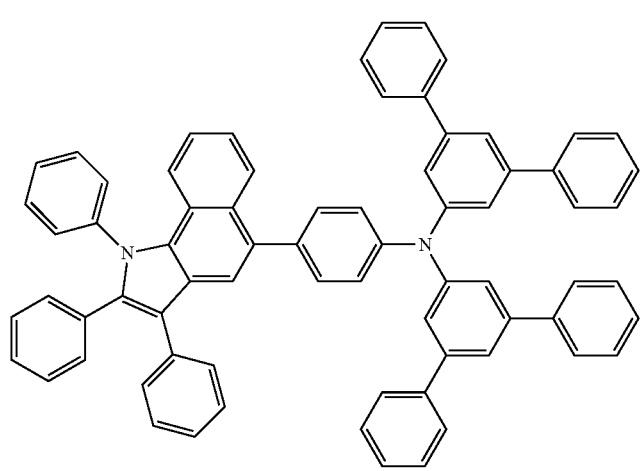

-continued
71
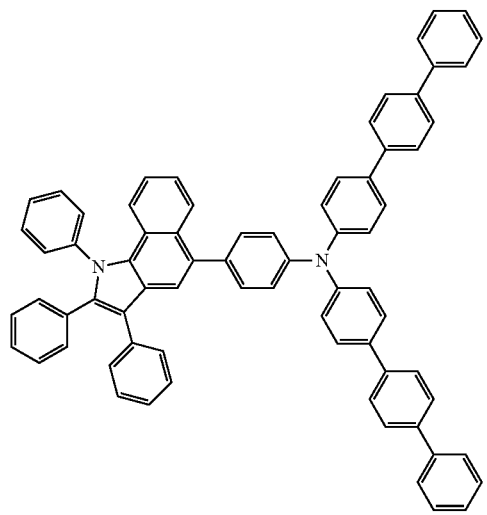
72
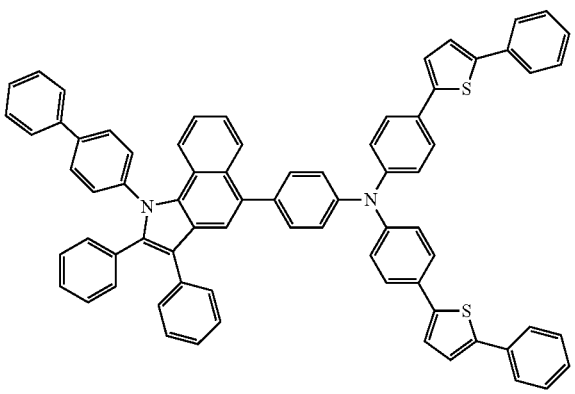
73
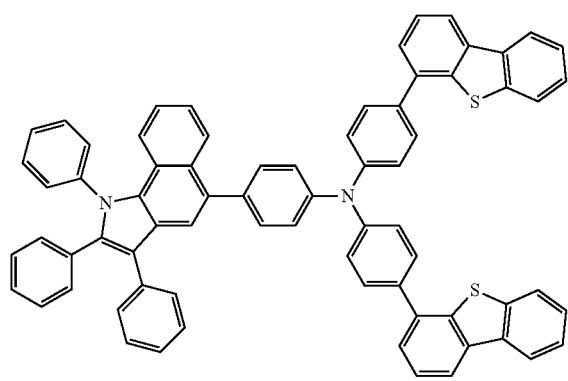
74
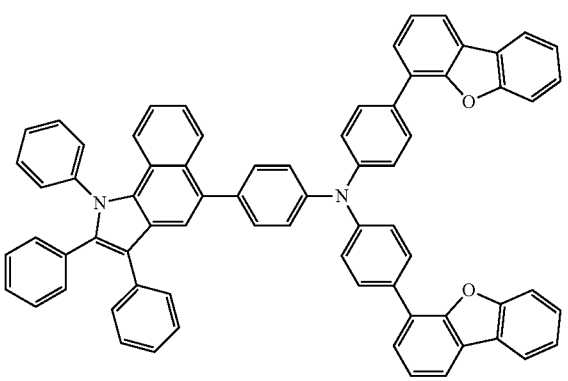
75
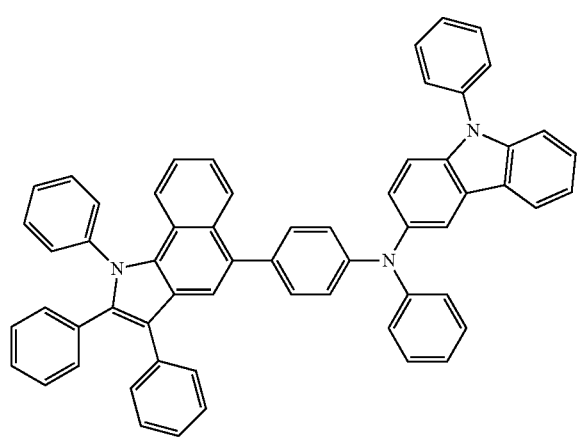
76
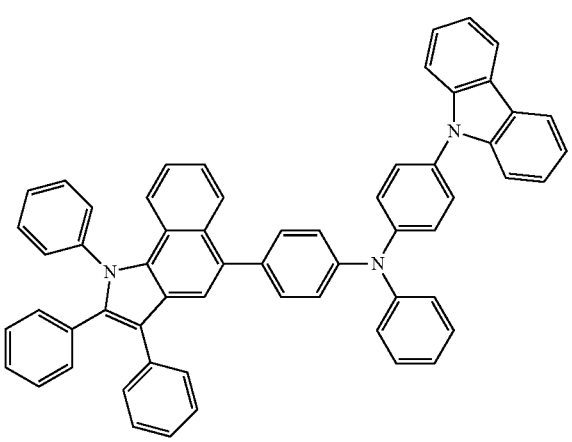

-continued
77
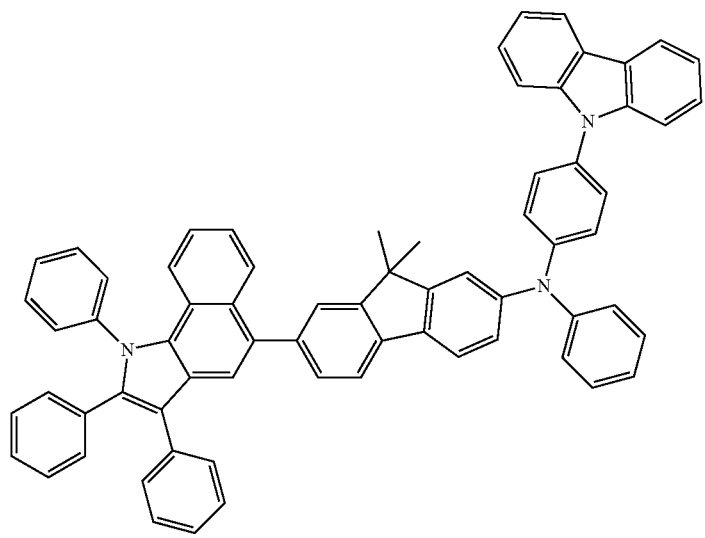
78
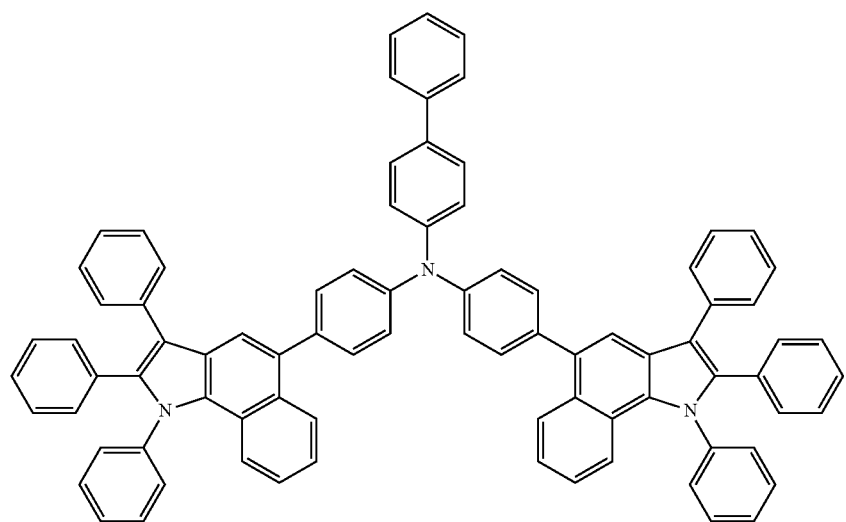
79
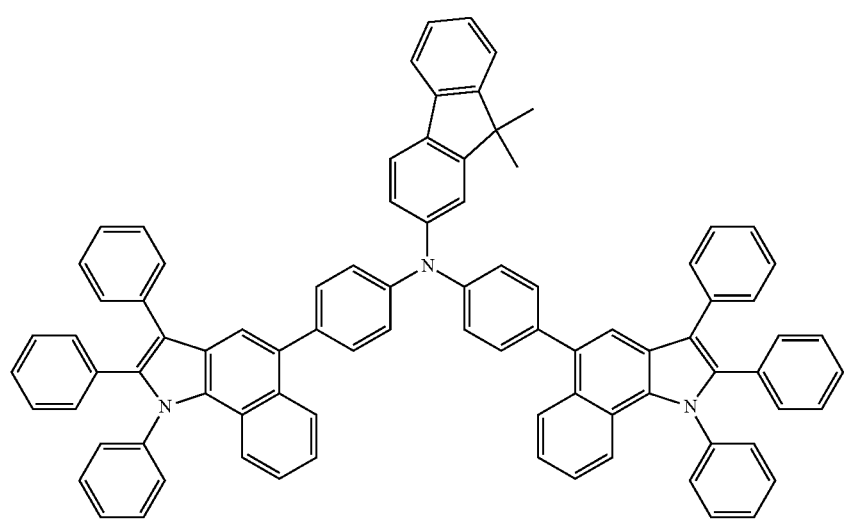

80
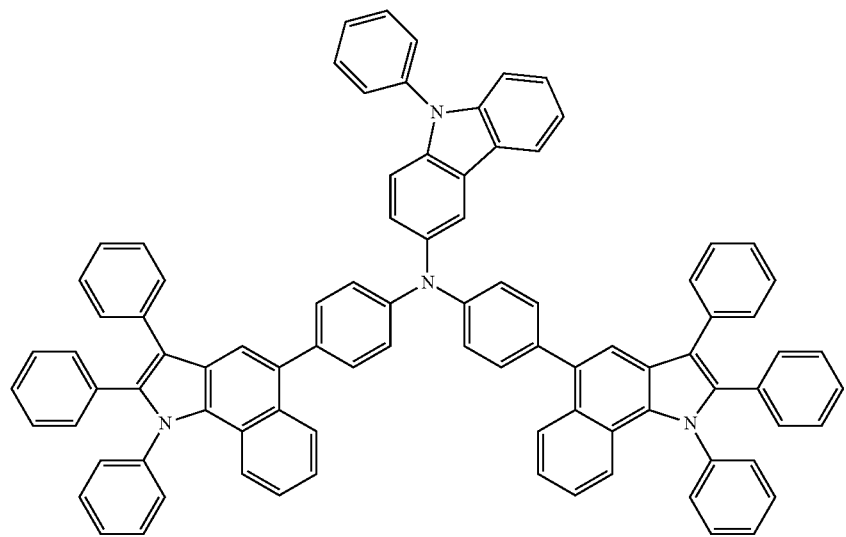
81
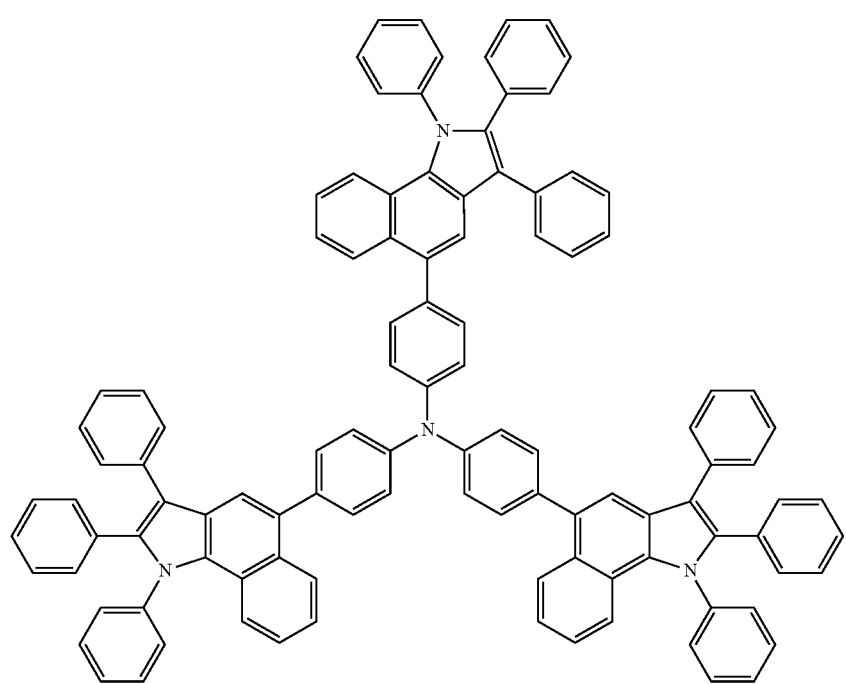

-continued
82
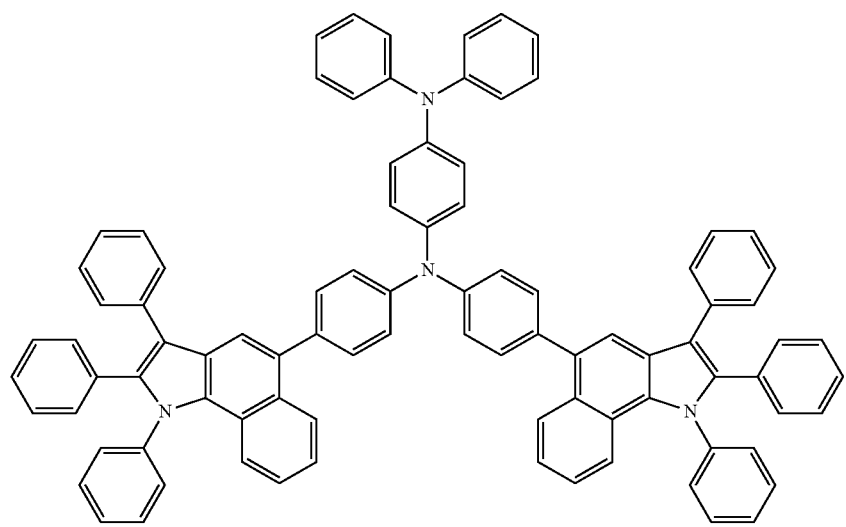
83
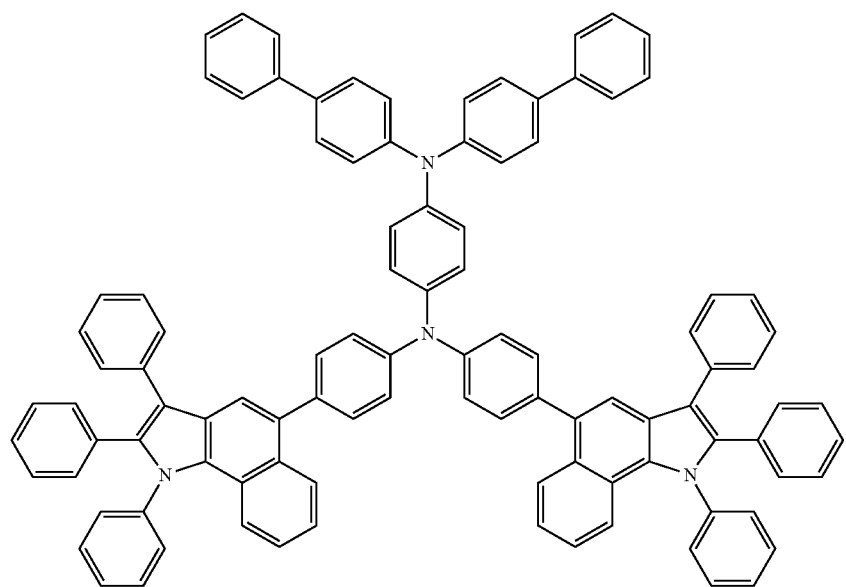
84
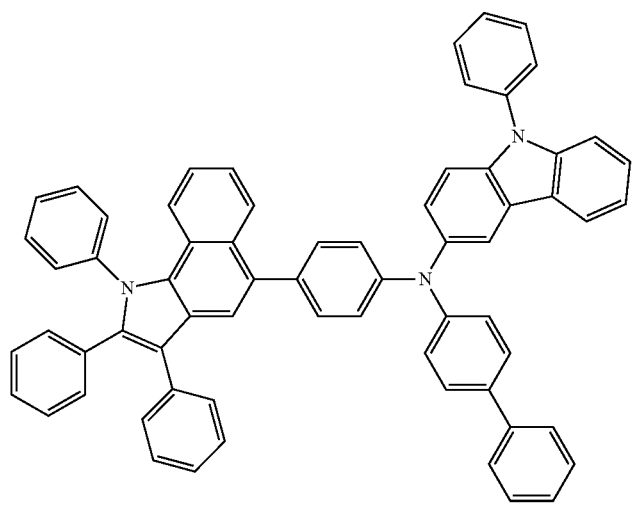

85
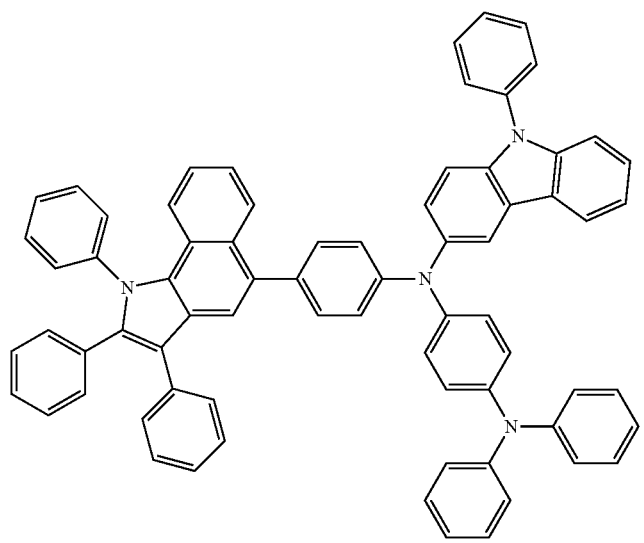
86 87
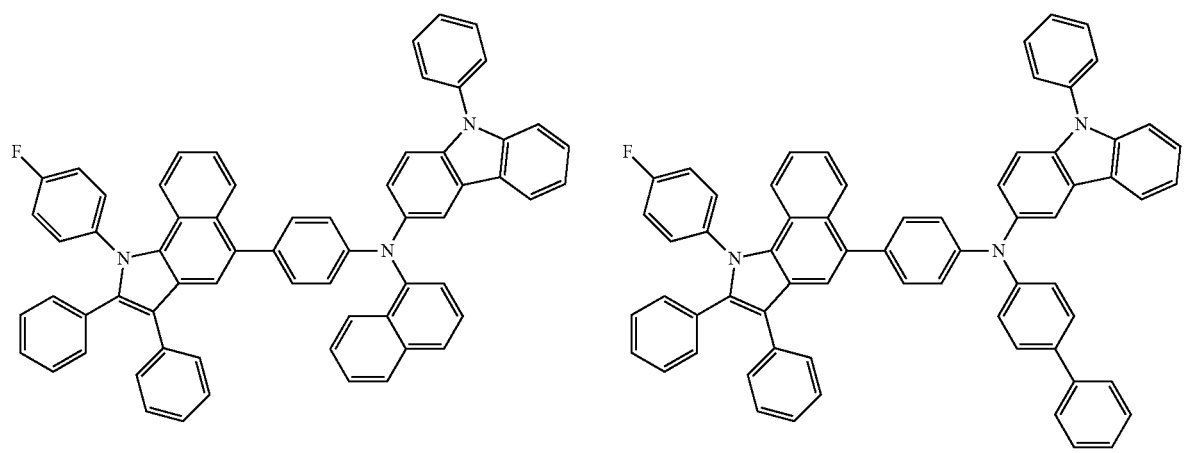
88 89
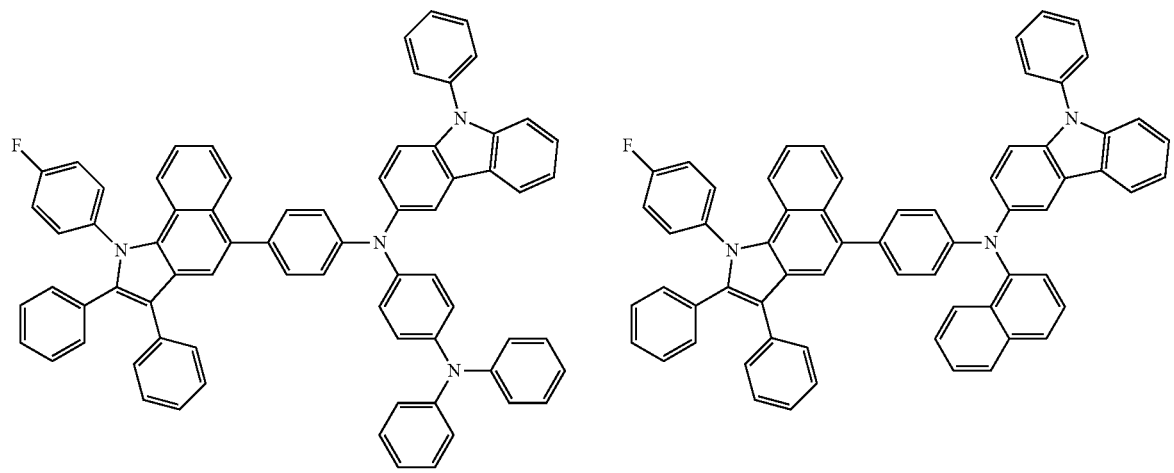

-continued
90
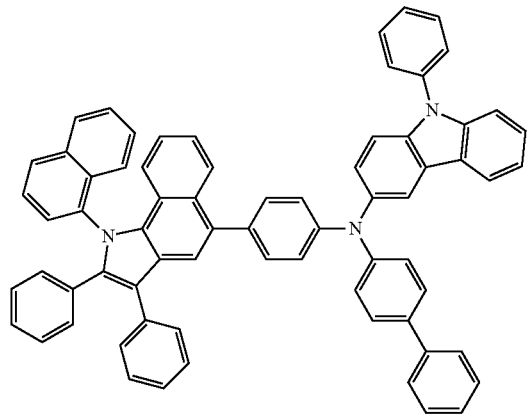
91
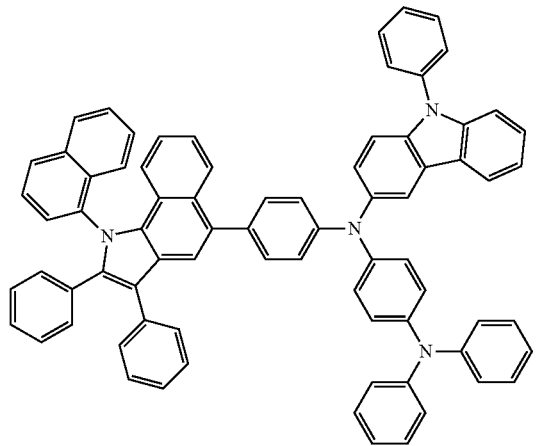
92
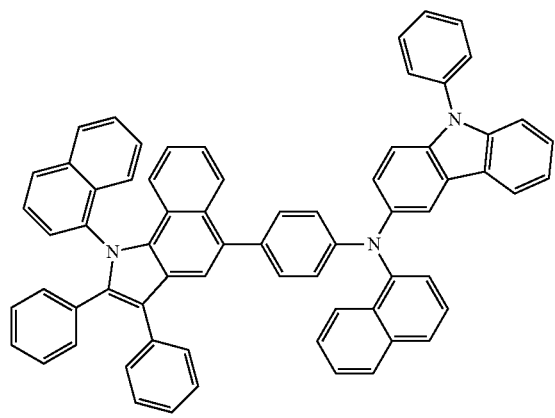
93
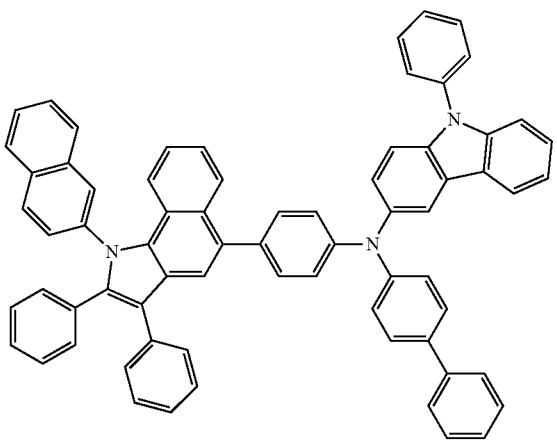
94
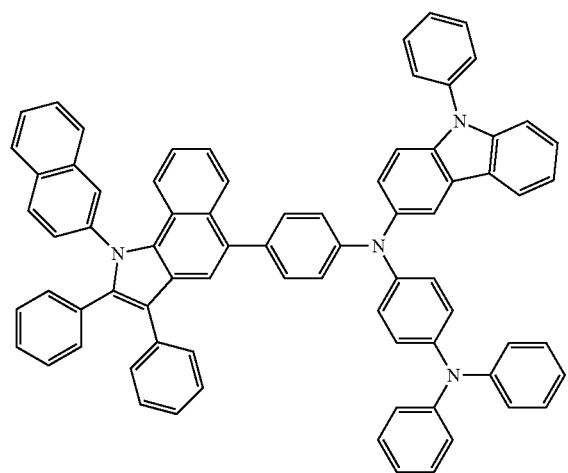
95
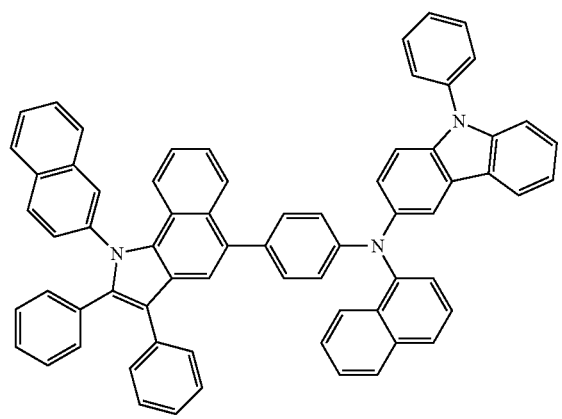

-continued
96
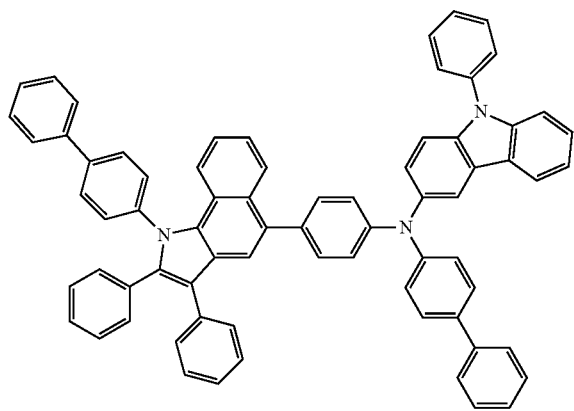
97
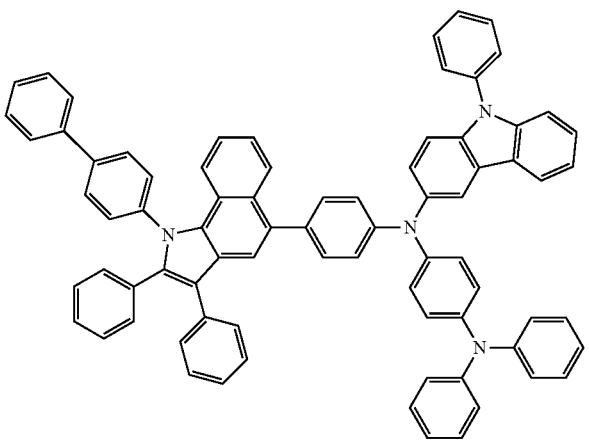
98
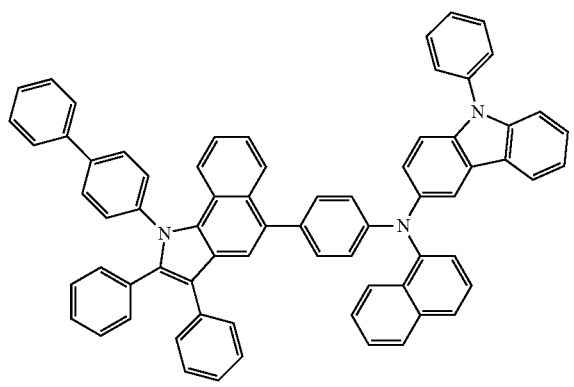
99
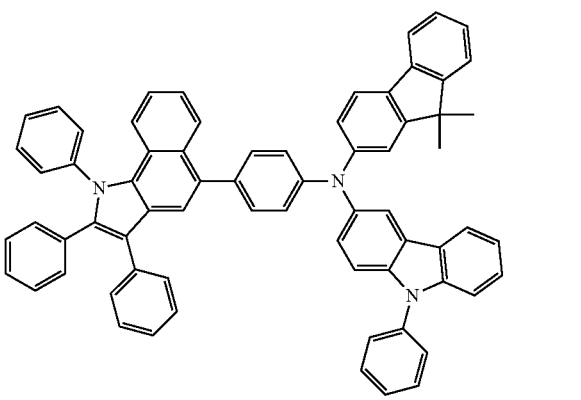
100
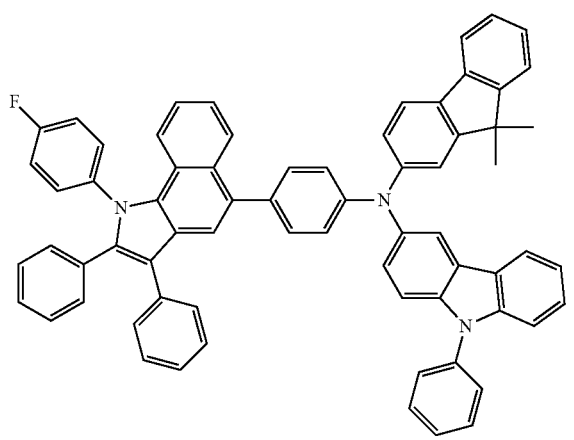
101
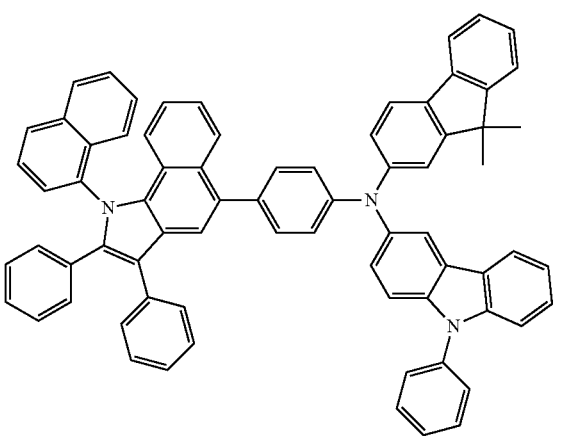

-continued
102
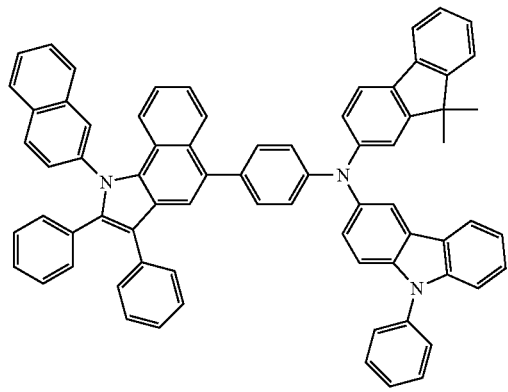
103
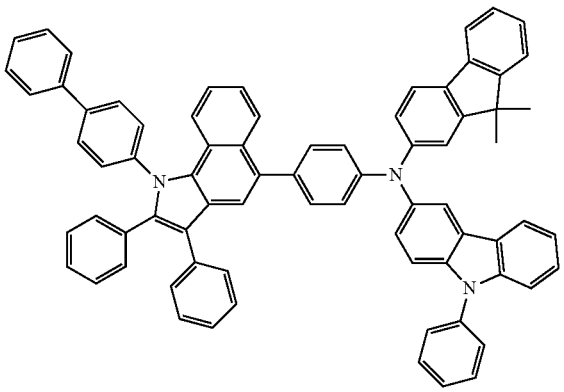
104
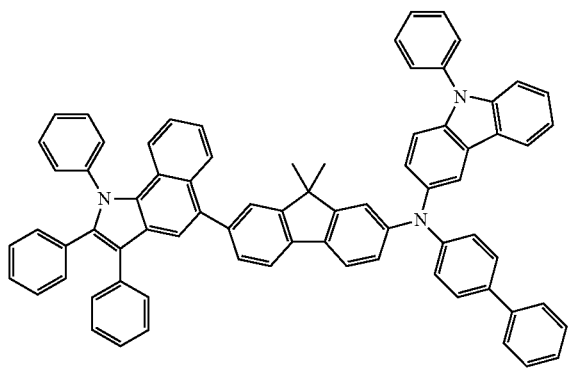
105
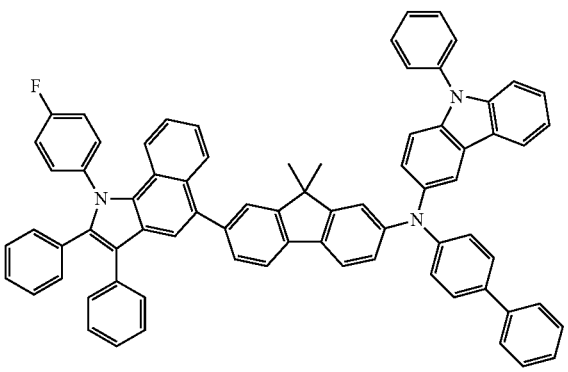
106
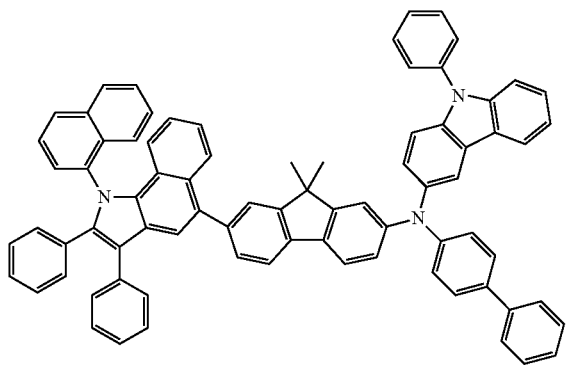
107
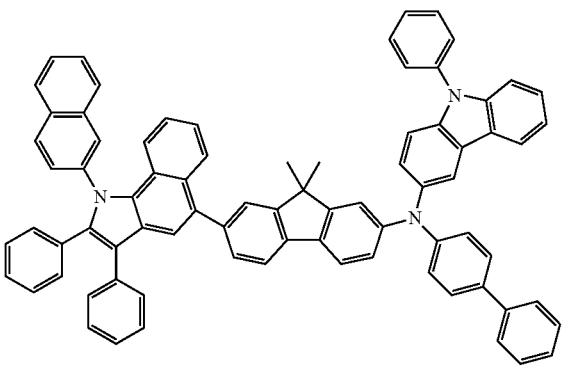
108
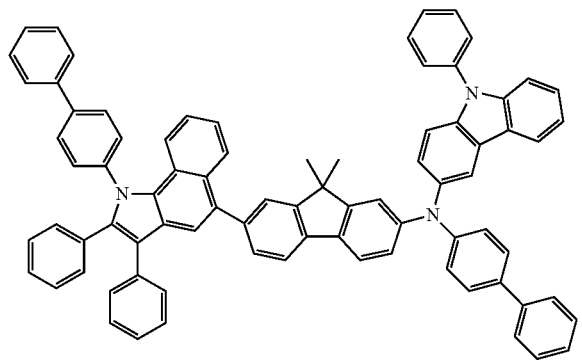
109
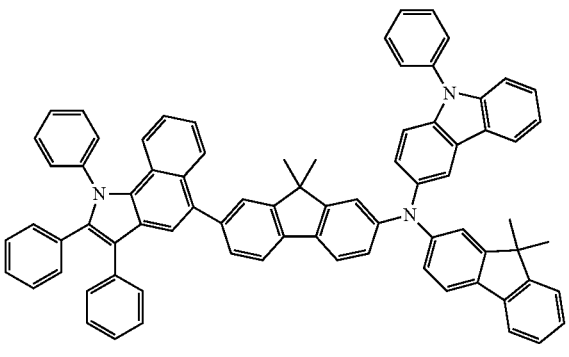

110
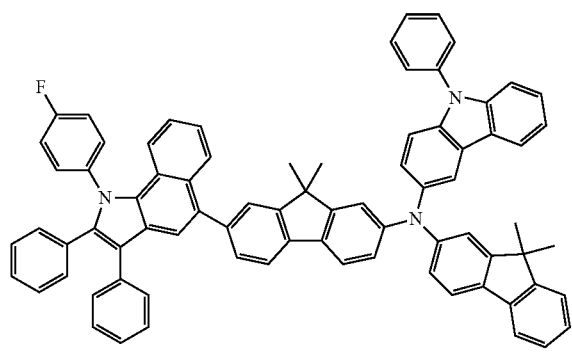
111
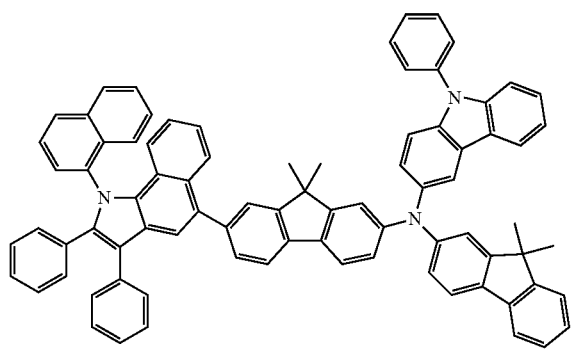
In some embodiments, for example, the amine compound of Formula 1 may be selected from Compound 1, Compound 2, Compound 8, Compound 29, Compound 32, Compound 58, Compound 81, Compound 84, and Compound 99.
1
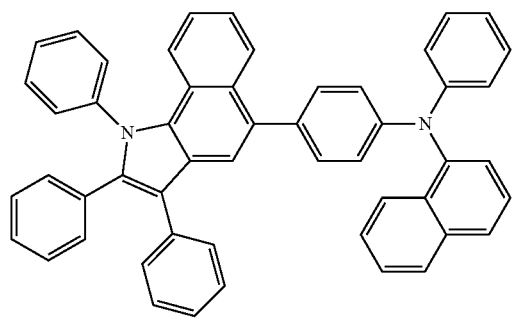
2
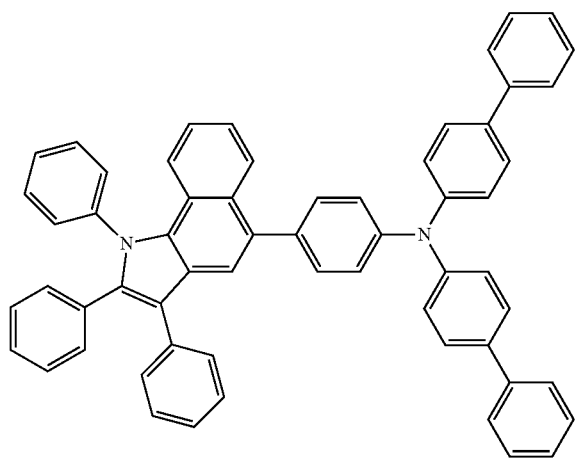
8
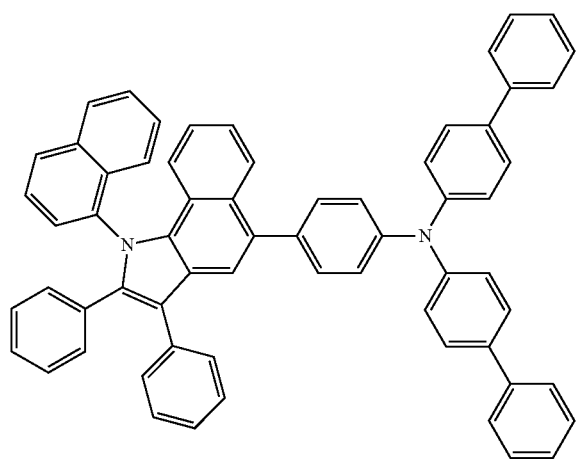
29
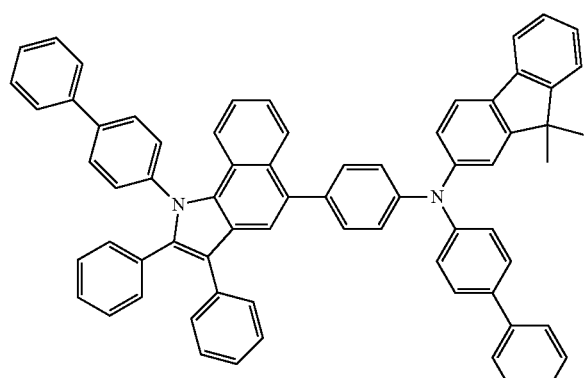

32
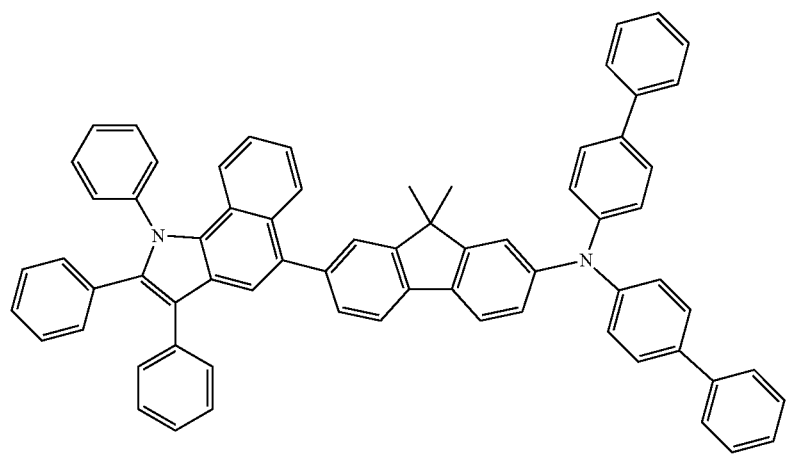
58
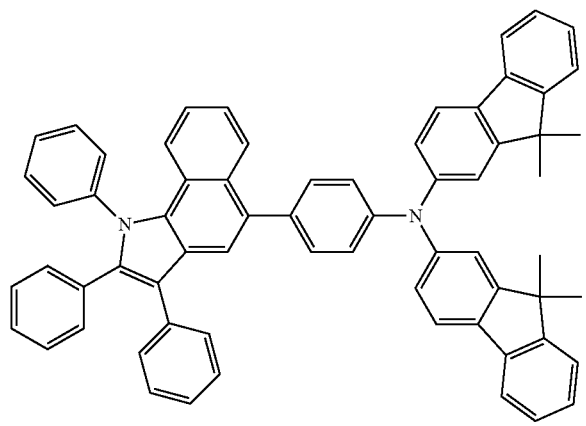
81
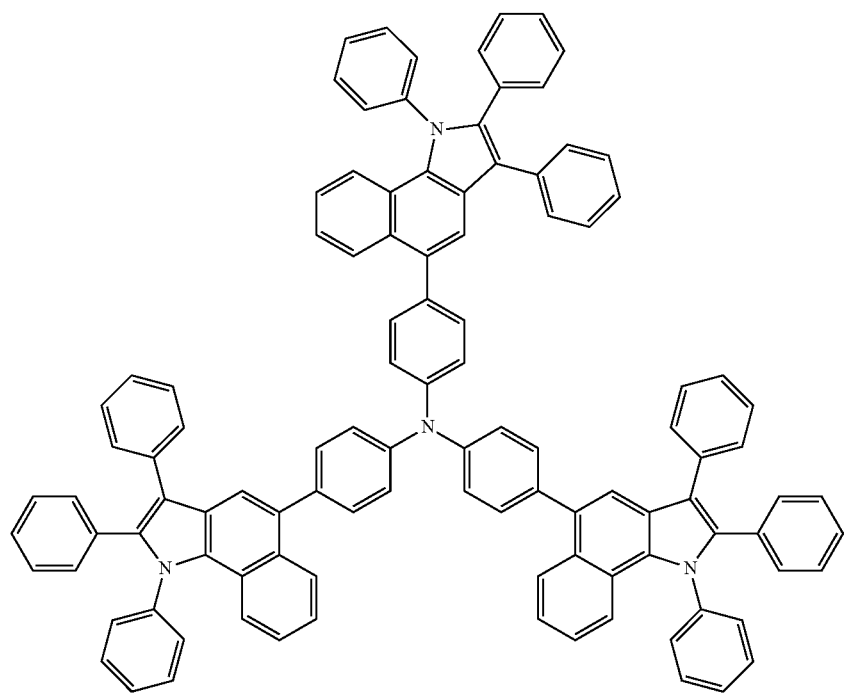

-continued

84

99

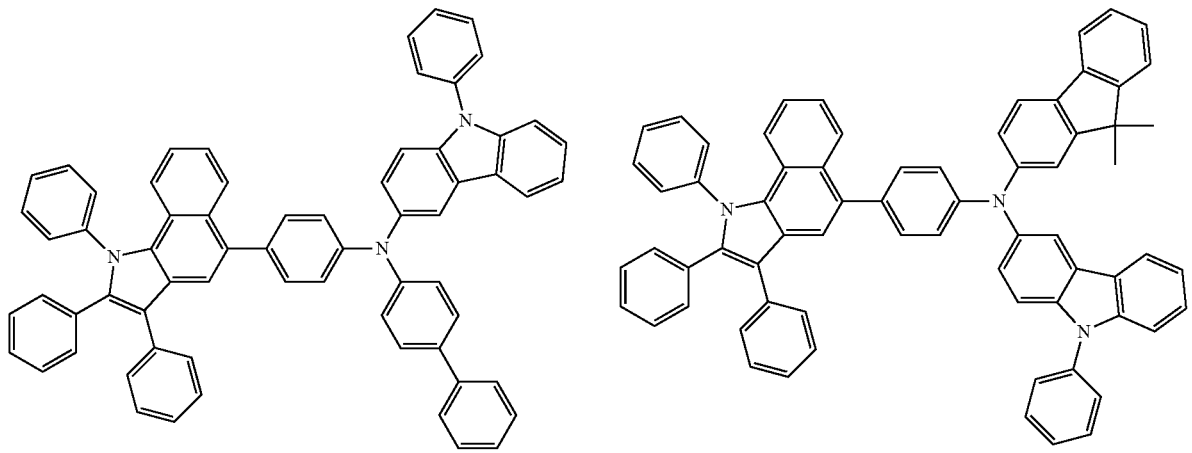

According to some embodiments of the present invention, a method of synthesizing an amine compound of Formula 1 is provided. First, benzophenone hydrazone, sodiumbutoxide, palladium diacetate, and 2-dicyclohexylphosphino-2',4',6'-triisopropylbiphenyl are added to and mixed with the amine compound represented by Formula 7 below, and then the resultant product is heat treated, thereby obtaining a compound represented by Formula 8 below.

Formula 7

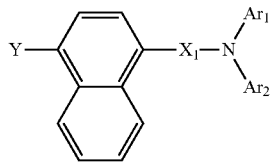

In Formula 7, $X_1$, $Ar_1$, and $Ar_2$ are the same as described above with reference to Formula 1, and Y is a halogen atom such as bromine, iodine, or chloride.

Formula 8

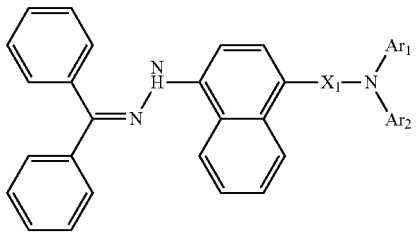

In Formula 8, $X_1$, $Ar_1$, and $Ar_2$ are the same as described above with reference to Formula 1.

The amount of the benzophenone hydrazone may be about 1.05 to about 1.2 moles based on 1 mole of the amine compound represented by Formula 7. The amount of the sodiumbutoxide may be about 1.2 to about 1.5 moles based on 1 mole of the amine compound represented by Formula 7. The amount of the palladium diacetate may be about 0.02 to about 0.05 moles based on 1 mole of the amine compound represented by Formula 7. The amount of the 2-dicyclohexylphosphino-2',4',6'-triisopropylbiphenyl may be about 0.02 to about 0.05 moles based on 1 mole of the amine compound represented by Formula 7.

The heat treatment temperature may be about 80 to about 100° C. If the heat treatment temperature is outside this range, the yield of the compound represented by Formula 8 may be reduced.

Next, p-toluenesulfonic monohydrate, benzylphenylketone, and a solvent are added to the compound represented by Formula 8, and the resultant mixture is heat treated. When the reaction is completed, the reaction product is worked-up, thereby obtaining the amine compound represented by Formula 1.

At this stage, the heat treatment temperature may be about 60 to about 100° C. If the heat treatment temperature is outside this range, the yield of the amine compound represented by Formula 1 may be reduced.

The amount of the p-toluenesulfonic monohydrate may be about 1.5 to about 2.0 moles based on 1 mole of the compound represented by Formula 8, and the amount of the benzylphenylketone may be about 1.5 to about 2.0 moles based on 1 mole of the compound represented by Formula 8.

According to other embodiments of the present invention, an organic luminescence device includes a first electrode, a second electrode, and an organic layer between the first and second electrodes, wherein the organic layer includes the amine compound represented by Formula 1.

The organic layer including the amine compound of Formula 1 may be a hole injection layer or a hole transport layer, or a single layer having both hole injection and hole transport capabilities. For example, the organic layer including the amine compound of Formula 1 may be a hole transport layer. In addition, the amine compound of Formula 1 may also be used as a host for fluorescence or phosphorescence organic light emitting device.

The first electrode may be an anode and the second electrode may be a cathode. Alternatively, the first electrode may be a cathode and the second electrode may be an anode.

The organic luminescence device according to embodiments of the present invention may have various organic EL structures. For example, the organic EL device have a bottom emission structure including an anode as a first electrode, a hole injection layer (HIL), a hole transport layer (HTL), an emitting layer (EML), an electron transport layer (ETL), an electron injection layer (EIL), and a cathode as a second electrode (as illustrated in FIG. 1). Alternatively, the organic EL device may have a front emission structure. If desired and/or necessary, one or more intermediate layers may be further formed.

For example, the organic luminescence device according to the present embodiment may have a first electrode/hole injection layer/emitting layer/second electrode structure, a first electrode/hole injection layer/hole transport layer/emitting layer/electron transport layer/second electrode structure, or a first electrode/hole injection layer/hole transport layer/emitting layer/electron transport layer/electron injection layer/ second electrode structure. The organic luminescence device according to the present embodiment may also have a first electrode/single layer having hole injection and hole transport capabilities/emitting layer/electron transport layer/second electrode structure, or a first electrode/single layer having hole injection and hole transport capabilities/emitting layer/ electron transport layer/electron injection layer/second electrode structure.

The amine compounds represented by Formula 1 have good hole injection characteristics and hole transport characteristics and thus are useful as hole transport materials. In addition, the amine compounds represented by Formula 1 may also be used as a host material for emission layers of blue, green, and red fluorescent and phosphorescent devices.

According to embodiments of the present invention, the organic luminescence device may include an organic layer including a hole injection layer (HIL), a hole transport layer (HTL), and an emitting layer (EML), wherein the HIL or the HTL includes the amine compound represented by Formula 1 and the EML includes an arylamine compound.

According to other embodiments of the present invention, the organic luminescence device may include an organic layer including a hole injection layer (HIL), a hole transport layer (HTL), and an emitting layer (EML), wherein the HIL or the HTL includes the amine compound represented by Formula 1 and the EML includes a styryl compound.

According to still other embodiments of the present invention, the organic luminescence device may include an organic layer which includes a hole injection layer (HIL), a hole transport layer (HTL), and an EML including a green emitting layer, a blue emitting layer, a red emitting layer, and a white emitting layer, wherein the HIL or the HTL includes the amine compound represented by Formula 1 and at least one of the green emitting layer, the blue emitting layer, the red emitting layer, and the white emitting layer includes a phosphorescent compound.

According to other embodiments of the present invention, the organic luminescence devices described above include at least one layer formed by wet-etching, where the at least one layer includes the amine compound represented by Formula 1.

The organic luminescence devices according to embodiments of the present invention may be manufactured using any of various suitable methods.

The organic luminescence device according to embodiments of the present invention may be used in various types of flat panel display devices, for example, passive matrix organic luminescence display devices or active matrix organic luminescence display devices. When the organic luminescence device is used in an active matrix organic luminescence display device, a first electrode disposed on a substrate may be electrically connected to a source electrode or a drain electrode of a thin film transistor as a pixel electrode. In addition, the organic luminescence device according to the embodiments of the present invention may also be used in flat panel display devices that display images in two directions.

According to embodiments of the present invention, an organic luminescence device and a method of manufacturing the same are provided. FIG. 1 illustrates the structure of an organic luminescence device according to some embodiments of the present invention. Referring to FIG. 1, an organic layer is first formed on a first electrode. The first electrode may be a reflective electrode or a transparent electrode. The first electrode may include a highly conductive metal such as lithium (Li), magnesium (Mg), aluminum (Al), aluminum-lithium (Al—Li), potassium (Ca), magnesium-indium (Mg—In), magnesium-silver (Mg—Ag), potassium (Ca)-aluminum (Al), aluminum (Al)-indium tin oxide (ITO), ITO, or indium zinc oxide (IZO). The first electrode may be an anode or a cathode.

The organic layer may have a stacked structure including at least one layer selected from a hole injection layer, a hole transport layer, a buffer layer, an electron blocking layer, an emitting layer, a hole blocking layer, an electron transport layer, and an electron injection layer.

FIG. 1 illustrates an organic layer having a stacked structure formed by sequentially forming a HIL, a HTL, an EML, an ETL, and an EIL.

The HIL may be formed on the first electrode using any of various methods, such as vacuum deposition, spin coating, casting, or Langmuir Blodgett (LB) deposition.

If the HIL is formed by vacuum deposition, the deposition conditions may differ according to the compound selected for preparing the target layer, the target layer structure, and the thermal characteristics of the target layer. For example, the deposition temperature may be about 100 to about 500° C., the degree of vacuum may be about $10^{-8}$ to about $10^{-3}$ torr, and the deposition speed may be about 0.01 to about 100 Å/sec.

If the HIL is formed using spin coating, the coating conditions may differ according to the compound selected for preparing the target layer, the target layer structure, and the thermal characteristics of the target layer. For example, the coating speed may be about 2000 rpm to about 5000 rpm and the temperature at which the solvent is removed after coating may be about 80° C. to about 200° C.

The HIL may include the amine compound represented by Formula 1 described above. Alternatively, the HIL material may be any known hole injection material. Nonlimiting examples of suitable HIL materials include phthalocyanine compounds (such as copper phthalocyanine), 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DESA), poly(3,4-ethylenedioxythiophene)/poly (4-styrenesulfonate) (PEDOT/PSS), polyaniline/camphor sulfonicacid (Pani/CSA), or (polyaniline)/poly(4-styrenesulfonate) (PANI/PSS).

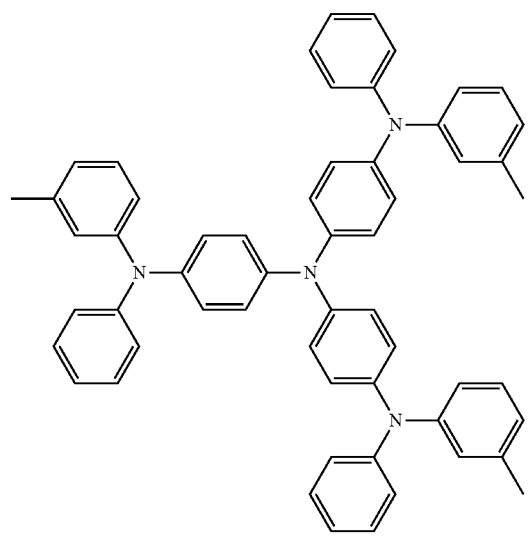

m-MTDATA

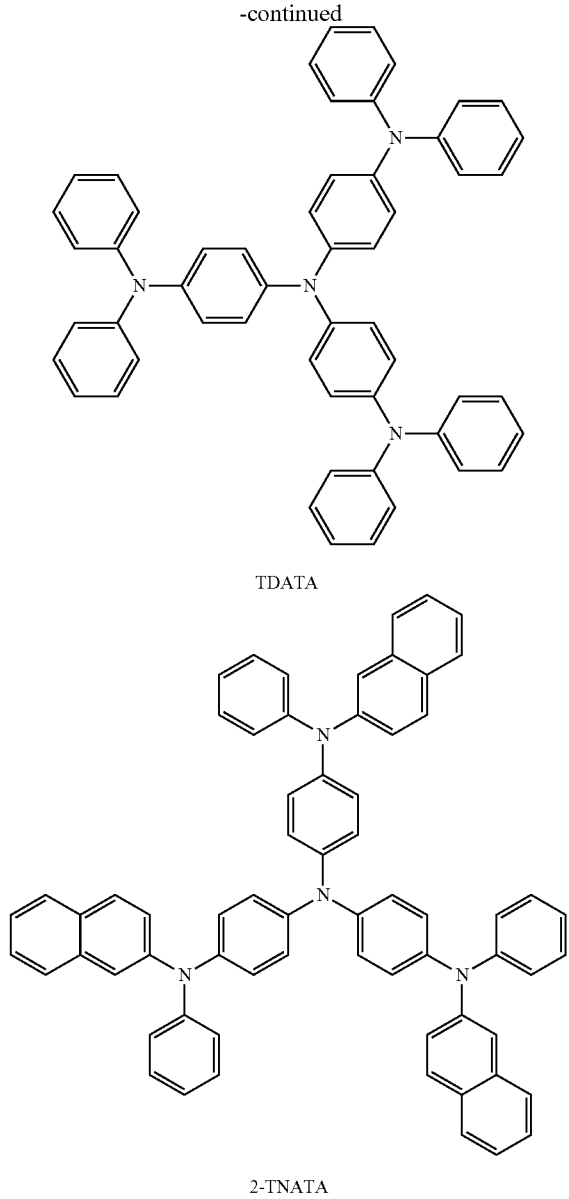

2-TNATA

The thickness of the HIL may be about 100 Å to about 10000 Å. For example, the thickness of the HIL may be about 100 Å to about 1000 Å. If the thickness of the HIL is within this range, good hole injection characteristics may be obtained without increasing the driving voltage of the organic luminescence device.

The hole transport layer (HTL) may be formed on the HIL by various methods, such as vacuum deposition, spin coating, casting, or LB deposition. When the HTL is formed using vacuum deposition or spin coating, the deposition conditions and coating conditions may differ according to the compound selected for preparing the target layer, but may be similar to those described above with reference to the HIL.

The HTL may include the amine compound represented by Formula 1. According to some embodiments of the present invention, when the amine compound of Formula 1 is used to form the EML or the HIL, the HTL may include a known hole transport material. Nonlimiting examples of suitable hole transport materials include carbazole derivatives (such as N-phenylcarbazole or polyvinylcarbazole), amine derivatives having an aromatic condensation ring (such as NPB), and N,N'-bis(3-methylphenyl)-N,N'-diphenyl-[1,1-biphenyl]-4,4'-diamine (TPD). In addition, TCTA may have the ability to block the diffusion of excitons generated in the EML as well as hole transporting capability.

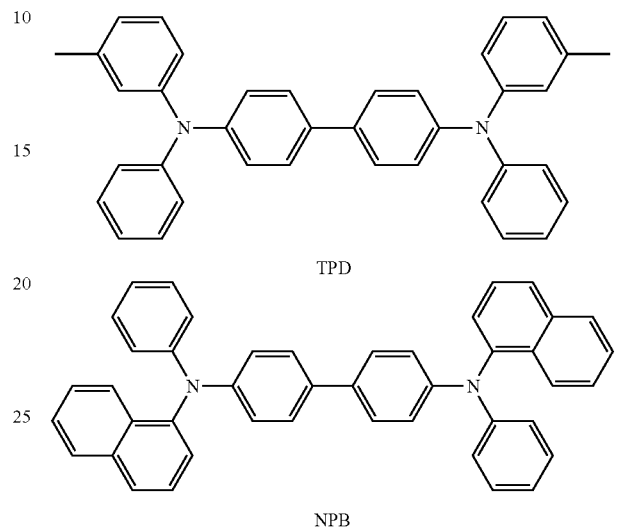

The thickness of the HTL may be about 50 Å to about 1000 Å. For example, the thickness of the HTL may be about 100 Å to about 600 Å. If the thickness of the HTL is within this range, satisfactory hole transporting characteristics may be obtained without increasing the driving voltage of the organic luminescence device.

An electron blocking layer may be formed on the HTL. The electron blocking layer prevents electrons from moving into the HTL, and may include, for example, TATT having the following structure:

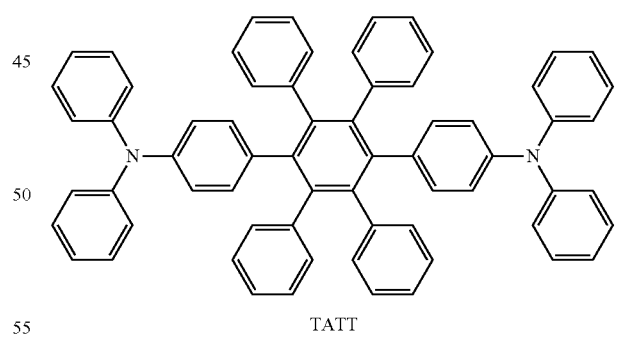

The thickness of the electron blocking layer may be about 50 Å to about 200 Å. If the thickness of the electron blocking layer is within this range, satisfactory electron blocking characteristics may be obtained without substantially increasing the driving voltage of the organic luminescence device.

Then, the EML may be formed on the electron blocking layer. The EML may include the amine compound represented by Formula 1. The EML may be formed by various methods, such as vacuum deposition, spin coating, casting, or LB deposition.

When the EML is formed by vacuum deposition or spin coating, the deposition and coating conditions may differ according to the compound selected for preparing the target layer, but may be similar to those described above with reference to the HIL.

If the amine compound represented by Formula 1 is used to form the HIL or the HTL, the EML may include any suitable luminescent material used in organic luminescence devices.

In some embodiments, the compound represented by Formula 1 or Formula 2 may be used as a host or a dopant. The EML may include the heteroarylamine compound represented by Formula 1 or Formula 2, in addition to various other luminescent materials, for example, known hosts and dopants. The dopant may be a fluorescent dopant or a phosphorescent dopant.

Nonlimiting examples of the host include $Alq_3$, 4,4'-N,N'-dicarbazole-biphenyl (GBP), 9,10-di(naphthalene-2-yl)anthracene (ADN), and distyrylarylene (DSA).

Nonlimiting examples of suitable red dopants include PtOEP, $Ir(piq)_3$, $Btp_2Ir(acac)$, and DCJTB.

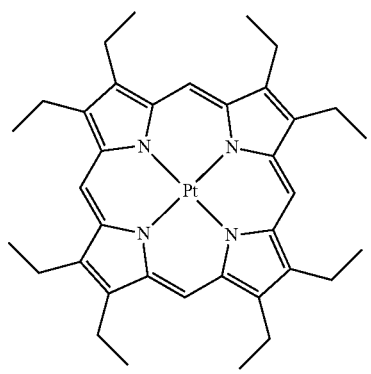

PtOEP

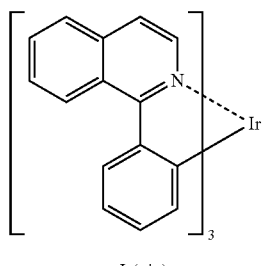

$Ir(piq)_3$

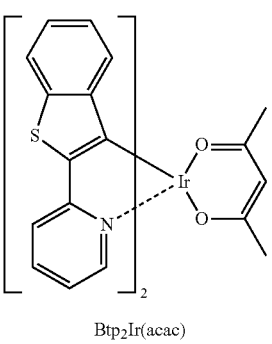

$Btp_2Ir(acac)$

Nonlimiting examples of suitable green dopants include $Ir(ppy)_3$ (where ppy refers to phenylpyridine), $Ir(ppy)_2(acac)$, $Ir(mpyp)_3$, and C545T.

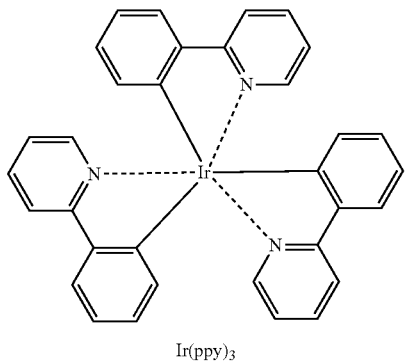

$Ir(ppy)_3$

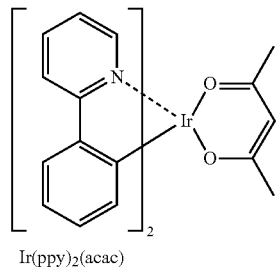

$Ir(ppy)_2(acac)$

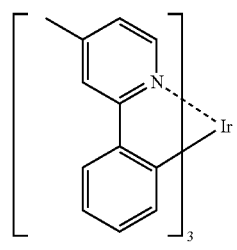

$Ir(mpyp)_3$

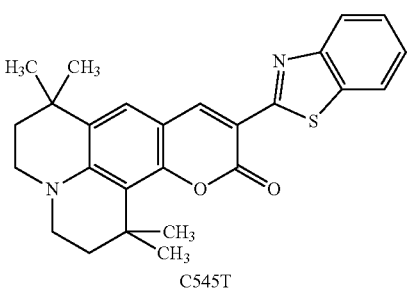

C545T

Nonlimiting examples of suitable blue dopants include $F_2Irpic$, $(F_2ppy)_2Ir(tmd)$, $Ir(dfppz)_3$, ter-fluorene, 4,4'-bis(4-diphenylaminostyryl)biphenyl (DPAVBi), and 2,5,8,11-tetra-t-butyl perylene (TBP).

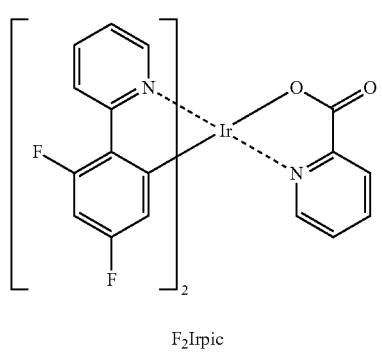
F₂Irpic
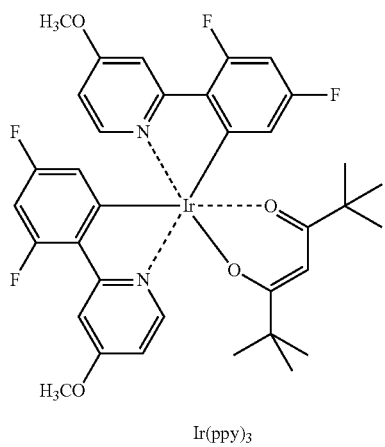
Ir(ppy)₃
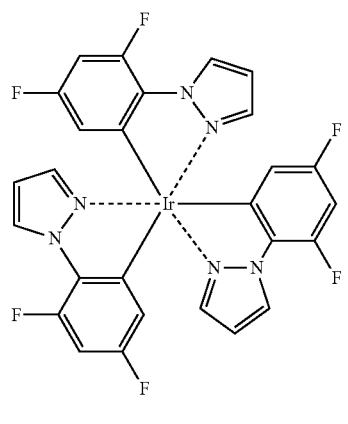
Ir(dfppz)₃
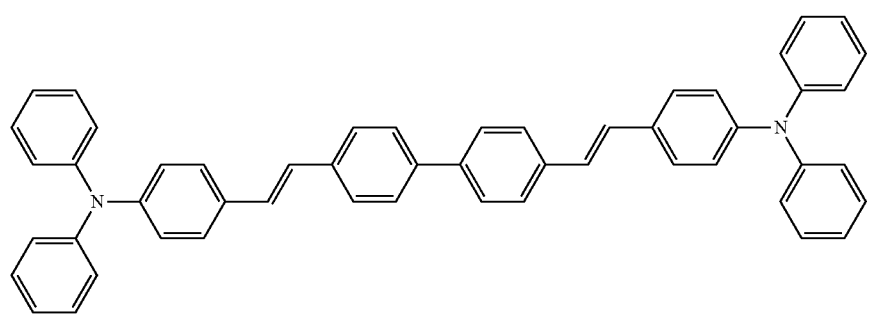
DPAVBi
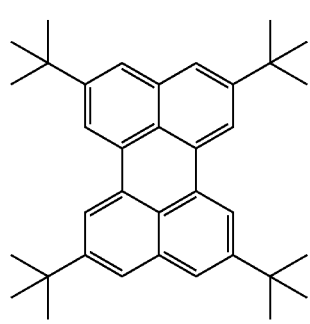
TBP The amount of the dopant may be about 0.1 to about 20 parts by weight based on 100 parts by weight (i.e., the total amount of the host and the dopant) of the EML material. For example, the amount of the dopant may be about 0.5 to about 12 parts by weight based on 100 parts by weight of the EML material. If the amount of the dopant is within this range, concentration quenching may be substantially prevented.

The thickness of the EML may be about 100 Å to 1000 Å. For example, the thickness of the EML may be about 200 Å to about 600 Å. If the thickness of the EML is within this range, good luminescence characteristics may be obtained without substantially increasing the driving voltage of the organic luminescence device.

If the EML includes a phosphorescent dopant, a hole blocking layer (HBL) for preventing diffusion of triplet excitons or holes into the ETL may be formed on the EML (not shown in FIG. 1). The HBL material is not particularly limited, and may be any suitable HBL material. Nonlimiting examples of suitable HBL materials include oxadiazole derivatives, triazole derivatives, phenanthroline derivatives, bis(2-methyl-8-quinolato)-(p-phenylphenolato)-aluminum (Balq), bathocuproine(BCP), and tris(N-arylbenzimidazole) (TPBI).

The thickness of the HBL may be about 50 Å to about 1000 Å. For example, the thickness of the HBL may be about 100 Å to about 300 Å. If the thickness of the HBL is less than about 50 Å, the hole blocking characteristics of the HBL may be degraded. On the other hand, if the thickness of the HBL is greater than about 1000 Å, the driving voltage of the organic luminescence device may be increased.

Then, the ETL may be formed on the HBL by various known methods, such as vacuum deposition, spin coating, casting, or LB deposition. When the ETL is formed by vacuum deposition or spin coating, the deposition and coating conditions may differ according to the compound selected for preparing the target layer, but may be similar to those described above with reference to the HIL. The ETL material is not particularly limited, and may be any suitable material, nonlimiting examples of which include quinoline derivatives, such as tris(8-quinolinolate)aluminum ($Alq_3$), TAZ, or Balq

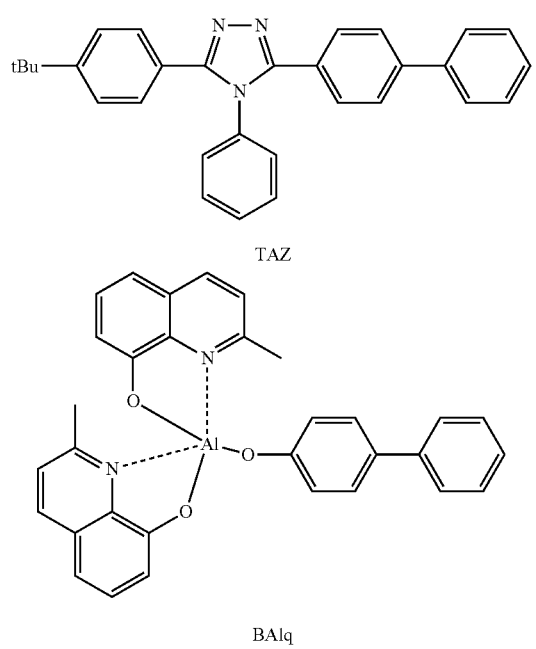

TAZ

BAlq

The thickness of the ETL may be about 100 Å to about 1000 Å. For example, the thickness of the ETL may be about 100 Å to about 500 Å. If the thickness of the ETL is within this range, good electron transporting characteristics may be obtained without substantially increasing the driving voltage of the organic luminescence device.

In addition, an EIL material that allows electrons to be easily injected from the cathode may be deposited on the ETL. Nonlimiting examples of the EIL material include $BaF_2$, LiF, NaCl, CsF, $Li_2O$, BaO, and Liq.

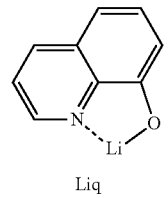

Liq

Deposition conditions for forming the EIL may differ according to the compound selected for preparing the target layer, and may be similar to those described above with reference to the HIL.

The thickness of the EIL may be about 1 Å to about 100 Å. For example, the thickness of the EIL may be about 5 Å to about 90 Å. If the thickness of the EIL is within this range, good electron injection characteristics may be obtained without substantially increasing the driving voltage of the organic luminescence device.

Finally, a second electrode may be formed on the EIL by vacuum deposition or sputtering. The second electrode may be used as a cathode or an anode. The second electrode material may be material having a low work function, such as a metal, an alloy, an electrically conducting compound, or a mixture thereof. Nonlimiting examples of the second electrode material include lithium (Li), magnesium (Mg), aluminum (Al), aluminum-lithium (Al—Li), potassium (Ca), magnesium-indium (Mg—In), and magnesium-silver(Mg—Ag). If the organic luminescence device is a top luminescence device, the organic luminescence device may include a transparent cathode including ITO or IZO.

The organic luminescence device according to embodiments of the present invention may be used in various types of flat panel display devices, for example, passive matrix organic luminescence display devices or active matrix organic luminescence display devices. When the organic luminescence devices according to embodiments of the present invention are used in active matrix organic luminescence display devices, a first electrode disposed on a substrate may be electrically connected to a source electrode or a drain electrode of a thin film transistor as a pixel electrode. In addition, the organic luminescence devices according to embodiments of the present invention may also be used in flat panel display devices that display images in two directions.

According to embodiments of the present invention, at least one layer of the organic luminescence device may be formed by depositing the compound of Formula 1 or Formula 2, or by coating a solution prepared using the compound of Formula 1 or Formula 2.

The organic luminescence devices described above may also be used in various types of flat panel display devices, for example, in passive matrix organic luminescence display devices or active matrix organic luminescence display devices. When the organic luminescence devices according to the embodiments of the present invention are used in active matrix organic luminescence display devices, a first electrode disposed on a substrate may be electrically connected to a source electrode or a drain electrode of a thin film transistor as a pixel electrode.

In addition, the organic luminescence devices according to embodiments of the present invention may also be used in flat panel display devices that display images in two directions.

Figure 2:
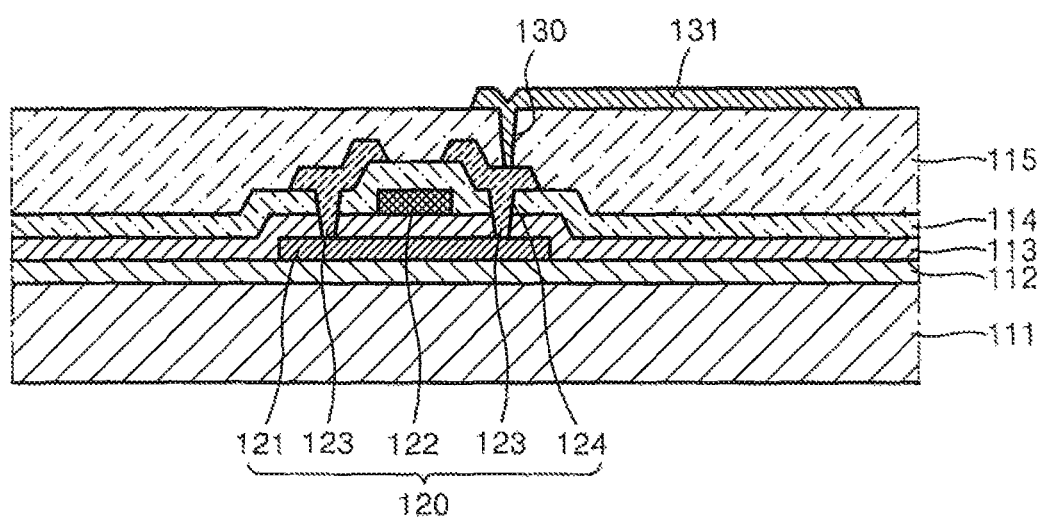
FIG. 2 is a cross-sectional view of a flat panel display according to an embodiment of the present invention.

According to embodiments of the present invention, as shown in FIG. 2, a flat panel display includes a driving circuit 120 electrically connected to a pixel unit on a substrate 111. An insulating layer 112 such as a barrier layer and/or a buffer layer may be formed on the substrate 111 to planarize the surface of the substrate and to substantially prevent the diffusion of impurities and the penetration of external moisture and air.

A thin film transistor (TFT) as the driving circuit 120 is formed on the insulating layer 112. According to some embodiments, a top gate TFT may be used. However, it is understood that various other types of TFTs may also be used. An activation layer 121 of the TFT includes a semiconductor material and is disposed on the insulating layer 112. A gate insulating layer 113 covers the activation layer 121. The activation layer 121 may include inorganic semiconductor materials (such as amorphous silicon or polysilicon), or organic semiconductor materials, and may have a source region, a drain region, and a channel region between the source region and the drain region.

A gate electrode 122 is disposed on the gate insulating layer 113, and an interlayer insulating layer 114 covers the gate electrode 122. Source and drain electrodes 123 are disposed on the interlayer insulating layer 114 and contact the activation layer through contact holes 124. A planarization layer 115 covers the source and drain electrodes 123. It is understood that the stack structure of the TFT is not limited to this constructions, but rather the TFT may have any suitable structure.

The first electrode 131 of the organic light emitting device is formed on the planarization layer 115, and is electrically connected to the source and drain electrodes 123 via a through hole 130. A pixel definition layer (not shown) is a thin inorganic layer formed on the first electrode 131. An opening is formed in the pixel definition layer to expose the first electrode 131 through the opening.

The following Examples are presented for illustrative purposes only and do not limit the scope of the present invention.

SYNTHESIS EXAMPLE 1

Synthesis of Intermediate 1

7 g (30 mmol) of 2-bromobiphenyl, 7.62 g (45 mmol) of 4-aminobiphenyl, 4.3 g (45 mmol) of t-BuONa, 0.55 g (0.6 mmol) of $Pd_2(dba)_3$, and 0.12 g (0.6 mmol) of $P(t-Bu)_3$ were dissolved with 100 mL of toluene and the mixture was stirred for 3 hours at a temperature of 90° C. When the reaction was completed, the reaction solution was cooled to room temperature and then subjected to extraction three times with distilled water and 100 mL of diethylether, thereby obtaining an organic layer. The organic layer was then dried over magnesium sulfate and the residue obtained by evaporating the solvent was isolated and purified by silica gel column chromatography to obtain 8.77 g (yield: 91%) of Intermediate 1. The obtained compound was identified by high resolution mass spectrometry (HR-MS). $C_{24}H_{19}N$ calc.: 321.1517; found 321.1519

SYNTHESIS EXAMPLE 2

Synthesis of Intermediate 2

Intermediate 2 (yield: 87%) was synthesized in the same manner as Intermediate 1, except that 2-bromo-9,9'-dimethylfluorene was reacted instead of 2-bromobiphenyl. The obtained compound was identified by HR-MS. $C_{27}H_{23}N$ calc.: 361.1830; found 361.1835

SYNTHESIS EXAMPLE 3

Synthesis of Intermediate 3

Intermediate 3 (yield: 85%) was synthesized in the same manner as Intermediate 2, except that 2-amino-9,9'-dimethylfluorene was reacted instead of 4-aminobiphenyl. The obtained compound was identified by HR-MS. $C_{30}H_{27}N$ calc.: 401.2143; found 401.2148

SYNTHESIS EXAMPLE 4

Synthesis of Intermediate 4

Intermediate 4 (yield: 81%) was synthesized in the same manner as Intermediate 1, except that 3-iodo-9-phenyl-9H-carbazole was reacted instead of 2-bromobiphenyl. The obtained compound was identified by HR-MS. $C_{30}H_{22}N_2$ calc.: 410.1783; found 410.1787

SYNTHESIS EXAMPLE 5

Synthesis of Intermediate 5

Intermediate 3 (yield: 80%) was synthesized in the same manner as Intermediate 2, except that 3-iodo-9-phenyl-9H-carbazole was reacted instead of 4-aminobiphenyl. The obtained compound was identified by HR-MS. $C_{33}H_{26}N_2$ calc.: 450.2096; found 450.2100

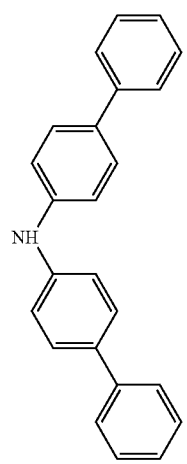

Intermediate 1

Intermediate 2

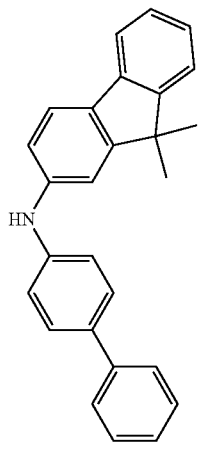

Intermediate 3

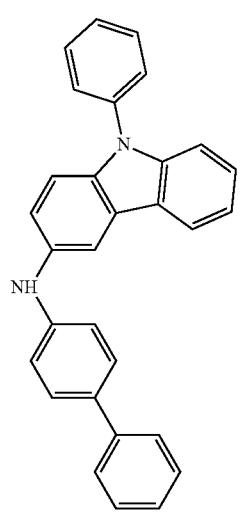

Intermediate 5

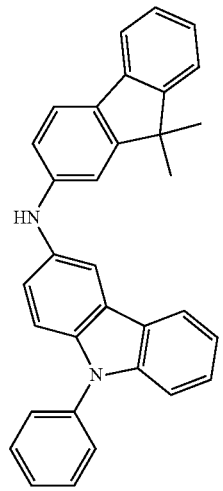

SYNTHESIS EXAMPLE 6

Synthesis of Intermediate 6

5 g (20 mmol) of 1-bromo-4-naphthalene boronic acid, 6.6 g (20 mmol) of 1,4-diiodo benzene, 1.04 g (0.9 mmol) of Pd(PPh$_3$)$_4$, and 5.5 g (40 mmol) of K$_2$CO$_3$ were dissolved in 100 mL of a THF/H$_2$O (2:1) mixed solution, and then the mixture was stirred for 5 hours at a temperature of 80° C. The reaction solution was extracted three times with 600 ml of diethylether. The collected organic layer was dried over magnesium sulfate and the residue obtained by evaporating the solvent was recrystallized with dichloromethane and normal hexane (n-hexane), thereby obtaining 6.5 g (yield 79%) of Intermediate 6. The obtained compound was identified by HR-MS. C$_{16}$H$_{10}$BrI calc.: 407.9011; found 407.9015

SYNTHESIS EXAMPLE 7

Synthesis of Intermediate 7

5 g (20 mmol) of 1-bromo-4-naphthalene boronic acid, 8.92 g (20 mmol) of 2,7-diiodo-9,9'-dimethylfluorene, 1.04 g (0.9 mmol) of Pd(PPh$_3$)$_4$, and 5.5 g (40 mmol) of K$_2$CO$_3$ were dissolved in 100 mL of a THF/H$_2$O(2:1) mixed solution, and then the mixture was stirred for 5 hours at a temperature of 80° C. The reaction solution was extracted three times with 600 ml of diethylether. The collected organic layer was dried over magnesium sulfate and the residue obtained by evaporating the solvent was recrystallized with dichloromethane and normal hexane (n-hexane), thereby obtaining 7.9 g (yield 75%) of Intermediate 7. The obtained compound was identified by HR-MS. C$_{25}$H$_{18}$BrI calc.: 523.9637; found 523.9642

Intermediate 6

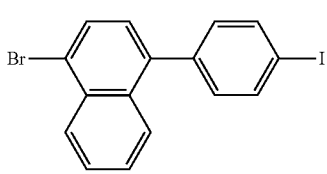

-continued

Intermediate 7

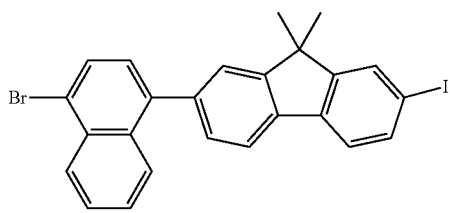

SYNTHESIS EXAMPLE 8

Synthesis of Intermediate 8

4.38 g (20 mmol) of naphthalene-2-phenylamine, 12.3 g (30 mmol) of Intermediate 6, 2.88 g (30 mmol) of t-BuONa, 0.36 g (0.4 mmol) of $Pd_2(dba)_3$, and 0.08 g (0.4 mmol) of $P(t-Bu)_3$ were dissolved in 100 mL of toluene and then the mixture was stirred for 3 hours at a temperature of 90° C. When the reaction was completed, the reaction solution was cooled to room temperature and then extracted three times with distilled water and 100 mL of diethylether, thereby obtaining an organic layer. The organic layer was dried over magnesium sulfate and the residue obtained by evaporating the solvent was isolated and purified by silica gel column chromatography to obtain 8.8 g (yield 88%) of Intermediate 8. The obtained compound was identified by HR-MS. $C_{32}H_{22}BrN$ calc.: 499.0936; found 499.0940

SYNTHESIS EXAMPLE 9

Synthesis of Intermediate 9

6.43 g (20 mmol) of Intermediate 1, 12.3 g (30 mmol) of Intermediate 6, 2.88 g (30 mmol) of t-BuONa, 0.36 g (0.4 mmol) of $Pd_2(dba)_3$, and 0.08 g (0.4 mmol) of $P(t-Bu)_3$ were dissolved in 100 mL of toluene and then the mixture was stirred for 3 hours at a temperature of 90° C. When the reaction was completed, the reaction solution was cooled to room temperature and then extracted three times with distilled water and 100 mL of diethylether, thereby obtaining an organic layer. The organic layer was dried over magnesium sulfate and the residue obtained by evaporating the solvent was isolated and purified by silica gel column chromatography to obtain 7.7 g (yield 64%) of Intermediate 9. The obtained compound was identified by HR-MS. $C_{40}H_{28}BrN$ calc.: 601.1405; found 601.1409

SYNTHESIS EXAMPLE 10

Synthesis of Intermediate 10

Intermediate 10 (yield: 61%) was synthesized in the same manner as Intermediate 9, except that Intermediate 2 was reacted instead of Intermediate 1. The obtained compound was identified by HR-MS. $C_{43}H_{32}BrN$ calc.: 641.1718; found 641.1722

SYNTHESIS EXAMPLE 11

Synthesis of Intermediate 11

Intermediate 11 (yield: 58%) was synthesized in the same manner as Intermediate 9, except that Intermediate 3 was reacted instead of Intermediate 1. The obtained compound was identified by HR-MS. $C_{46}H_{36}BrN$ calc.: 6812031; found 6812035

SYNTHESIS EXAMPLE 12

Synthesis of Intermediate 12

Intermediate 12 (yield: 63%) was synthesized in the same manner as Intermediate 9, except that Intermediate 4 was reacted instead of Intermediate 1. The obtained compound was identified by HR-MS. $C_{46}H_{31}BrN_2$ calc.: 690.1671; found 690.1675

SYNTHESIS EXAMPLE 13

Synthesis of Intermediate 13

Intermediate 13 (yield: 60%) was synthesized in the same manner as Intermediate 9, except that Intermediate 5 was reacted instead of Intermediate 1. The obtained compound was identified by HR-MS. $C_{49}H_{35}BrN_2$ calc.: 730.1984; found 730.1988

Intermediate 8

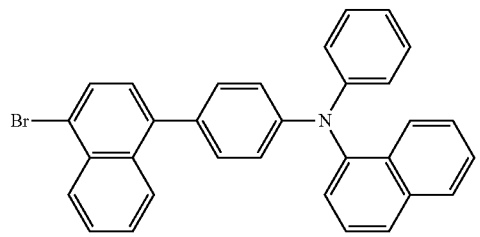

Intermediate 9

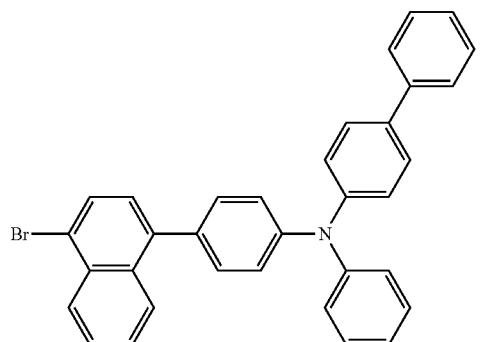

Intermediate 10

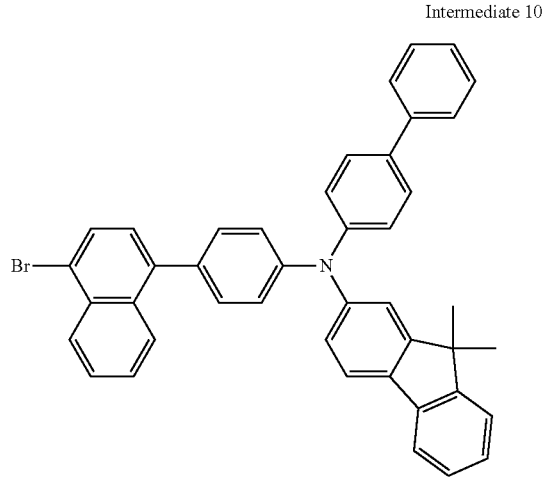

Intermediate 11

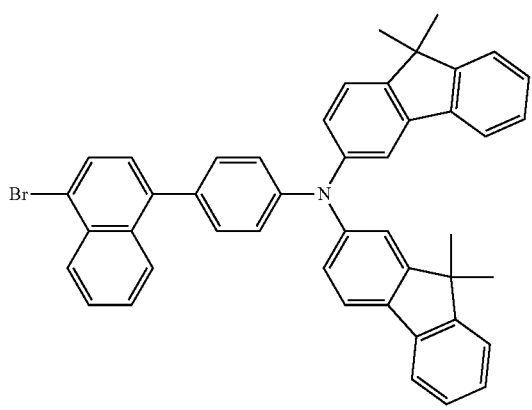

Intermediate 12

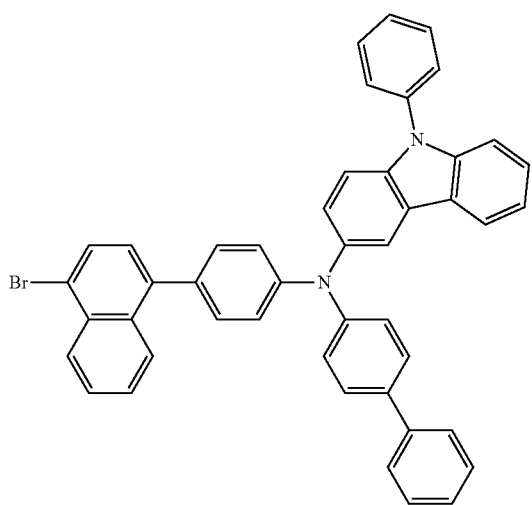

Intermediate 13

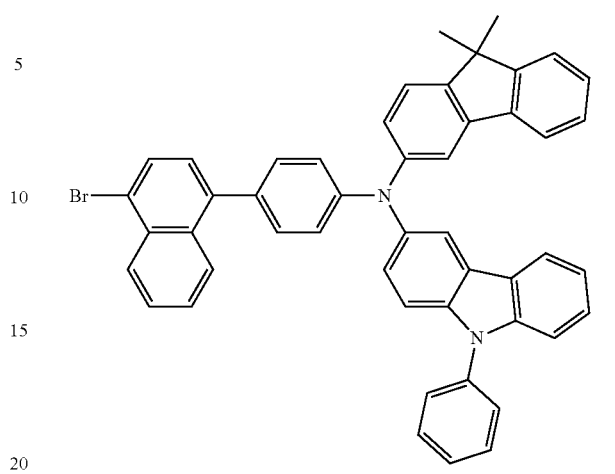

SYNTHESIS EXAMPLE 14

Synthesis of Intermediate 14

6.43 g (20 mmol) of Intermediate 1, 15.7 g (30 mmol) of Intermediate 7, 2.88 g (30 mmol) of t-BuONa, 0.36 g (0.4 mmol) of $Pd_2(dba)_3$, and 0.08 g (0.4 mmol) of $P(t-Bu)_3$ were dissolved in 100 mL of toluene and then the mixture was stirred for 3 hours at a temperature of 90° C. When the reaction was completed, the reaction solution was cooled to room temperature and then extracted three times with distilled water and 100 mL of diethylether, thereby obtaining an organic layer. The organic layer was dried over magnesium sulfate and the residue obtained by evaporating a solvent was isolated and purified by silica gel column chromatography to obtain 8.91 g (yield 62%) of Intermediate 14. The obtained compound was identified by HR-MS. $C_{49}H_{36}BrN$ calc.: 717.2031; found 717.2035

SYNTHESIS EXAMPLE 15

Synthesis of Intermediate 15

15.05 g (60 mmol) of 1-bromo-4-naphthalene boronic acid, 12.5 g (10 mmol) of tris-4-bromophenylamine, 1.73 g (1.5 mmol) of $Pd(PPh_3)_4$, and 6.22 g (45 mmol) of $K_2CO_3$ were dissolved in 100 mL of a $THF/H_2O(2:1)$ mixed solution and then the mixture was stirred for 5 hours at a temperature of 80° C. The reaction solution was extracted three times with 600 ml of diethylether, thereby obtaining an organic layer. The organic layer was dried over magnesium sulfate and the residue obtained by evaporating the solvent was recrystallized with dichloromethane and normal hexane (n-hexane), thereby obtaining 4.47 g (yield 52%) of Intermediate 15. The obtained compound was identified by HRMS. $C_{48}H_{30}Br_3N$ calc.: 856.9928; found 856.9932

Intermediate 14

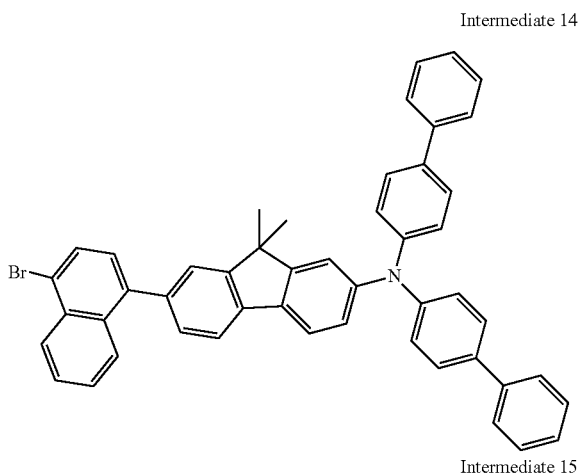

Intermediate 15

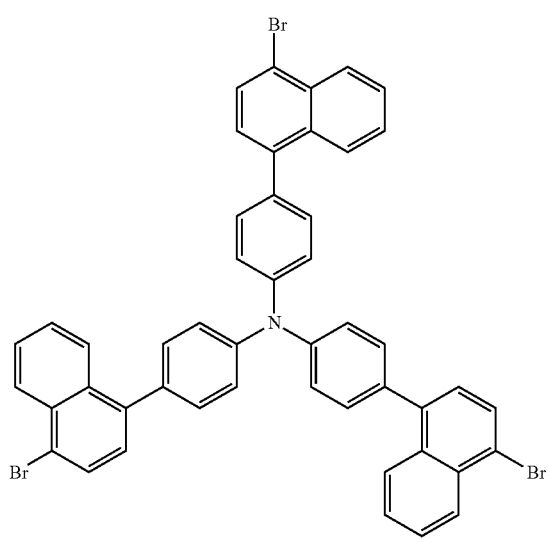

SYNTHESIS EXAMPLE 16

Synthesis of Intermediate 16

10 g (20 mmol) of Intermediate 8, 5.1 g (26 mmol) of benzophenone hydrazone, 2.88 g (30 mmol) of t-BuONa, 0.09 g (0.4 mmol) of $Pd(OAc)_2$, and 0.19 g (0.4 mmol) of 2-dicyclohexylphosphino-2',4',6'-triisopropylbiphenyl were dissolved in 60 mL of toluene and the mixture was stirred for 3 hours at a temperature of 90° C. The reaction solution was cooled to room temperature and then distilled water was added thereto, and the resultant solution was extracted twice with 100 mL of diethylether and once with 100 mL of dichloromethane, thereby obtaining an organic layer. The organic layer was dried over magnesium sulfate and the residue obtained by evaporating the solvent was isolated and purified by silica gel column chromatography to obtain 11.2 g (yield 91%) of Intermediate 16. The obtained compound was identified by HR-MS. $C_{45}H_{33}N_3$ calc.: 615.2674; found 615.2678

SYNTHESIS EXAMPLE 17

Synthesis of Intermediate 17

6.15 g (10 mmol) of Intermediate 16, 3.8 g (20 mmol) of p-toluenesulfonic acid monohydrate, and 2.94 g (15 mmol) of benzylphenylketone were mixed with 40 mL of ethanol and 60 mL of toluene and the mixture was stirred at a temperature of 110° C. for 24 hours. The reaction product was cooled to room temperature, distilled water was added thereto and the product was washed twice with 100 mL of diethylether and twice with 100 mL of dichloromethane, thereby obtaining an organic layer. The organic layer was dried over magnesium sulfate and the residue obtained by evaporating the solvent was isolated and purified by silica gel column chromatography to obtain 4.41 g (yield 72%) of Intermediate 17. The obtained compound was identified by HR-MS. $C_{46}H_{32}N_2$ calc.: 612.2565; found 612.2569

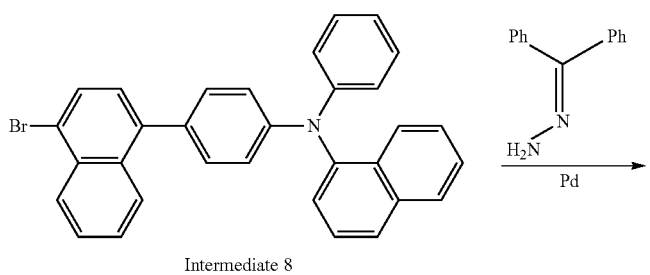

Intermediate 8

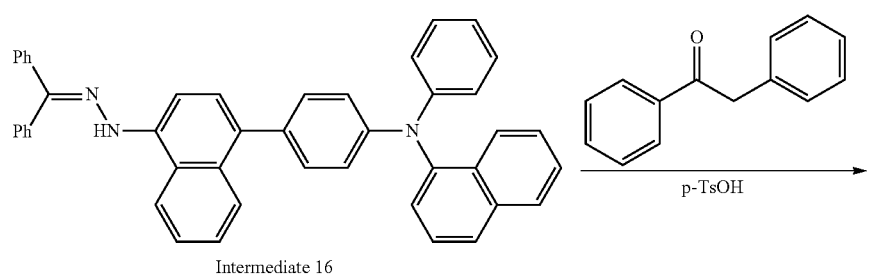

Intermediate 16

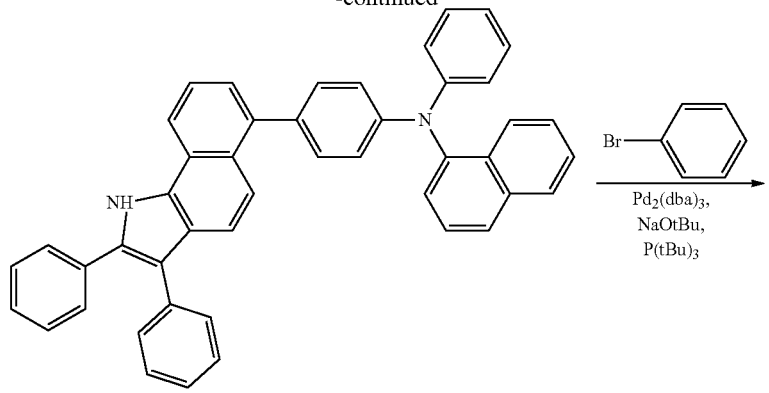

Intermediate 17

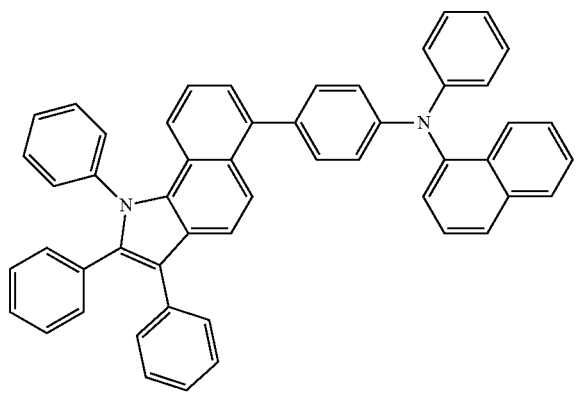

1

SYNTHESIS EXAMPLE 18

Synthesis of Compound 1

3.06 g (5 mmol) of Intermediate 17, 0.94 g (6 mmol) of bromobenzene, 1.44 g (15 mmol) of t-BuONa, 183 mg (0.2 mmol) of $Pd_2(dba)_3$, and 40 mg (0.2 mmol) of $P(t-Bu)_3$ were dissolved in 30 mL of toluene and then the mixture was stirred for 3 hours at a temperature of 90° C. When the reaction was completed, the reaction solution was cooled to room temperature and then extracted three times with distilled water and 40 mL of diethylether, thereby obtaining an organic layer. The organic layer was dried over magnesium sulfate and the residue obtained by evaporating the solvent was isolated and purified by silica gel column chromatography to obtain 2.65 g (yield 77%) of Compound 1. The obtained compound was identified by HR-MS and NMR. $C_{52}H_{36}N_2$ calc.: 6882878; found 688.2882; $^1$H NMR (CDCl$_3$, 400 MHz) δ (ppm) 8.49 (d, 1H), 8.23-8.21 (m, 2H), 7.85 (d, 1H), 7.71-7.25 (m, 24H), 7.15 (dd, 2H), 6.82 (dt, 1H), 6.56 (dd, 2H), 6.33 (d, 1H), 6.17 (d, 2H).

SYNTHESIS EXAMPLE 19

Synthesis of Compound 2

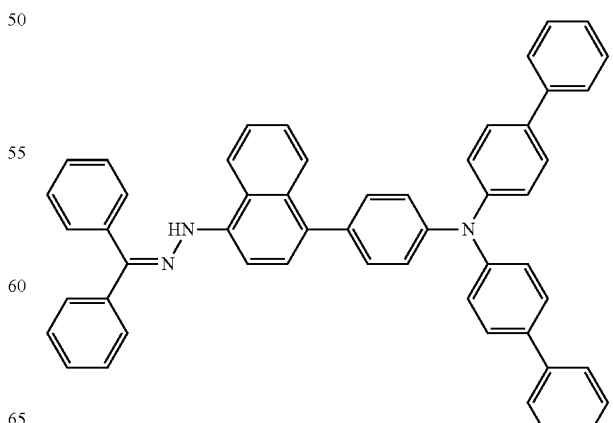

Intermediate 18

-continued

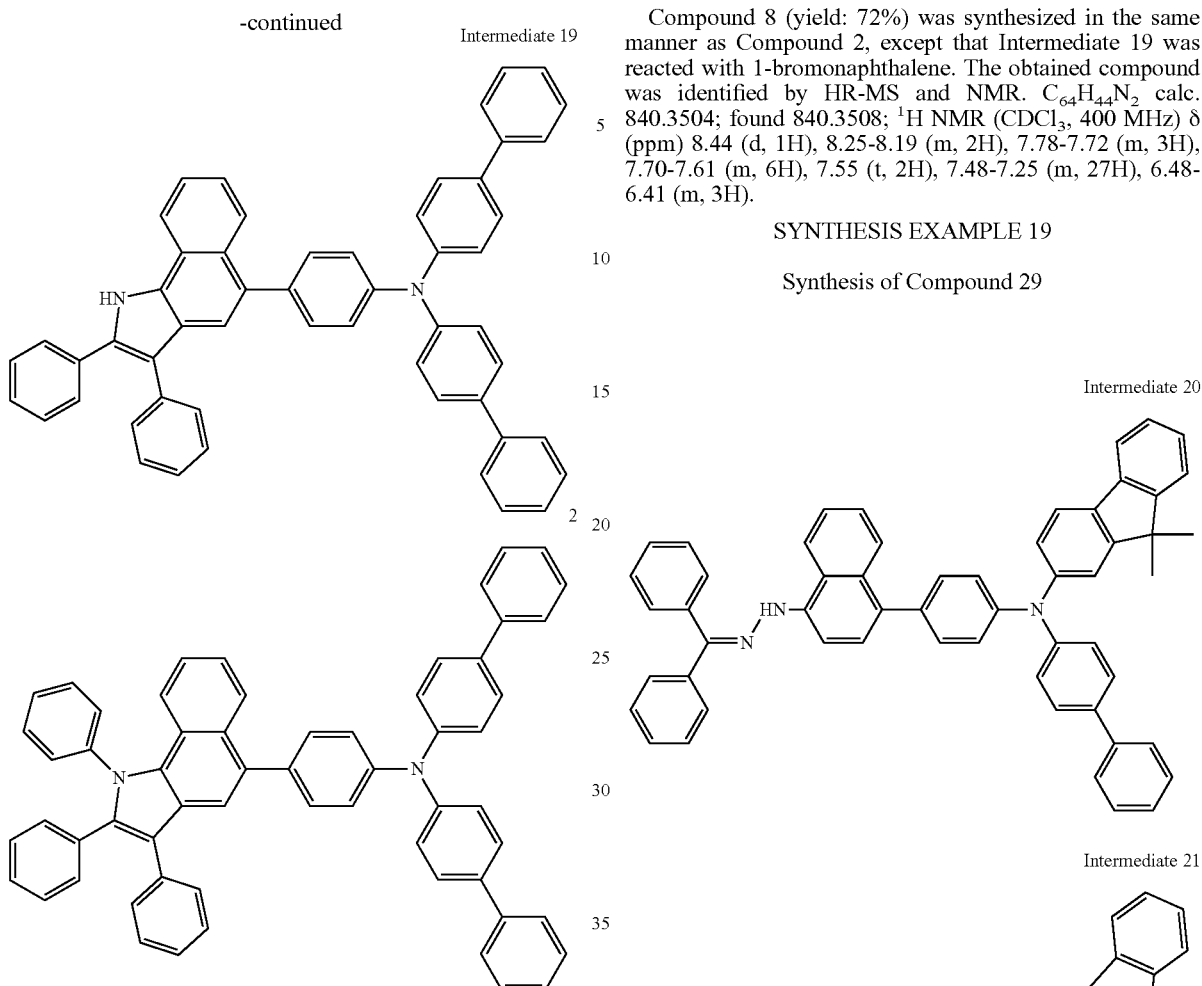

Compound 2 (yield: 70%) was synthesized in the same manner as Compound 1, except that Intermediate 18 and Intermediate 19 were sequentially synthesized using Intermediate 9 instead of Intermediate 8, and Intermediate 19 was reacted with bromobenzene. The obtained compound was identified by HR-MS and NMR. $C_{60}H_{42}N_2$ calc.: 790.3348; found 790.3352; $^1$H NMR (CDCl$_3$, 400 MHz) δ (ppm) 8.25-8.19 (m, 2H), 7.78-7.72 (m, 3H), 7.70-7.63 (m, 6H), 7.58-7.24 (m, 25H), 7.16-7.11 (dd, 2H), 6.87-6.81 (m, 4H).

SYNTHESIS EXAMPLE 20

Synthesis of Compound 8

Compound 8 (yield: 72%) was synthesized in the same manner as Compound 2, except that Intermediate 19 was reacted with 1-bromonaphthalene. The obtained compound was identified by HR-MS and NMR. $C_{64}H_{44}N_2$ calc. 840.3504; found 840.3508; $^1$H NMR (CDCl$_3$, 400 MHz) δ (ppm) 8.44 (d, 1H), 8.25-8.19 (m, 2H), 7.78-7.72 (m, 3H), 7.70-7.61 (m, 6H), 7.55 (t, 2H), 7.48-7.25 (m, 27H), 6.48-6.41 (m, 3H).

SYNTHESIS EXAMPLE 19

Synthesis of Compound 29

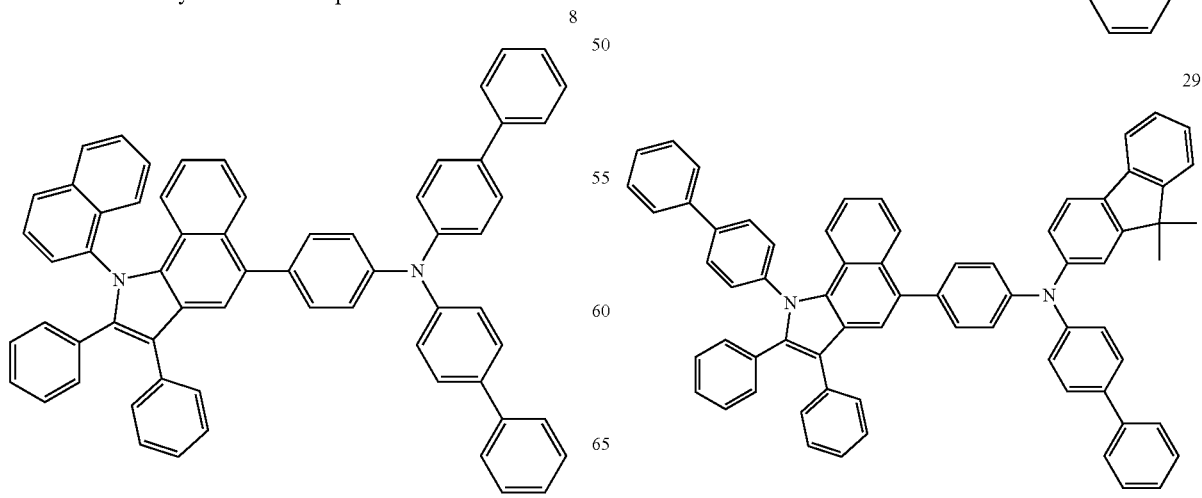

Compound 29 (yield: 70%) was synthesized in the same manner as Compound 1, except that Intermediate 20 and Intermediate 21 were synthesized using Intermediate 10 instead of Intermediate 8, and Intermediate 21 was reacted with 4-bromobiphenyl. The obtained compound was identified by HR-MS and NMR. $C_{69}H_{50}N_2$ calc. 906.3974; found 906.3978; $^1$H NMR (CDCl$_3$, 400 MHz) δ (ppm) 8.25-8.21 (m, 2H), 7.98 (d, 1H), 7.76 (d, 2H), 7.70-7.62 (m, 4H), 7.60-7.53 (m, 5H), 7.47-7.20 (m, 21H), 7.05 (d, 1H), 6.95 (t, 1H), 6.79 (d, 2H), 6.64-6.59 (m, 4H), 6.53 (d, 1H), 1.96 (s, 6H).

SYNTHESIS EXAMPLE 20

Synthesis of Compound 32

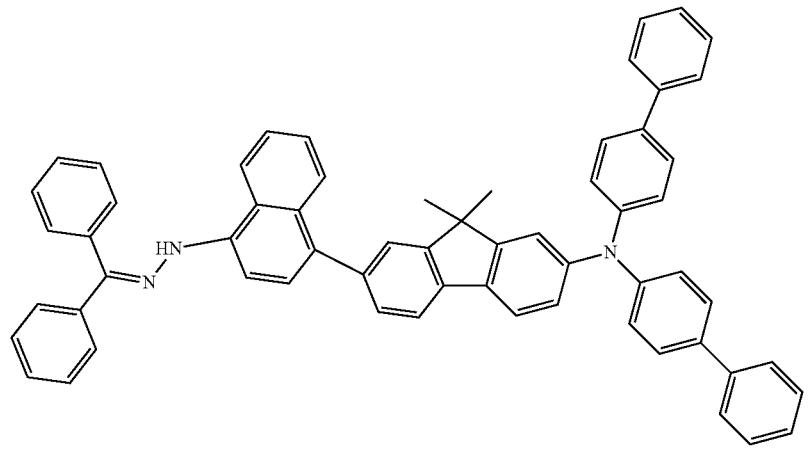

Intermediate 22

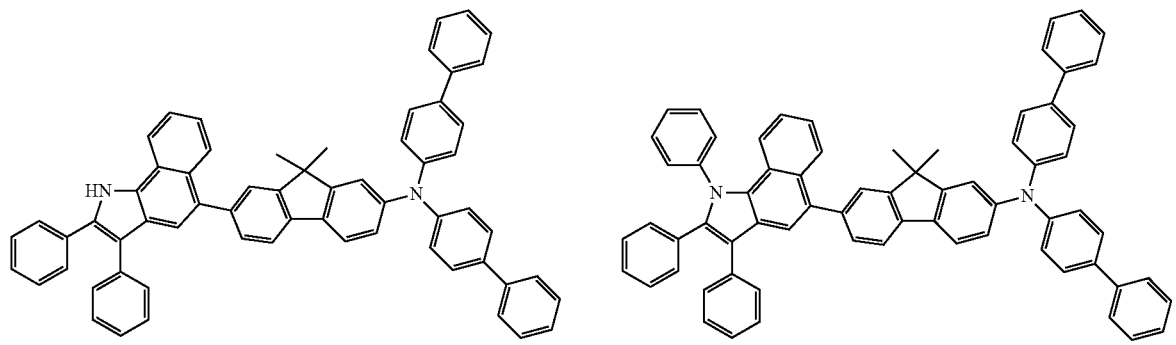

Intermediate 23

Compound 32 (yield: 65%) was synthesized in the same manner as Compound 1, except that Intermediate 22 and Intermediate 23 were synthesized using Intermediate 14 instead of Intermediate 8, and Intermediate 23 was reacted with bromobenzene. The obtained compound was identified by HR-MS and NMR. $C_{63}H_{50}N_2$ calc. 906.3974; found 906.3978; $^1$H NMR (CDCl$_3$, 400 MHz) δ (ppm) 8.25-8.18 (m, 2H), 7.76-7.72 (m, 3H), 7.69-7.62 (m, 4H), 7.60-7.25 (m, 22H), 7.22 (s, 1H), 7.13-7.03 (m, 6H), 6.96 (d, 1H), 6.83 (d, 4H), 6.73 (d, 1H), 1.98 (s, 6H).

SYNTHESIS EXAMPLE 21

Synthesis of Compound 58

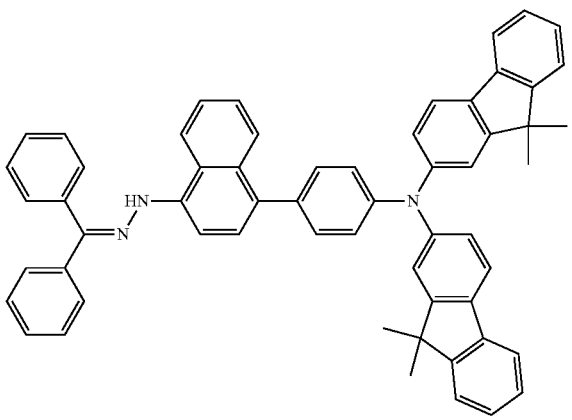

Intermediate 24

Intermediate 25

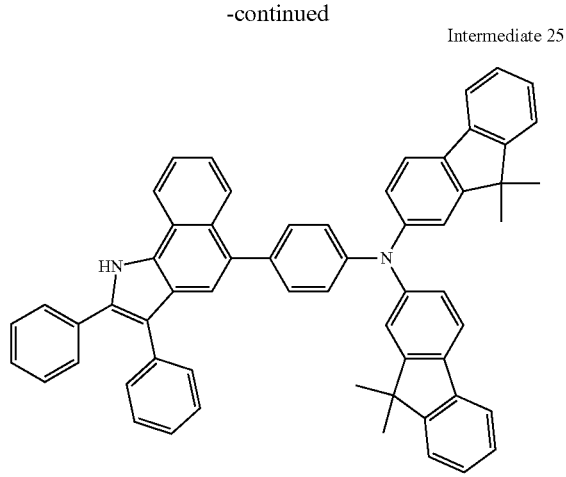

58

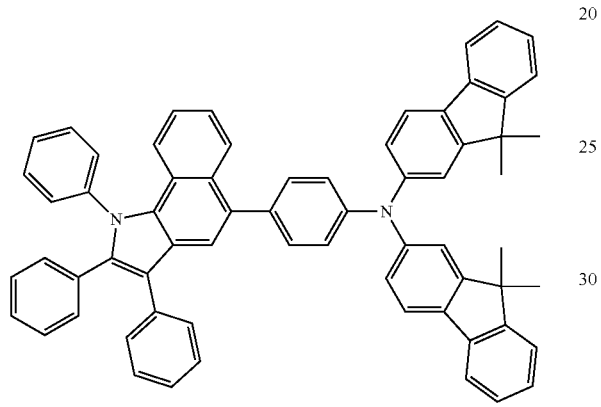

Compound 58 (yield: 69%) was synthesized in the same manner as Compound 1, except that Intermediate 24 and Intermediate 25 were synthesized using Intermediate 11 instead of Intermediate 8, and Intermediate 25 was reacted with bromobenzene. The obtained compound was identified by HR-MS and NMR. $C_{66}H_{50}N_2$ calc. 870.3974; found 870.3978; $^1$H NMR (CDCl$_3$, 400 MHz) δ (ppm) 8.24-8.21 (m, 2H), 7.98 (d, 2H), 7.72-7.65 (m, 4H), 7.60-7.20 (m, 20H), 7.13 (d, 2H), 7.06 (d, 2H), 6.95 (t, 2H), 6.78 (d, 2H), 6.72 (d, 2H), 1.97 (s, 12H).

SYNTHESIS EXAMPLE 22

Synthesis of Compound 81

Intermediate 26

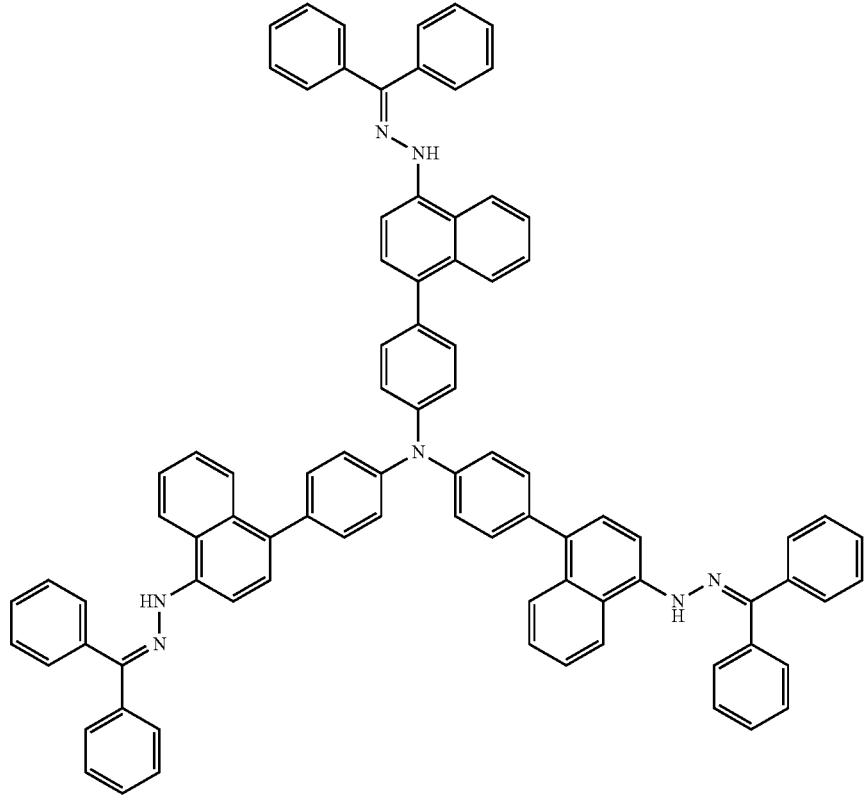

Intermediate 27
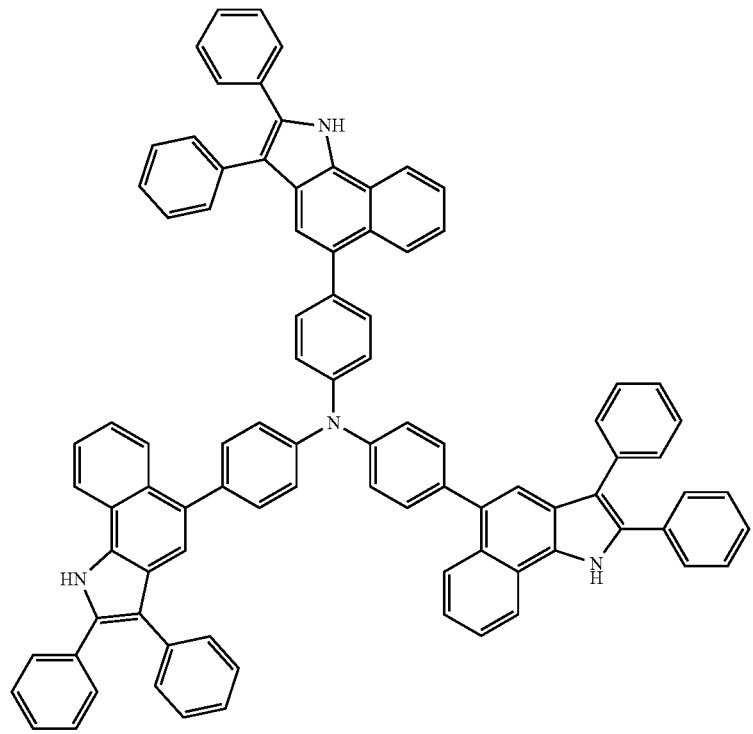
81
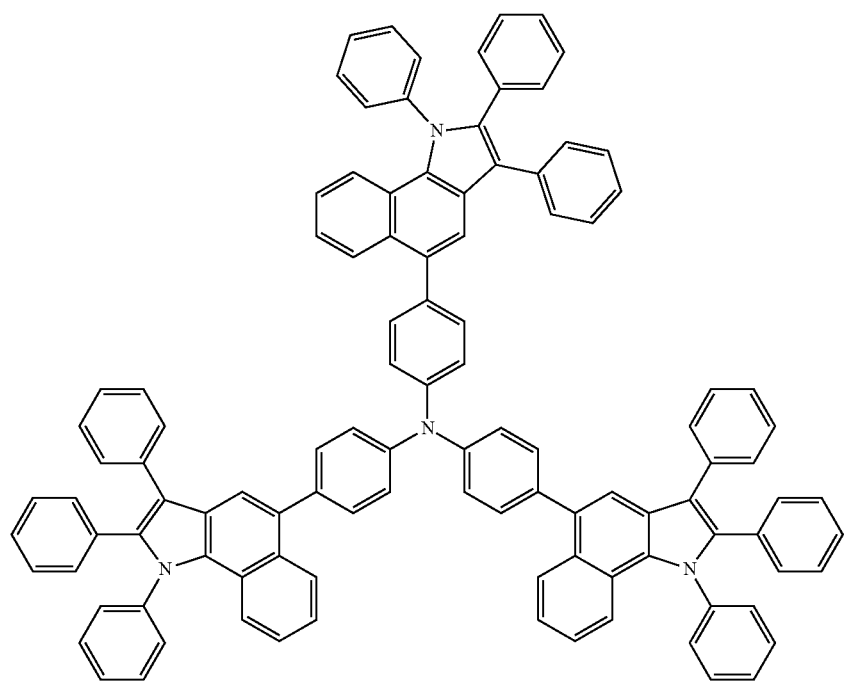
Compound 81 (yield: 73%) was synthesized in the same manner as Compound 1, except that Intermediate 26 and Intermediate 27 were synthesized using Intermediate 15 instead of Intermediate 8, and Intermediate 27 was reacted with bromobenzene. The obtained compound was identified by HR-MS and NMR. $C_{104}H_{72}N_4$ calc. 1424.5757; found 1424.5761; $^1$H NMR (CDCl$_3$, 400 MHz) δ (ppm) 8.25-8.20 (m, 3H), 7.72-7.65 (m, 3H), 7.55 (t, 3H), 7.52-7.25 (m, 57H), 7.11-7.05 (m, 3H), 6.93 (d, 3H).

SYNTHESIS EXAMPLE 23

Synthesis of Compound 84

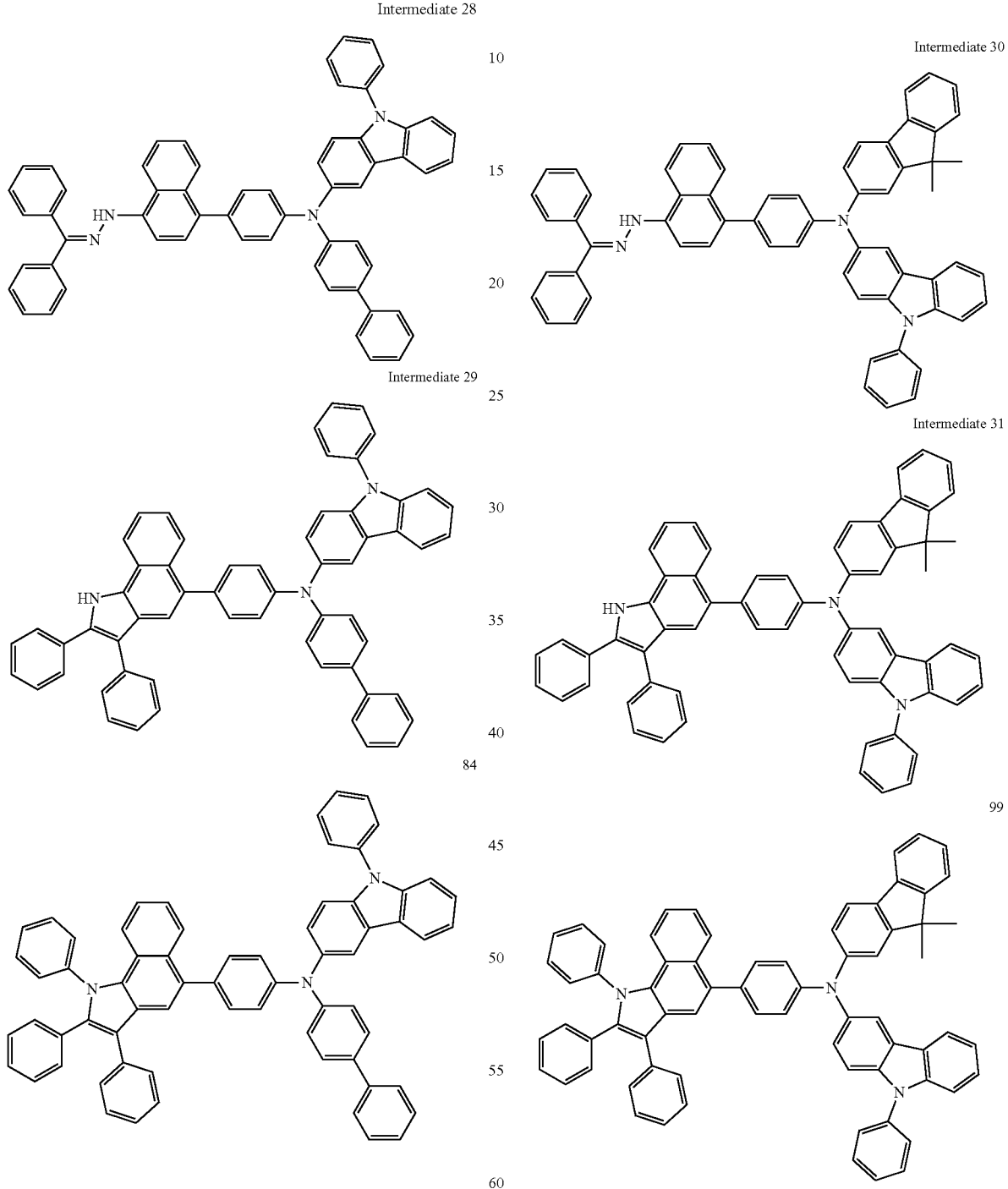

Compound 84 (yield: 71%) was synthesized in the same manner as Compound 1, except that Intermediate 28 and Intermediate 29 were synthesized using Intermediate 12 instead of Intermediate 8, and Intermediate 29 was reacted with bromobenzene. The obtained compound was identified by HR-MS and NMR. $C_{66}H_{45}N_3$ calc. 879.3613; found 879.3617; $^1$H NMR (CDCl$_3$, 400 MHz) δ (ppm) 8.25-8.20 (m, 2H), 7.93 (d, 1H), 7.76 (d, 2H), 7.71-7.64 (m, 4H), 7.69-7.25 (m, 30H), 7.05 (d, 2H), 6.86-6.79 (m, 4H).

SYNTHESIS EXAMPLE 24

Synthesis of Compound 99

Compound 99 (yield: 62%) was synthesized in the same manner as Compound 1, except that Intermediate 30 and Intermediate 31 were synthesized using Intermediate 13 instead of Intermediate 8, and Intermediate 31 was reacted with bromobenzene. The obtained compound was identified by HR-MS and NMR. $C_{69}H_{49}N_3$ calc. 919.3926; found 919.3930; $^1$H NMR (CDCl$_3$, 400 MHz) δ (ppm) 8.24-8.20 (m, 2H), 7.98 (d, 1H), 7.93 (d, 1H), 7.71-7.65 (m, 2H), 7.60-7.20 (m, 30H), 7.14 (d, 1H), 7.05 (d, 2H), 6.95 (t, 1H), 6.79 (d, 2H), 6.72 (d, 1H), 1.95 (s, 6H).

EXAMPLE 1

An anode was prepared by cutting a Corning 15 Ωcm$^2$ (1200 Å) ITO glass substrate to a size of 50 mm×50 mm×0.7 mm, ultrasonically cleaning the glass substrate using isopropyl alcohol and pure water for 5 minutes each, and then irradiating with UV light for 30 minutes and exposing to ozone to clean. Then, the anode was mounted in a vacuum deposition apparatus.

2-TNATA (represented below) was vacuum-deposited on the glass substrate to form a HIL having a thickness of 600 Å. Compound 1 (as a hole transport material) was vacuum deposited on the HIL to form a HTL having a thickness of 300 Å.

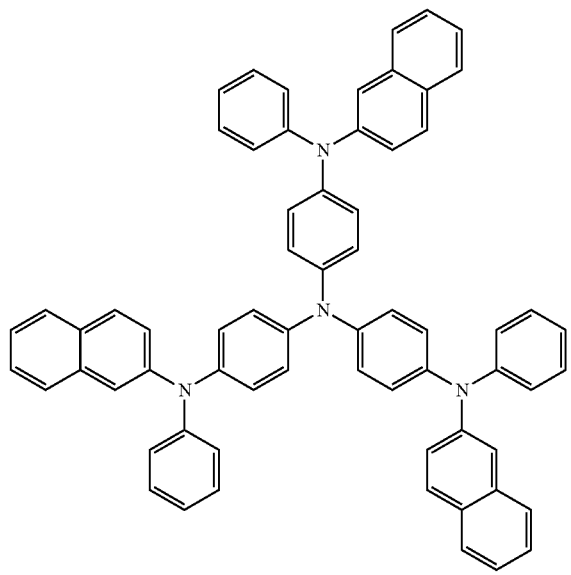

2-TNATA

Then, Alq$_3$ (as a green fluorescent host) and C545T (as a green fluorescent dopant) were simultaneously deposited in a weight ratio of 98:2, respectively, on the HTL, to form an EML having a thickness of 300 Å.

Then, Alq$_3$ was deposited on the EML to form an ETL having a thickness of 300 Å, and then LiF (which is a halogenated alkali metal) was deposited on the ETL to form an EIL having a thickness of 10 Å. Then, Al was deposited on the EIL to a thickness of 3000 Å (cathode), thereby forming a LiF/Al electrode. As a result, the manufacture of an organic light-emitting device was completed.

EXAMPLE 2

An organic luminescence device was manufactured in the same manner as in Example 1, except that Compound 2 was used as the hole transport material.

EXAMPLE 3

An organic luminescence device was manufactured in the same manner as in Example 1, except that Compound 8 was used as the hole transport material.

EXAMPLE 4

An organic luminescence device was manufactured in the same manner as in Example 1, except that Compound 29 was used as the hole transport material.

EXAMPLE 5

An organic luminescence device was manufactured in the same manner as in Example 1, except that Compound 32 was used as the hole transport material.

EXAMPLE 6

An organic luminescence device was manufactured in the same manner as in Example 1, except that Compound 58 was used as the hole transport material.

EXAMPLE 7

An organic luminescence device was manufactured in the same manner as in Example 1, except that Compound 81 was used as the hole transport material.

EXAMPLE 8

An organic luminescence device was manufactured in the same manner as in Example 1, except that Compound 84 was used as the hole transport material.

EXAMPLE 9

An organic luminescence device was manufactured in the same manner as in Example 1, except that Compound 99 was used as the hole transport material.

COMPARATIVE EXAMPLE 1

An organic luminescence device was manufactured in the same manner as Example 1, except that the HTL was formed using 4,4'-bis[N-(1-naphthyl)-N-phenylamino]biphenyl (hereinafter referred to as NPB) instead of Compound 1.

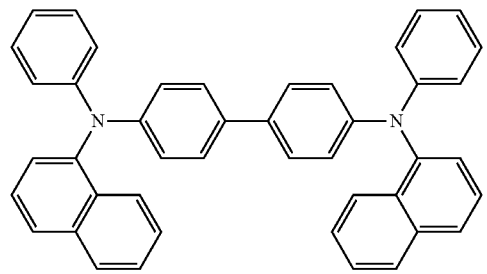

NPB

Driving voltage, brightness, color coordinates, and luminescent efficiency of the organic luminescence devices manufactured according to Examples 1-9 and Comparative Example 1 were measured at a current density of 50 mA/cm$^2$. The results are shown in Table 1 below.

TABLE 1

| | Hole transport material | Driving voltage (V) | Brightness (cd/m²) | Color coordinate | Luminescent efficiency (cd/A) |
|---|---|---|---|---|---|
| Example 1 | Compound 1 | 6.45 | 8340 | (0.310, 0.643) | 16.68 |
| Example 2 | Compound 2 | 6.47 | 8120 | (0.311, 0.642) | 16.24 |
| Example 3 | Compound 8 | 6.48 | 8096 | (0.309, 0.642) | 16.19 |
| Example 4 | Compound 29 | 6.45 | 8620 | (0.310, 0.642) | 17.24 |
| Example 5 | Compound 32 | 6.43 | 8590 | (0.311, 0.641) | 17.18 |
| Example 6 | Compound 58 | 6.54 | 7920 | (0.311, 0.641) | 15.84 |
| Example 7 | Compound 81 | 6.82 | 7624 | (0.312, 0.643) | 15.24 |
| Example 8 | Compound 84 | 6.49 | 8132 | (0.310, 0.642) | 16.26 |
| Example 9 | Compound 99 | 6.79 | 7842 | (0.312, 0.642) | 15.68 |
| Comparative Example 1 | NPB | 7.45 | 6102 | (0.309, 0.642) | 12.2 |

The driving voltages of all of the organic luminescence devices using the amine compounds represented by Formula 1 as the hole transport material were lower by 1 V or more than that of the organic luminescence device using NPB. Also, the organic luminescence devices using the amine compounds represented by Formula 1 showed improved I-V-L characteristics (meaning high efficiency). In particular, the lifetime of the organic luminescence devices manufactured according to Examples 1-9 was increased by 100% or more compared to that of the organic luminescence device manufactured according to Comparative Example 1. Lifetimes of the organic luminescence devices are shown in Table 2 below.

Half-lifetimes of the organic luminescence devices manufactured according to Examples 1-9 and Comparative Example 1 were measured. The results are shown in Table 2.

TABLE 2

| | Hole transport material | Half lifetime (hr @ 100 mA/cm²) |
|---|---|---|
| Example 1 | Compound 1 | 520 hr |
| Example 2 | Compound 2 | 541 hr |
| Example 3 | Compound 8 | 523 hr |
| Example 4 | Compound 29 | 532 hr |
| Example 5 | Compound 32 | 548 hr |
| Example 6 | Compound 58 | 517 hr |
| Example 7 | Compound 81 | 487 hr |
| Example 8 | Compound 84 | 521 hr |
| Example 9 | Compound 99 | 498 hr |
| Comparative Example 1 | NPB | 237 hr |

Referring to Table 2, it can be seen that the organic luminescence devices manufactured according to Examples 1-9 had longer half-lifetimes than the organic luminescence device manufactured according to Comparative Example 1.

The amine compounds represented by Formula 1 according to embodiments of the present invention have good electrical characteristics and charge transport characteristics as well as good hole injection and transport capabilities, and thus are useful as hole injection material and/or hole transport materials and as EML host materials.

Organic luminescence devices according to embodiments of the present invention including organic layers including an amine compound of Formula 1 exhibit high efficiency, low driving voltages, high brightness, and long lifetimes.

While the present invention has been illustrated and described with reference to certain exemplary embodiments, it is understood by those of ordinary skill in the art that various modifications and changes may be made to the described embodiments without departing from the spirit and scope of the present invention as defined by the following claims.

What is claimed is:

1. A heteroarylamine compound represented by Formula 1:

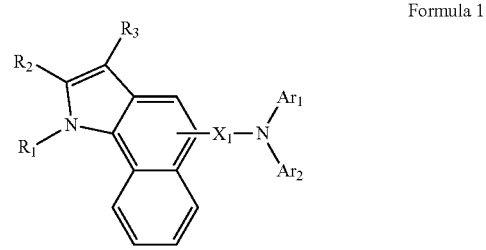

Formula 1 wherein:
each of $Ar_1$ and $Ar_2$ is independently selected from the group consisting of substituted and unsubstituted C6-C60 aryl groups, substituted and unsubstituted C4-C60 heteroaryl groups, and substituted and unsubstituted C6-C60 condensed polycyclic groups;
$X_1$ is selected from the group consisting of substituted and unsubstituted C6-C30 arylene groups, substituted and unsubstituted C4-C30 heteroarylene groups, and substituted and unsubstituted C6-C30 condensed polycyclic groups; and
each of $R_1$, $R_2$, and $R_3$ is independently selected from the group consisting of hydrogen atoms, heavy hydrogen atoms, substituted and unsubstituted C1-CSO alkyl groups, substituted and unsubstituted C1-CSO alkoxy groups, substituted and unsubstituted C6-C60 aryl groups, substituted and unsubstituted C3-CSO carbocyclic groups, substituted and unsubstituted C4-C60 hetero aryl groups, substituted and unsubstituted C4-C60 heterocyclic groups, substituted and unsubstituted C6-C60 condensed polycyclic groups, halogen atoms, cyano groups, hydroxyl groups, and carboxyl groups.

2. The heteroarylamine compound of claim 1, wherein the compound represented by Formula 1 is selected from the group consisting 5 of compounds represented by Formulae 2-6:

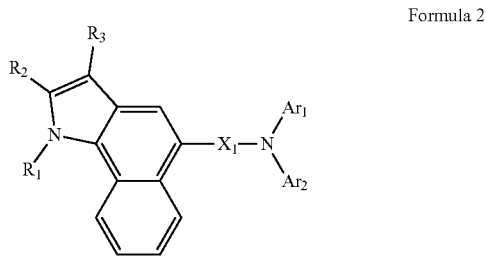

Formula 2

-continued

Formula 3
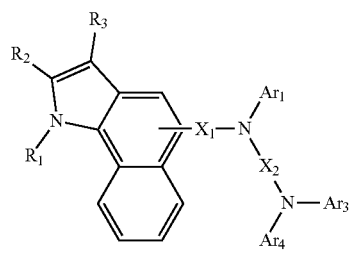

Formula 4
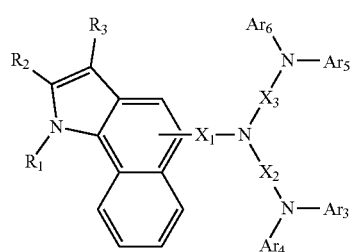

Formula 5
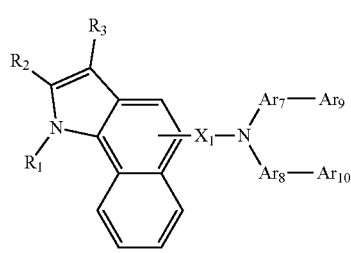

Formula 6
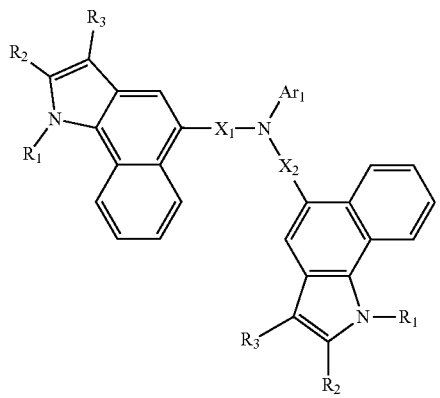

wherein:
 each of Ar$_1$ through Ar$_6$, Ar$_9$, and Ar$_{10}$ is independently selected from the group consisting of substituted and unsubstituted C6-C60 aryl groups, substituted and unsubstituted C4-C60 heteroaryl groups, and substituted and unsubstituted C6-C60 condensed polycyclic groups;
 each of X$_1$, X$_2$, X$_3$, Ar$_7$, and Ar$_8$ is independently selected from the group consisting of substituted and unsubstituted C6-C30 arylene groups, substituted and unsubstituted C4-C30 heteroarylene groups, and substituted and unsubstituted C6-C30 condensed polycyclic groups; and
 each of R$_1$, R$_2$, and R$_3$ is independently selected from the group consisting of hydrogen atoms, heavy hydrogen atoms, substituted and unsubstituted C1-C50 alkyl groups, substituted and unsubstituted C1-C50 alkoxy groups, substituted and unsubstituted C6-C60 aryl groups, substituted and unsubstituted C3-C50 carbocyclic groups, substituted and unsubstituted C4-C60 hetero aryl groups, substituted and unsubstituted C4-C60 heterocyclic groups, substituted and unsubstituted C6-C60 condensed polycyclic groups, halogen atoms, cyano groups, hydroxyl groups, and carboxyl groups.

3. The heteroarylamine compound of claim 2, wherein each of X$_1$, X$_2$, and X$_3$ in Formulae 2 through 6 is independently selected from the group consisting of:

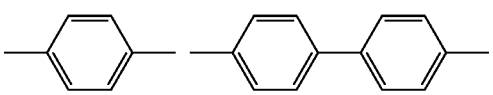

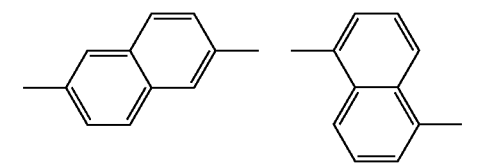

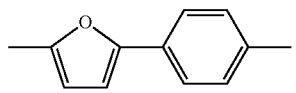

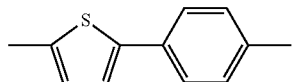

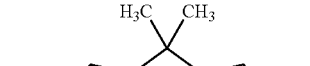

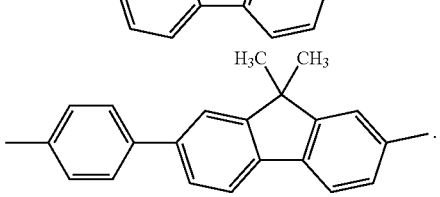

4. The heteroarylamine compound of claim 2, wherein each of Ar$_1$ through Ar$_6$, Ar$_9$, and Ar$_{10}$ in Formulae 2 through 6 is independently selected from the group consisting of:

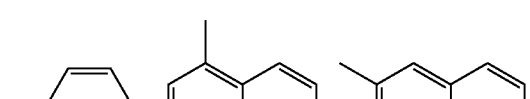

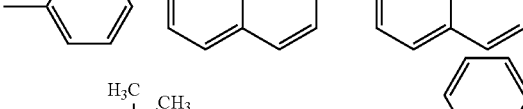

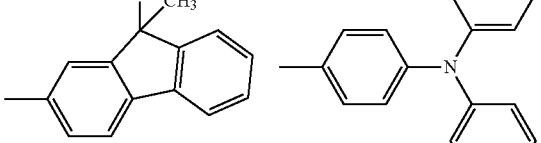

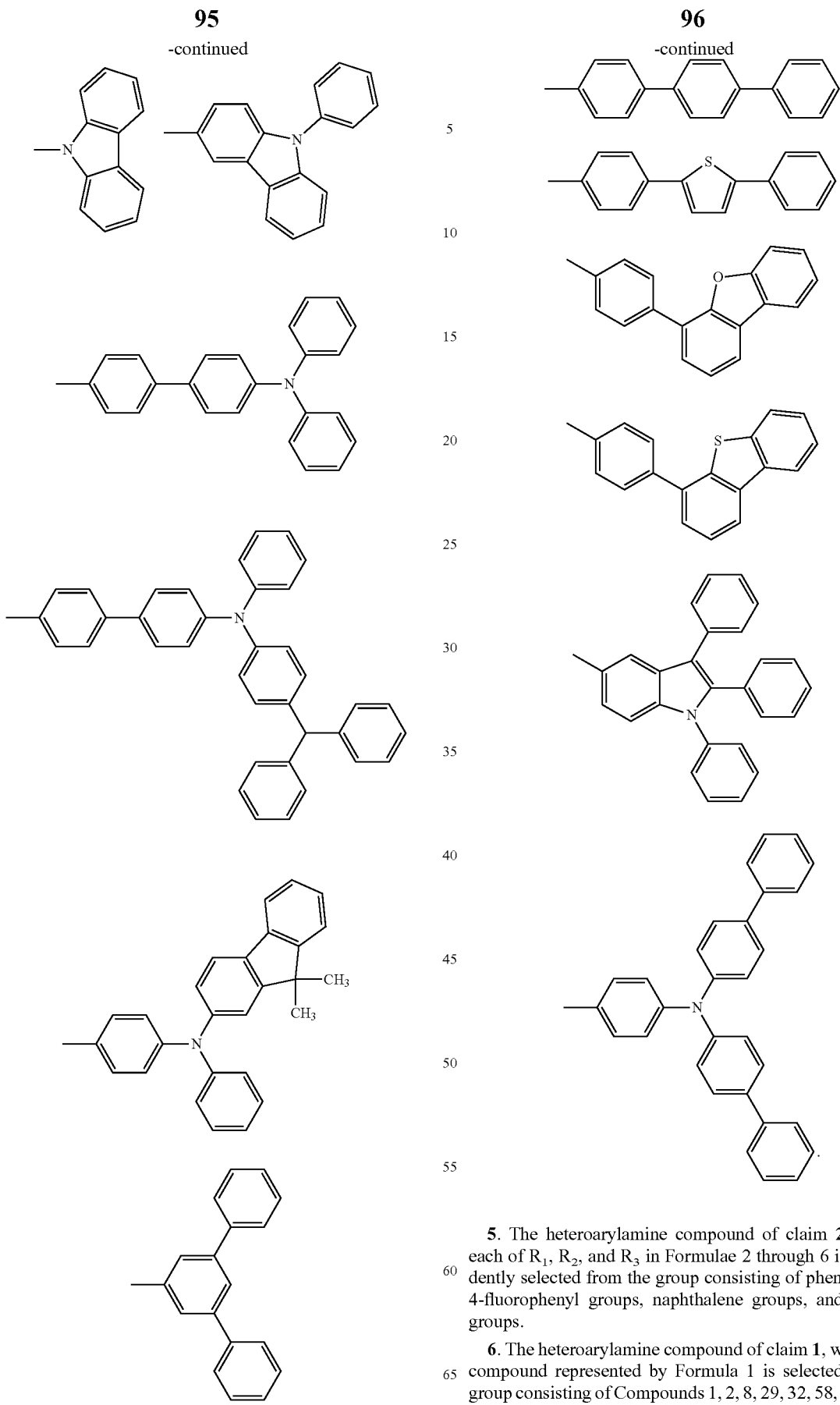

5. The heteroarylamine compound of claim 2, wherein each of $R_1$, $R_2$, and $R_3$ in Formulae 2 through 6 is independently selected from the group consisting of phenyl groups, 4-fluorophenyl groups, naphthalene groups, and biphenyl groups.

6. The heteroarylamine compound of claim 1, wherein the compound represented by Formula 1 is selected from the group consisting of Compounds 1, 2, 8, 29, 32, 58, 81, 84 and 99:

1
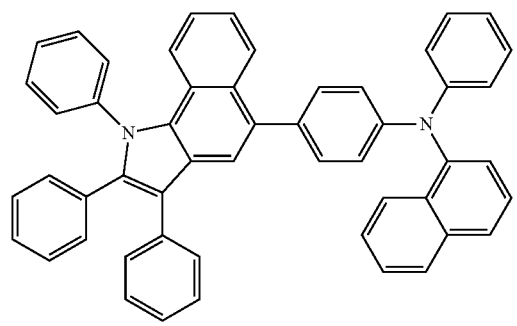
2
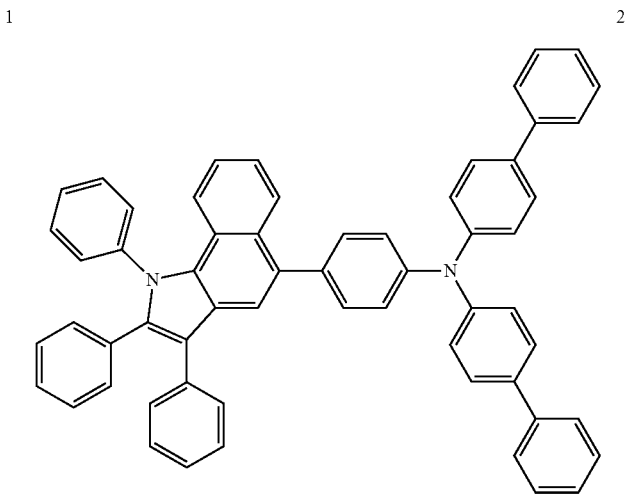
8
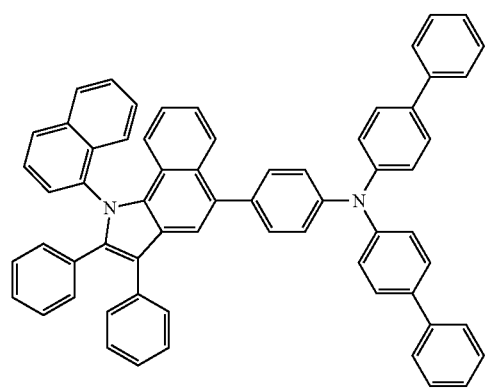
29
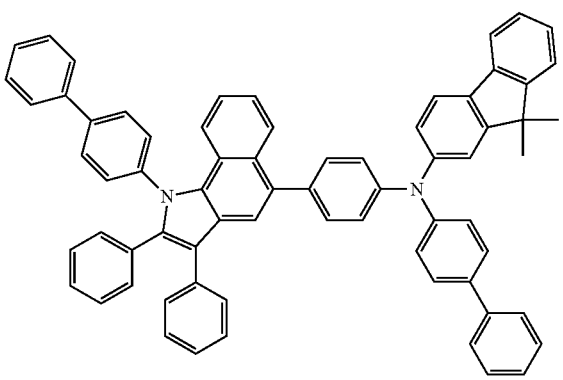
32
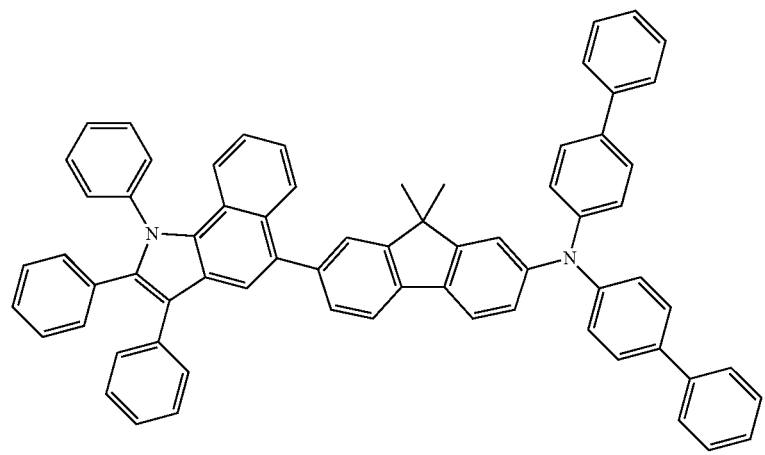

58
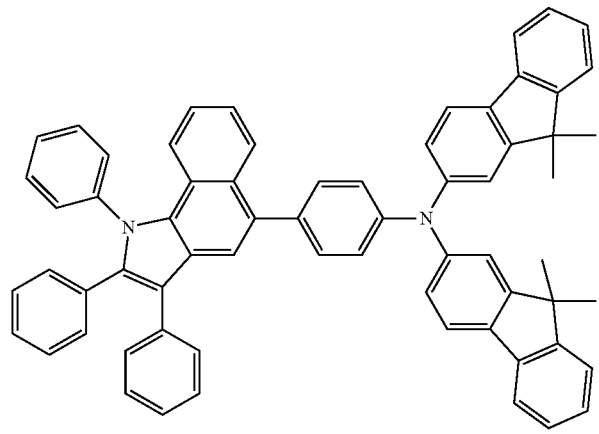
81
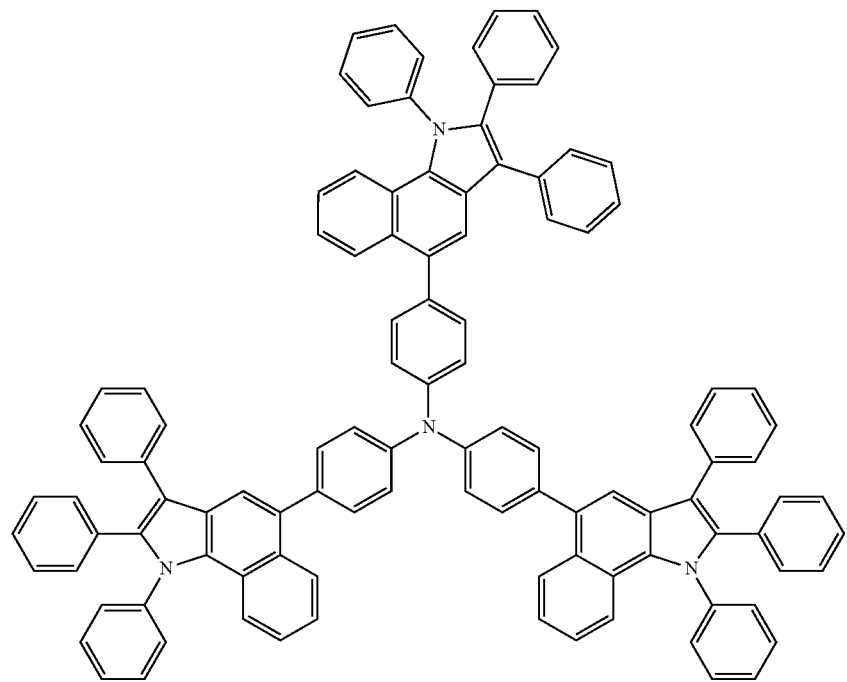
84 99
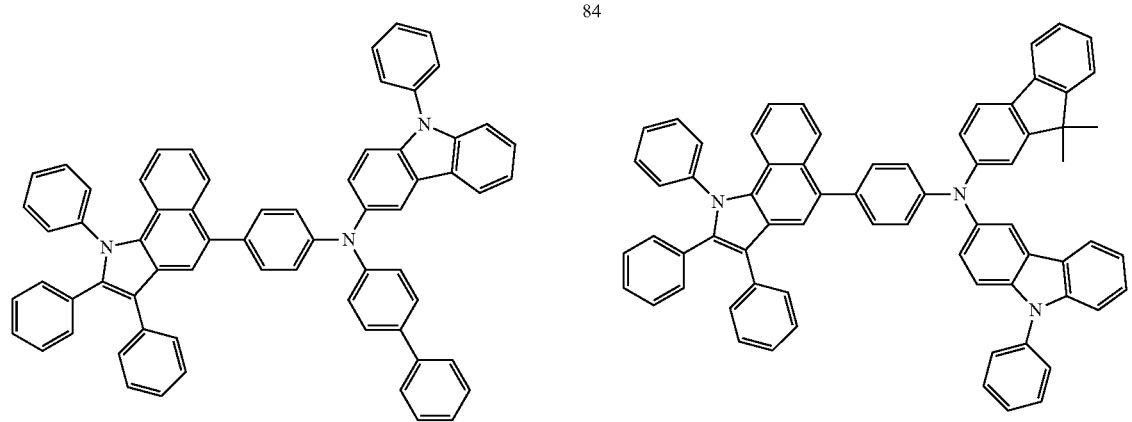

7. An organic luminescence device comprising: a first electrode, a second electrode, and an organic layer between the first electrode and the second electrode,
   wherein the organic layer comprises at least one layer comprising the heteroarylamine compound of claim 1.

8. The organic luminescence device of claim 7, wherein the organic layer comprises a hole injection layer or a hole transport layer.

9. The organic luminescence device of claim 7, wherein the organic layer comprises an emitting layer or a single layer having hole injection capabilities and hole transport capabilities.

10. The organic luminescence device of claim 7, wherein the organic layer comprises an emitting layer, and wherein the compound represented by Formula 1 is a host for a fluorescence or phosphorescence organic light emitting device.

11. The organic luminescence device of claim 7, wherein the organic layer comprises a hole injection layer, a hole transport layer, and an emitting layer, wherein the hole injection layer or the hole transport layer comprises the compound represented by Formula 1, and the emitting layer comprises an anthracene compound or a styryl compound.

12. The organic luminescence device of claim 7, wherein the organic layer comprises a hole injection layer, a hole transport layer, and an emitting layer, wherein the hole injection layer or the hole transport layer comprises the compound represented by Formula 1, and the emitting layer comprises an arylamine compound.

13. The organic luminescence device of claim 7, wherein the organic layer comprises a hole injection layer, a hole transport layer, and an emitting layer, wherein the hole injection layer or the hole transport layer comprises the compound represented by Formula 1, and the emitting layer comprises a green emission layer, a blue emission layer, a red emission layer, and a white emission layer, and at least one of the green emission layer, the blue emission layer, the red emission layer, and the white emission layer comprises a phosphorescent compound.

14. The organic luminescence device of claim 7, wherein the organic layer comprises at least one layer selected from the group consisting of a hole injection layer, a hole transport layer, an electron blocking layer, an emitting layer, a hole blocking layer, an electron transport layer, or an electron injection layer.

15. The organic luminescence device of claim 11, wherein the organic luminescence device has a first electrode/hole injection layer/emitting layer/second electrode structure, a first electrode/hole injection layer/hole transport layer/emitting layer/electron transport layer/second electrode structure, or a first electrode/hole injection layer/hole transport layer/emitting layer/electron transport layer/electron injection layer/second electrode structure.

16. A flat panel display device comprising the organic luminescence device of claim 7, wherein the first electrode of the organic light-emitting device is electrically connected to a source electrode or a drain electrode of a thin-film transistor.

17. An organic luminescence display device comprising a first electrode, a second electrode, and an organic layer between the first electrode and the second electrode, wherein the organic layer comprises at least one layer comprising the heteroarylamine compound of claim 1, the at least one layer being formed using a wet process.

* * * * *